(12) United States Patent
Kang et al.

(10) Patent No.: US 12,035,921 B2
(45) Date of Patent: Jul. 16, 2024

(54) ROBOTIC SYSTEMS AND METHODS FOR MANIPULATING A CUTTING GUIDE FOR A SURGICAL INSTRUMENT

(71) Applicant: MAKO Surgical Corp., Weston, FL (US)

(72) Inventors: Hyosig Kang, Weston, FL (US); Jason Karl Otto, Sioux Falls, SD (US); Matthew Harrow, Plantation, FL (US)

(73) Assignee: MAKO Surgical Corp., Weston, FL (US)

( * ) Notice: Subject to any disclaimer, the term of this patent is extended or adjusted under 35 U.S.C. 154(b) by 0 days.

(21) Appl. No.: 18/134,105

(22) Filed: Apr. 13, 2023

(65) Prior Publication Data

US 2023/0248371 A1    Aug. 10, 2023

Related U.S. Application Data

(63) Continuation of application No. 16/845,823, filed on Apr. 10, 2020, now Pat. No. 11,684,374.

(Continued)

(51) Int. Cl.
*A61B 17/14* (2006.01)
*A61B 17/15* (2006.01)
(Continued)

(52) U.S. Cl.
CPC .............. *A61B 17/14* (2013.01); *A61B 17/15* (2013.01); *A61B 34/20* (2016.02); *A61B 34/32* (2016.02);
(Continued)

(58) Field of Classification Search
CPC ......... A61B 17/14; A61B 32/20; A61B 34/20; A61B 34/32; A61B 90/50; A61B 17/15;
(Continued)

(56) References Cited

U.S. PATENT DOCUMENTS

| 4,979,949 A | 12/1990 | Matsen, III et al. |
| 5,571,110 A | 11/1996 | Matsen, III et al. |

(Continued)

FOREIGN PATENT DOCUMENTS

| CN | 101448467 A | 6/2009 |
| CN | 107405156 A | 11/2017 |

(Continued)

OTHER PUBLICATIONS

Partial International Search Report for Application No. PCT/US2020/027665 dated Jul. 15, 2020, 4 pages.

(Continued)

*Primary Examiner* — Kevin T Truong
*Assistant Examiner* — Diana Jones
(74) *Attorney, Agent, or Firm* — Howard & Howard Attorneys PLLC

(57) ABSTRACT

Surgical systems and methods for use with a hand-guided tool. The surgical system includes a robotic manipulator that holds a tool guide. The tool guide receives and guides the surgical tool to enable the tool to manipulate a bone. The robotic manipulator autonomously aligns the tool guide to a target orientation relative to the bone. The tool guide is moved to an initial location adjacent to the bone while remaining aligned with the target orientation. The initial location is suitable for the tool to perform an initial manipulation of the bone. The robotic manipulator facilitates withdrawal of the tool guide away from the initial location to a spaced location after the initial manipulation of the bone while maintaining alignment of the tool guide with the target orientation at the spaced guide location. The spaced guide location is suitable for the tool to perform a further manipulation of the bone.

20 Claims, 27 Drawing Sheets

Related U.S. Application Data

(60) Provisional application No. 62/833,227, filed on Apr. 12, 2019.

(51) Int. Cl.
  *A61B 34/20* (2016.01)
  *A61B 34/32* (2016.01)
  *A61B 90/00* (2016.01)
  *A61B 90/50* (2016.01)

(52) U.S. Cl.
  CPC ...... *A61B 90/50* (2016.02); *A61B 2034/2048* (2016.02); *A61B 2034/2051* (2016.02); *A61B 2034/2055* (2016.02); *A61B 2034/2063* (2016.02); *A61B 2090/064* (2016.02); *A61B 2090/066* (2016.02)

(58) Field of Classification Search
  CPC .... A61B 2034/2058; A61B 2034/2051; A61B 2034/2055; A61B 2034/2063
  See application file for complete search history.

(56) References Cited

U.S. PATENT DOCUMENTS

| | | |
|---|---|---|
| 6,711,431 B2 | 3/2004 | Sarin et al. |
| 6,923,817 B2 | 8/2005 | Carson et al. |
| 7,104,996 B2 | 9/2006 | Bonutti |
| 7,163,542 B2 | 1/2007 | Ryan |
| 7,497,860 B2 | 3/2009 | Carusillo et al. |
| 7,635,390 B1 | 12/2009 | Bonutti |
| 7,704,254 B2 | 4/2010 | Walen |
| 7,708,741 B1 | 5/2010 | Bonutti |
| 7,725,162 B2 | 5/2010 | Malackowski et al. |
| 7,780,681 B2 | 8/2010 | Sarin et al. |
| 7,794,467 B2 | 9/2010 | McGinley et al. |
| 7,831,292 B2 | 11/2010 | Quaid et al. |
| 7,840,253 B2 | 11/2010 | Tremblay et al. |
| 7,959,635 B1 | 6/2011 | Bonutti |
| 8,010,180 B2 | 8/2011 | Quaid et al. |
| 8,239,001 B2 | 8/2012 | Verard et al. |
| 8,271,069 B2 | 9/2012 | Jascob et al. |
| 8,435,246 B2 | 5/2013 | Fisher et al. |
| 8,444,647 B2 | 5/2013 | Walen et al. |
| 8,679,125 B2 | 3/2014 | Smith et al. |
| 8,801,720 B2 | 8/2014 | Park et al. |
| 8,828,013 B2 | 9/2014 | Fisher et al. |
| 8,882,777 B2 | 11/2014 | Heavener et al. |
| 8,977,021 B2 | 3/2015 | Kang et al. |
| 9,017,336 B2 | 4/2015 | Park et al. |
| 9,072,531 B2 | 7/2015 | Fitz et al. |
| 9,119,655 B2 | 9/2015 | Bowling et al. |
| 9,125,673 B2 | 9/2015 | Fitz et al. |
| 9,326,780 B2 | 5/2016 | Wong et al. |
| 9,345,548 B2 | 5/2016 | Schoenefeld et al. |
| 9,421,019 B2 | 8/2016 | Plaskos et al. |
| 9,504,530 B2 | 11/2016 | Hartmann et al. |
| 9,566,122 B2 | 2/2017 | Bowling et al. |
| 9,579,110 B2 | 2/2017 | Bojarski et al. |
| 9,585,725 B2 | 3/2017 | Bonutti |
| 9,588,587 B2 | 3/2017 | Otto et al. |
| 9,622,823 B2 | 4/2017 | Bozung et al. |
| 9,629,687 B2 | 4/2017 | Bonutti |
| 9,649,164 B2 | 5/2017 | Kim et al. |
| 9,655,683 B2 | 5/2017 | Iorgulescu et al. |
| 9,668,747 B2 | 6/2017 | Metzger et al. |
| 9,693,783 B2 | 7/2017 | Fisher et al. |
| 9,737,311 B2 | 8/2017 | Lavallee et al. |
| 9,795,394 B2 | 10/2017 | Bonutti |
| 9,808,318 B2 | 11/2017 | Bonutti |
| 9,812,035 B2 | 11/2017 | Stuart et al. |
| 9,861,446 B2 | 1/2018 | Lang |
| 9,877,793 B2 | 1/2018 | Bonutti |
| 10,004,565 B2 | 6/2018 | Kang et al. |
| 10,098,649 B2 | 10/2018 | Nikou et al. |
| 10,130,428 B2 | 11/2018 | Nikou et al. |
| 10,130,478 B2 | 11/2018 | Mahfouz |
| 10,136,952 B2 | 11/2018 | Couture et al. |
| 10,159,534 B2 | 12/2018 | Maillet et al. |
| 10,206,697 B2 | 2/2019 | Metzger et al. |
| 10,231,739 B1 | 3/2019 | Bonutti |
| 10,251,663 B2 | 4/2019 | Behzadi |
| 10,285,683 B2 | 5/2019 | Plaskos et al. |
| 10,307,256 B2 | 6/2019 | Andriacchi et al. |
| 10,363,052 B2 | 7/2019 | Park et al. |
| 10,368,878 B2 | 8/2019 | Avallee et al. |
| 10,383,638 B2 | 8/2019 | Cheal et al. |
| 10,398,514 B2 | 9/2019 | Ryan et al. |
| 10,398,560 B2 | 9/2019 | Termanini |
| 10,426,540 B2 | 10/2019 | Behzadi |
| 10,449,004 B2 | 10/2019 | Ferro et al. |
| 10,575,913 B2 | 3/2020 | Iorgulescu et al. |
| 10,594,998 B1 | 3/2020 | Casas |
| 10,595,880 B2 | 3/2020 | Otto et al. |
| 10,603,113 B2 | 3/2020 | Lang |
| 10,610,301 B2 | 4/2020 | Quaid, III |
| 10,653,488 B2 | 5/2020 | Kang et al. |
| 10,667,865 B2 | 6/2020 | Jaramaz et al. |
| 10,682,129 B2 | 6/2020 | Stanton |
| 10,682,182 B2 | 6/2020 | Hogan et al. |
| 10,687,829 B2 | 6/2020 | Singh et al. |
| 10,702,344 B2 | 7/2020 | McCabe et al. |
| 11,844,577 B2 | 12/2023 | Kang et al. |
| 2003/0130576 A1 | 7/2003 | Seeley et al. |
| 2006/0142657 A1 | 6/2006 | Quaid et al. |
| 2007/0156157 A1 | 7/2007 | Nahum et al. |
| 2012/0123418 A1 | 5/2012 | Giurgi et al. |
| 2014/0180290 A1 | 6/2014 | Otto et al. |
| 2014/0188129 A1 | 7/2014 | Kang |
| 2015/0245878 A1 | 9/2015 | Jaramaz et al. |
| 2016/0113720 A1* | 4/2016 | Lavallee ................ A61B 17/15 901/9 |
| 2016/0235492 A1 | 8/2016 | Morard et al. |
| 2016/0242861 A1 | 8/2016 | Flatt et al. |
| 2016/0331479 A1 | 11/2016 | Crawford |
| 2017/0119476 A1 | 5/2017 | Stifter et al. |
| 2017/0128218 A1 | 5/2017 | Andriacchi et al. |
| 2017/0164957 A1 | 6/2017 | Bojarski et al. |
| 2017/0360512 A1 | 12/2017 | Couture et al. |
| 2018/0116739 A1 | 5/2018 | Gogarty et al. |
| 2018/0116740 A1 | 5/2018 | Gogarty et al. |
| 2018/0125597 A1 | 5/2018 | Gogarty et al. |
| 2018/0132941 A1 | 5/2018 | Haider et al. |
| 2018/0157238 A1 | 6/2018 | Gogarty et al. |
| 2018/0242962 A1 | 8/2018 | Walen et al. |
| 2018/0325608 A1 | 11/2018 | Kang et al. |
| 2018/0344409 A1 | 12/2018 | Bonny et al. |
| 2019/0008525 A1 | 1/2019 | Jaramaz et al. |
| 2019/0083109 A1 | 3/2019 | Steger et al. |
| 2019/0192231 A1 | 6/2019 | Levine |
| 2019/0272917 A1 | 9/2019 | Couture et al. |
| 2020/0008813 A1 | 1/2020 | Bonny et al. |
| 2020/0085517 A1 | 3/2020 | Maratt |
| 2020/0323540 A1 | 10/2020 | Kang et al. |

FOREIGN PATENT DOCUMENTS

| | | |
|---|---|---|
| WO | 2005122916 A1 | 12/2005 |
| WO | 2011070476 A1 | 6/2011 |
| WO | 2018076114 A1 | 5/2018 |
| WO | 2018103945 A1 | 6/2018 |
| WO | 2019055904 A1 | 3/2019 |

OTHER PUBLICATIONS

English language abstract for CN 101448467 A extracted from espacenet.com database on Mar. 18, 2024, 2 pages.
English language abstract for CN 107405156 A extracted from espacenet.com database on Mar. 18, 2024, 2 pages.

* cited by examiner

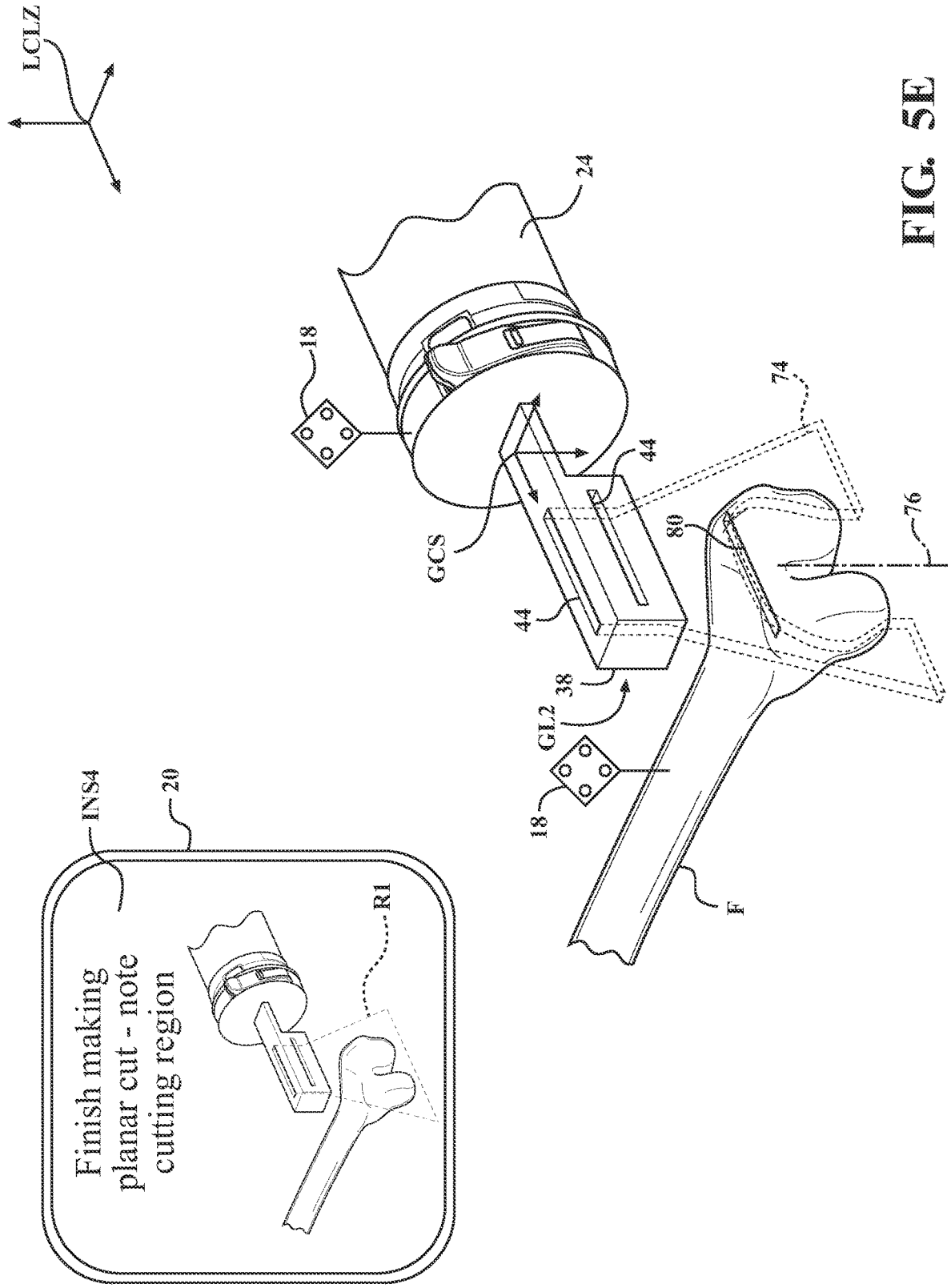

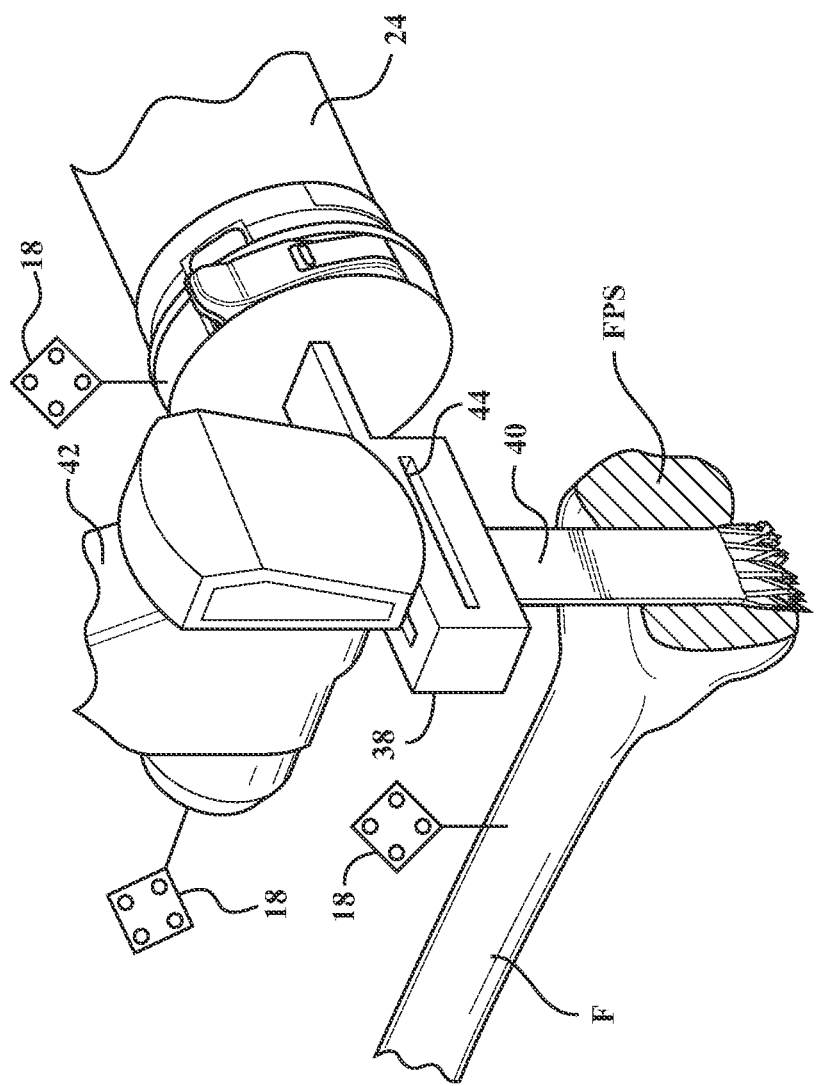

ROBOTIC SYSTEMS AND METHODS FOR MANIPULATING A CUTTING GUIDE FOR A SURGICAL INSTRUMENT

CROSS-REFERENCE TO RELATED APPLICATIONS

The subject application is a continuation of U.S. patent application Ser. No. 16/845,823, filed Apr. 10, 2020, which claims priority to and all the benefits of U.S. Provisional Patent App. No. 62/833,227, filed Apr. 12, 2019, the entire contents of the aforementioned applications being hereby incorporated by reference.

BACKGROUND

It is prevalent to use powered surgical instruments, such as saws, drills, reamers, etc. during surgical procedures. Generally, these surgical instruments may be operated by a user such as a surgeon. The surgical instruments include a cutting tool which is configured to cut tissue of a patient, such as bone, ligaments, skin, or the like.

Often one or more cutting guides are employed to guide the cutting tools while making the necessary cuts. However, placing a cutting guide, which often includes fixing the cutting guide to the patient's tissue, can increase the time required for a surgery. Some of the goals of robotic surgery is to increase cutting accuracy and reduce cutting time. Accordingly, efforts have been made to employ robotic systems to place cutting guides. However, further improvements to such robotic systems are needed.

SUMMARY

A robotic surgery system is provided for use with a surgical saw having a saw blade. The robotic surgery system comprises a robotic manipulator and an end effector including a cutting guide to be coupled to the robotic manipulator. The cutting guide is configured to guide the saw blade so that the saw blade cuts a bone along a desired cutting plane. A control system is coupled to the robotic manipulator to control a location of the cutting guide relative to the bone by: autonomously positioning the cutting guide at a target orientation relative to the bone so that the saw blade aligns with the desired cutting plane when the saw blade cooperates with the cutting guide; and constraining movement of the cutting guide as a user manually manipulates the end effector to cause the cutting guide to move toward the bone to an initial guide location adjacent to the bone such that the cutting guide remains in the target orientation at the initial guide location. The control system is configured to facilitate withdrawal of the cutting guide away from the initial guide location to a spaced guide location after the user makes an initial cut in the bone with the saw blade along the desired cutting plane. The cutting guide remains in the target orientation at the spaced guide location and the spaced guide location is suitable for the saw blade to continue cutting the bone along the desired cutting plane.

A method of controlling placement of a cutting guide configured to guide a saw blade of a surgical saw is provided so that the saw blade cuts a bone along a desired cutting plane. The cutting guide forms part of an end effector coupled to a robotic manipulator. The method comprises autonomously positioning the cutting guide at a target orientation relative to the bone so that the saw blade aligns with the desired cutting plane when the saw blade cooperates with the cutting guide. Movement of the cutting guide is constrained as a user manually manipulates the end effector to cause the cutting guide to move toward the bone to an initial guide location adjacent to the bone so that the cutting guide remains in the target orientation at the initial guide location. The method also comprises facilitating withdrawal of the cutting guide away from the initial guide location to a spaced guide location after the user makes an initial cut in the bone with the saw blade along the desired cutting plane so that the cutting guide remains in the target orientation at the spaced guide location, the spaced guide location being suitable for the saw blade to continue cutting the bone along the desired cutting plane.

Another robotic surgery system is provided that comprises a robotic manipulator and an end effector including a guide to be coupled to the robotic manipulator. The guide is configured to guide a surgical tool so that the surgical tool moves along a desired plane or axis to remove material from a bone. A control system is coupled to the robotic manipulator to control a location of the guide relative to the bone by: autonomously positioning the guide at a target orientation relative to the bone so that the surgical tool aligns with the desired plane or axis when the surgical tool is placed in the guide; and constraining movement of the guide as a user manually manipulates the end effector to cause the guide to move toward the bone to an initial guide location adjacent to the bone such that the guide remains in the target orientation at the initial guide location. The control system is configured to facilitate withdrawal of the guide away from the initial guide location to a spaced guide location after the user removes an initial amount of material from the bone with the surgical tool along the desired plane or axis. The guide remains in the target orientation at the spaced guide location and the spaced guide location is suitable for the surgical tool to continue removing material from the bone along the desired plane or axis.

Another robotic surgery system is provided for use with a cutting tool to perform a surgical procedure on a patient. The robotic surgery system comprises a robotic manipulator and an end effector including a cutting guide to be coupled to the robotic manipulator. The cutting guide is configured to guide the cutting tool so that the cutting tool cuts tissue of the patient. A control system is coupled to the robotic manipulator to control a location of the cutting guide relative to the tissue. A navigation system includes a tool tracker to track a position and orientation of the cutting tool relative to a customized virtual boundary associated with the tissue, wherein the customized virtual boundary is customized for the patient based on a virtual model associated with the tissue of the patient. The control system is configured to generate feedback in response to interaction between the cutting tool and the customized virtual boundary when the cutting tool cooperates with the cutting guide to cut the tissue. Feedback can include control of the cutting tool, and/or generating haptic audible, visual, and/or vibration feedback.

Another method is provided to treat tissue with a robotic manipulator and a cutting guide used with a cutting tool. The method comprises robotically controlling a location of the cutting guide relative to the tissue. A position and orientation of the cutting tool is tracked relative to a customized virtual boundary associated with the tissue, wherein the customized virtual boundary is customized for the patient based on a virtual model associated with the tissue of the patient. The method further comprises generating feedback in response to interaction between the cutting tool and the customized virtual boundary when the cutting tool cooperates with the cutting guide to cut the tissue. Feedback can include control of the cutting tool, and/or generating haptic audible, visual, and/or vibration feedback.

Another robotic surgery system is provided for use with a cutting tool to perform a surgical procedure on a patient. The robotic surgery system comprises a robotic manipulator and an end effector including a cutting guide to be coupled to the robotic manipulator. The cutting guide is configured to guide the cutting tool so that the cutting tool cuts tissue of the patient. A control system is coupled to the robotic manipulator to control a location of the cutting guide relative to the tissue. A navigation system tracks a position and orientation of the cutting guide relative to a patient-specific cutting boundary associated with the tissue, wherein the patient-specific cutting boundary is customized for the patient based on tissue of the patient. The control system is configured to autonomously move the cutting guide in one or more degrees of freedom in response to manual manipulation of the end effector so that the cutting guide is located in a manner to inhibit the cutting tool from cutting tissue beyond the patient-specific cutting boundary.

A surgery system is provided that comprises a surgical instrument having a cutting tool, a cutting guide configured to guide the cutting tool, and a control system. The control system is configured to determine a current engagement state of the cutting tool with the cutting guide and control operation of the surgical instrument based on the engagement state.

A method of controlling operation of a surgical instrument having a cutting tool for use with a cutting guide is provided. The method comprises determining a current engagement state of the cutting tool with the cutting guide and controlling operation of the surgical instrument based on the engagement state.

Another surgery system is provided that comprises a robotic manipulator, a cutting guide configured to be coupled to the robotic manipulator to guide a cutting tool, and a control system. The control system is configured to determine a current engagement state of the cutting tool with the cutting guide and control operation of the robotic manipulator based on the engagement state.

A method of controlling operation of a robotic manipulator and a cutting guide coupled to the robotic manipulator is provided. The cutting guide is used with a cutting tool. The method comprises determining a current engagement state of the cutting tool with the cutting guide and controlling operation of the robotic manipulator based on the engagement state.

BRIEF DESCRIPTION OF THE DRAWINGS

Advantages of the present disclosure will be readily appreciated as the same becomes better understood by reference to the following detailed description when considered in connection with the accompanying drawings.

FIGS. 5A through 5F illustrate a sequence of surgical steps carried out by the robotic surgery system during a surgical procedure.

DETAILED DESCRIPTION

Figure 1:
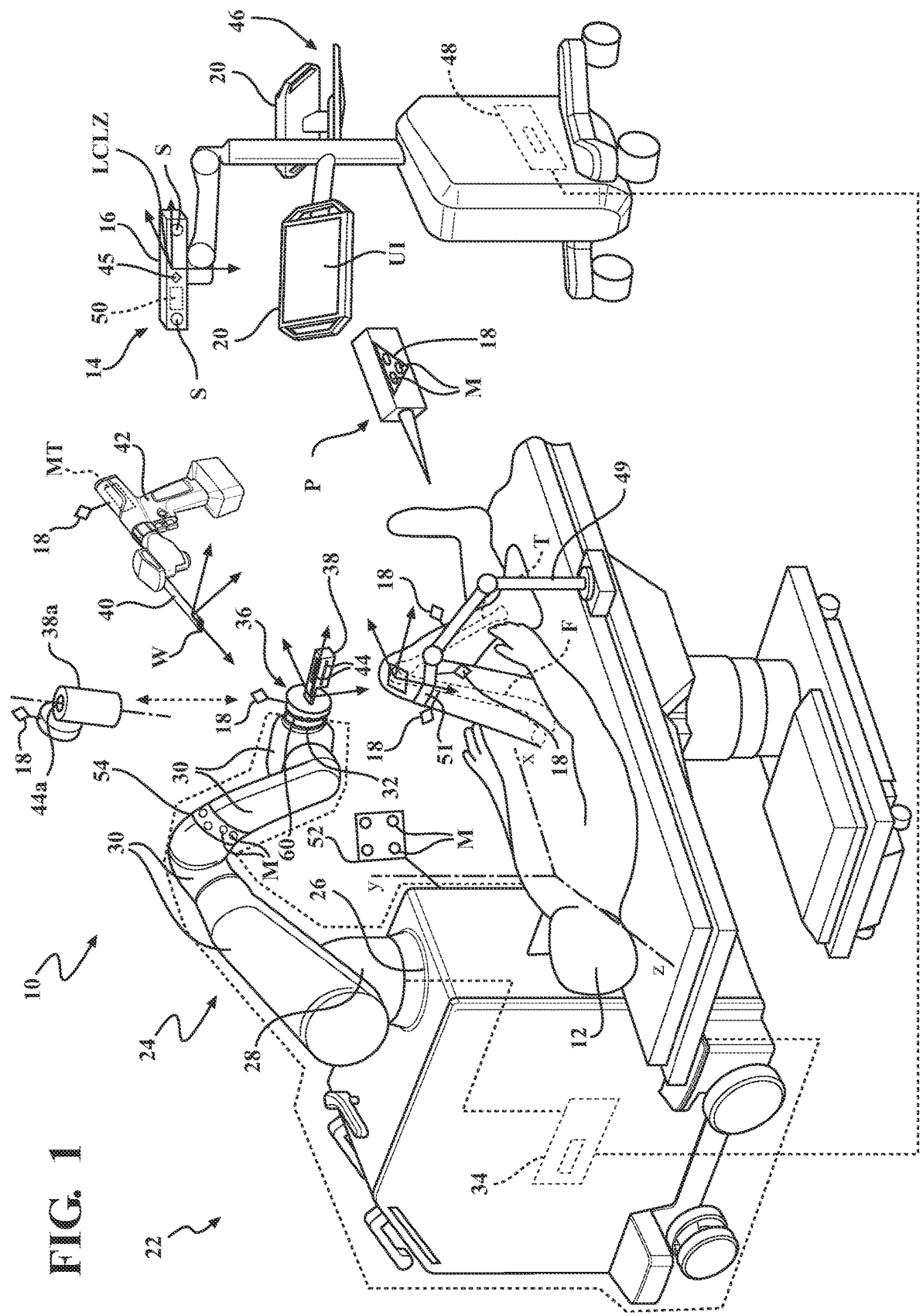
FIG. 1 is a perspective view of a robotic surgery system in an operating room.

Referring to FIG. 1, a robotic surgery system 10 is shown for use in surgical procedures. Such surgical procedures include, for example, knee procedures, hip procedures, shoulder procedures, ankle procedures, spine procedures, cranial procedures, dental procedures, and the like. Typically, the surgical procedure will include the cutting of hard tissue of a patient 12, such as bone, but may additionally or alternatively include the cutting of soft tissue, such as ligaments or skin. In some versions, the robotic surgery system 10 is designed to cut away tissue from the patient 12 to be replaced by surgical implants such as knee, hip, shoulder, ankle, spine, cranial, or dental implants, including unicompartmental, bicompartmental, or total knee implants, acetabular cups, femoral implants, humerus implants, glenoid implants, tibial implants, talus implants, pedicle screws, tissue anchors, electrodes, dental implants, and the like. It should be appreciated that although the description that follows focuses on placement of a total knee implant system on a femur F and tibia T, this is merely exemplary and is not intended to be limiting.

The robotic surgery system 10 comprises a navigation system 14 including a localizer 16, tracking devices 18, and one or more displays 20. The navigation system 14 is set up to track movement of various objects in the operating room, as described further below. The navigation system 14 tracks these objects for purposes of displaying their relative positions and orientations to a user and, in some cases, for purposes of controlling placement of one or more of the instruments or tools used in the robotic surgery system 10.

The robotic surgery system 10 also comprises a robotic manipulator 22 including a robotic arm 24 and a base 26. The robotic arm 24 includes a base link 28 rotatably coupled to the base 26 and a plurality of arm links 30 serially extending from the base link 28 to a distal end 32. The arm links 30 pivot/rotate about a plurality of joints in the robotic arm 24 via joint motors (not shown). Serial, parallel, or other robotic arm configurations may be employed. The robotic manipulator 22 may be disposed and supported on a floor surface, attached to the operating room table, and/or attached to the patient 12, or may be otherwise disposed to carry out the surgical procedure. In one embodiment, the robotic manipulator 22 comprises the RIO™ Robotic Arm Interactive Orthopedic System manufactured by MAKO Surgical Corp. of Fort Lauderdale, FL, USA.

A manipulator controller 34 is coupled to the robotic manipulator 22 to provide control of the robotic manipulator 22. The manipulator controller 34 may comprise one or more computers, or any other suitable form of controller. The manipulator controller 34 may have a central processing unit (CPU) and/or other processors, memory (not shown), and storage (not shown). The manipulator controller 34 is loaded with software as described below. The processors could include one or more processors to control operation of the robotic manipulator 22. The processors can be any type of microprocessor, multi-processor, and/or multi-core processing system. The manipulator controller 34 may additionally or alternatively comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor.

An end effector 36 is removably coupled to the distal end 32 of the robotic arm 24. The end effector 36 includes a cutting guide 38. The cutting guide 38 is shaped and configured to guide a cutting tool 40 of a free-hand surgical instrument 42 so that the cutting tool 40 cuts the tissue of the patient 12 in a desired manner (e.g., along a desired cutting plane, along a desired trajectory, or the like). More specifically, the cutting tool 40 cooperates with the cutting guide 38 to be guided into desired positions and/or orientations relative to the tissue of the patient 12. The cutting guide 38 has one or more guide portions 44 for receiving the cutting tool 40. In the version shown, the guide portions 44 comprise blade-receiving slots for receiving the cutting tool 40, which is in the form of a saw blade. These slots may be sized only slightly larger than the saw blade, as with conventional cutting guides, so that the saw blade remains generally in the same orientation as the slot, even with slight transverse loading by the user on the saw blade. Other forms of cutting guides 38 and associated guide portions are also contemplated, such as those for receiving elongated, generally cylindrical, cutting tools, such as drills, burs, and reamers, curved slots for cutting a contoured surface, and the like. See, for example, the alternative cutting guide 38a with cylindrical guide portion 44a shown in FIG. 1. The robotic manipulator 22 may be capable of supporting the cutting guide 38 for movement in multiple degrees of freedom, e.g., two, three, four, five or six degrees of freedom.

The free-hand surgical instrument 42 is capable of being operated independently of the robotic arm 24 and the cutting guide 38. In one version, the free-hand surgical instrument 42 is a surgical saw having an oscillating saw blade used for creating planar cuts in tissue, such as bone. The free-hand surgical instrument 42 comprises a motor MT for oscillating or otherwise driving the cutting tool 40. The motor MT may be of any suitable type to operate the cutting tool 40, including, but not limited to, a pneumatic or electrical motor. The motor MT is configured, for instance, to provide oscillating motion to the cutting tool 40 (e.g., the saw blade) during the surgical procedure. An example of a such a free-hand surgical instrument 42 is disclosed in U.S. Pat. No. 7,704,254, entitled "Surgical Sagittal Saw with Indexing Head and Toolless Blade Coupling Assembly for Actuating an Oscillating Tip Saw Blade," which is hereby incorporated by reference herein in its entirety.

In versions in which the cutting tool 40 comprises a saw blade, the saw blade may be of any size, shape, or type (i.e. straight blade, crescent blade, etc.). The saw blade may comprise an attachment portion configured to be removably coupled to a hub of the free-hand surgical instrument 42. Opposite the attachment portion, the saw blade includes a cutting portion or working portion W which has a plurality of teeth. In some embodiments, the saw blade is formed from a single piece of material, such as metal, by stamping and/or machining. The saw blade may be configured to create a kerf with a generally flat face or may be configured to provide a kerf with a rounded profile. The saw blade may comprise a cartridge-style saw blade. The saw blade may be like that shown in U.S. Pat. No. 8,444,647, entitled "Surgical Sagittal Saw Blade with a Static Bar and a Pivoting Blade Head, the Bar Shaped to Facilitate Holding the Blade to a Complementary Saw," which is hereby incorporated herein by reference. Various configurations of saw blades or other cutting tools have been contemplated.

The navigation system 14 is set up to track movement of the cutting guide 38, the cutting tool 40, the patient's anatomy of interest, e.g., the femur F and tibia T, and/or other objects. The navigation system 14 tracks these objects for purposes of displaying their relative positions and orientations to the user and, in some cases, for purposes of controlling placement of the cutting guide 38 relative to virtual boundaries associated with the patient's anatomy, thereby also controlling placement of the cutting tool 40 relative to such virtual boundaries. To know the pose of the cutting guide 38, the navigation system 14 can utilize any combination or transformations or relationships between the various components of the navigation and/or robotic system. For example, either the cutting guide 38 itself and/or the robot (and any components thereof such as the base, links, arms) can be tracked to know the pose of the cutting guide 38 (and respective slots of the cutting guide). The robot can be tracked using navigation data and/or kinematic data derived from the positions of the joints. The cutting guide 38 pose can be determined solely from navigation data, solely from kinematic data, or from any combination of navigation data and kinematic data. Transformations can implicate any component of the navigation system, including any of the trackers described herein, as well as the patient and surgical table.

For any of the implementations described herein, the robotic manipulator 22 may be controlled to move in a manner that corresponds to patient movement such that the cutting guide 38 maintains a relative pose to the patient before and after the patient movement. The navigation system can measure a pose of the cutting guide 38 held by the robotic manipulator and a pose of a bone of the patient. The system controls the robotic manipulator to rigidly hold the cutting guide 38 in place, for example, to ensure the cutting guide 38 is aligned with an identified position, target, or plane. The system can determine a change in the pose of the bone and automatically adjust a pose of the cutting guide 38 based at least in part on the change in the pose of the bone. The change in bone position may result from different conditions, such as when an operator moves the patient limb or table. As such, a spatial relationship between the cutting guide 38 and the bone remains substantially unaltered as the operation is performed, thereby ensuring the cutting guide 38 remains as intended before patient movement.

The navigation system 14 includes a cart assembly 46 that houses a navigation controller 48. A user interface UI is in operative communication with the navigation controller 48. The user interface UI includes the displays 20 that are adjustably mounted to the cart assembly 46 and input devices, such as a keyboard and mouse, that can be used to input information into the navigation controller 48 or otherwise select/control certain aspects of the navigation controller 48. For example, the user interface UI may be configured to receive input from the user to adjust at least one of a position and orientation of the cutting guide 38 relative to the patient's tissue being treated. Other input devices are contemplated including a touch screen or voice-activation.

The localizer 16 communicates with the navigation controller 48. In the embodiment shown, the localizer 16 is an optical localizer and includes a camera unit. The camera unit has an outer casing that houses one or more optical position sensors S. In some embodiments at least two optical sensors S are employed, sometimes three or more. The optical sensors S may be separate charge-coupled devices (CCD). The camera unit is mounted on an adjustable arm to position the optical sensors S with a field of view of the below discussed tracking devices 18 that, ideally, is free from obstructions. In some embodiments the camera unit is adjustable in at least one degree of freedom by rotating about a rotational joint. In other embodiments, the camera unit is adjustable about two or more degrees of freedom. The camera unit may also include a central video camera 45 to generate video images of the surgical procedure or certain steps thereof.

The localizer 16 includes a localizer controller 50 in communication with the optical sensors S to receive signals from the optical sensors S. The localizer controller 50 communicates with the navigation controller 48 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors S communicate directly with the navigation controller 48. Position and orientation signals and/or data are transmitted to the navigation controller 48 for purposes of tracking the objects. The cart assembly 46, the displays 20, and the localizer 16 may be like those described in U.S. Pat. No. 7,725,162 to Malackowski, et al. issued on May 25, 2010, entitled "Surgery System," hereby incorporated herein by reference.

The navigation controller 48 may comprise one or more computers, or any other suitable form of controller. Navigation controller 48 has the displays 20, central processing unit (CPU) and/or other processors, memory (not shown), and storage (not shown). The processors can be any type of processor, microprocessor or multi-processor system. The navigation controller 48 is loaded with software. The software, for example, converts the signals received from the localizer 16 into data representative of the position and orientation of the objects being tracked. The navigation controller 48 may additionally or alternatively comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor.

Figure 2:
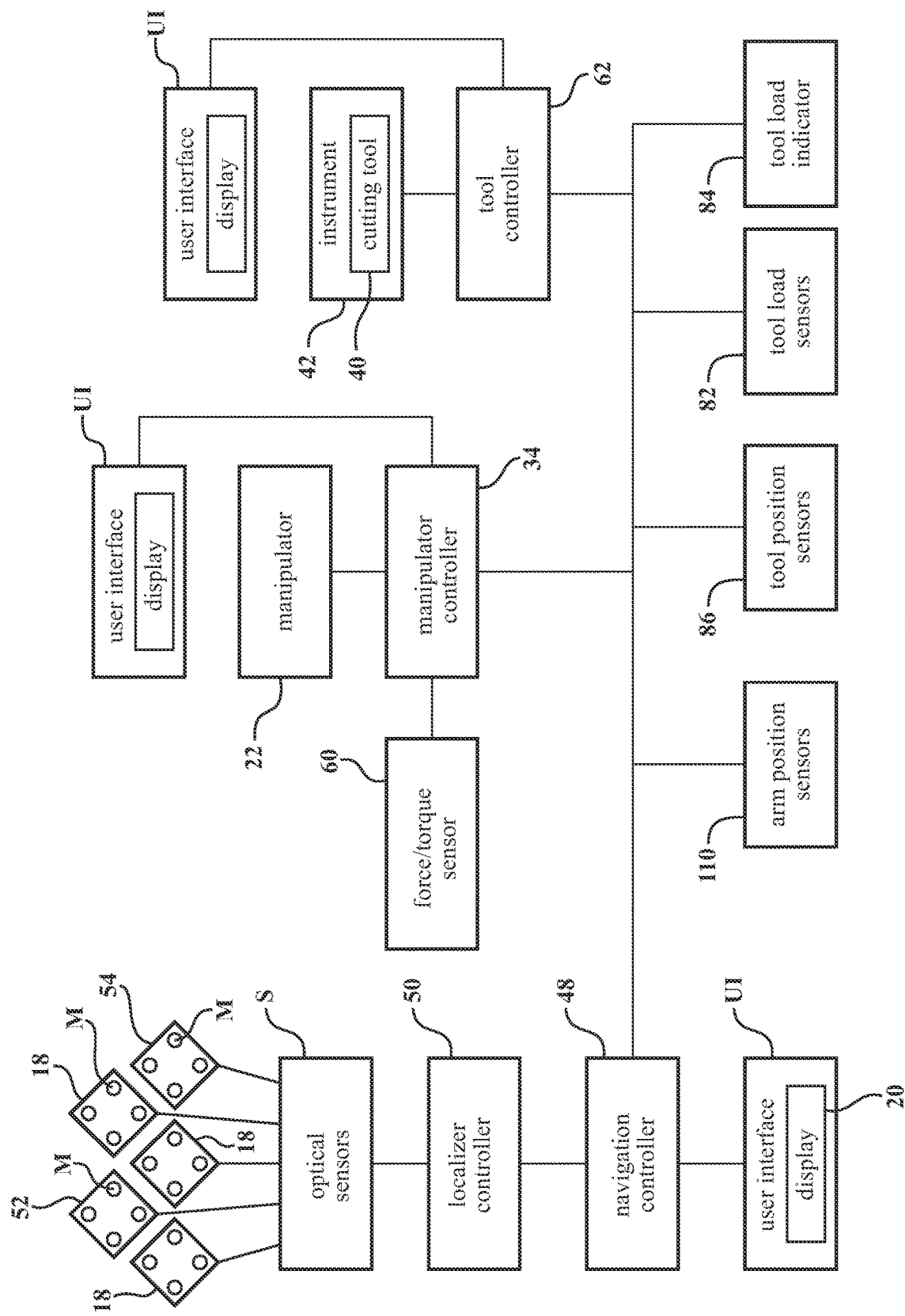
FIG. 2 is a schematic diagram of a control system of the robotic surgery system.

The navigation controller 48, the manipulator controller 34, and a below-described tool controller 62 are part of a control system of the robotic surgery system 10 shown in FIG. 2. The control system may comprise a single processor or multiple processors to carry out the functions of the navigation controller 48, the manipulator controller 34, and the tool controller 62. The control system may comprise any suitable configuration of input, output, and processing devices suitable for carrying out the functions and methods described herein. The control system may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

Navigation system 14 includes the plurality of tracking devices 18, also referred to herein as trackers. In the illustrated embodiment, the trackers 18 comprise anatomy trackers that are coupled to the patient, e.g., the femur F and tibia T, and tool trackers that are coupled to the end effector 36 and the free-hand surgical instrument 42 to track the cutting guide 38 and the cutting tool 40, respectively. The anatomy trackers may be firmly affixed to sections of bone via bone screws, bone pins, or the like. In other cases, clamps on the bone may be used to attach the anatomy trackers. For example, a lockable, articulating arm 49 (see FIG. 1) with clamp 51 may be coupled to the bone (e.g., by clamping around the patient's outer leg) to limit movement of the bone, and a tracker 18 may be attached to the clamp 51. In further embodiments, the anatomy trackers could be mounted to other tissue types or parts of the anatomy. The position of the anatomy trackers relative to the anatomy to which they are attached can be determined by registration techniques, such as point-based registration in which a digitizing probe P (e.g., navigation pointer) with its own tracker 18 is used to touch off on bony landmarks on the bone or to touch on several points on the bone for surface-based registration. Conventional registration techniques can be employed to correlate the pose of the anatomy trackers to the patient's anatomy, e.g., the bones being treated.

The tool trackers may be integrated with, fixed to, or removably coupled to the end effector 36, the cutting guide 38, the cutting tool 40, and/or the free-hand surgical instrument 42. The tool trackers are calibrated so that the locations of the tool trackers relative to the cutting guide 38 (or guide portions 44 thereof) and relative to the cutting tool 40 (or working end thereof) are known by the navigation system 14 for purposes of tracking a position and orientation of the cutting guide 38 and the cutting tool 40. More specifically, the position and orientation of the guide portions 44 of the cutting guide 38 and the position and orientation of the working end of the cutting tool 40 are capable of being tracked by virtue of the trackers 18. The working end of the cutting tool 40 may be, for example, a distal end of the cutting tool 40, such as teeth of the saw blade, tip of a drill, outer surface of a bur, bottom of a reamer, tip of a knife, RF tool tip, ultrasonic tool tip, or the like. Additionally or alternatively, a base tracker 52 and/or arm tracker 54 may also be coupled to the base 26 and/or one of the arm links 30 to track the position and orientation of the cutting guide 38, e.g., when combined with data derived from joint encoders in the joints of the robotic arm 24 that partially define the spatial transformation from the base 26 or the arm link 30 to the distal end 32 of the robotic arm 24, and when combined with data describing the location of the cutting guide 38 (or guide portions 44 thereof) with respect to the distal end 32.

In some embodiments, the trackers 18 may be passive trackers. In these embodiments, each tracker 18 has at least three passive tracking elements or markers for reflecting light from the localizer 16 back to the optical sensors S. In other embodiments, such as the one shown, the trackers 18 are active trackers and may have three, four, or more markers M, such as light emitting diodes (LEDs) transmitting light, such as infrared light to the optical sensors S. Based on the received optical signals, and by employing known triangulation techniques, the navigation controller 48 generates data indicating the relative positions and orientations of the trackers 18 relative to the localizer 16. It should be appreciated that the localizer 16 and trackers 18, although described above as utilizing optical tracking techniques, could alternatively, or additionally, utilize other tracking modalities to track the objects, such as electromagnetic tracking, radio frequency tracking, ultrasound tracking, inertial tracking, combinations thereof, and the like. Additionally, or alternatively, the navigation system 14 may employ fiber optics, machine vision, video cameras, or the like for purposes of identifying objects, determining positions, tracking movements, combinations thereof, or the like.

The navigation controller 48 generates image signals that indicate the relative position of the guide portions 44 of the cutting guide 38 and/or the working end of the cutting tool 40 to the tissue to be removed. These image signals are applied to the displays 20. The displays 20, based on these signals, generate images that allow the user and staff to view the relative position of the cutting guide 38 and/or the cutting tool 40 to the surgical site.

In the systems and methods described herein, virtual objects may be used to control (e.g., limit, constrain, prevent, etc.) movement, placement, or operation of the cutting guide 38 and/or the cutting tool 40 in a desired manner. These objects may be defined by points, lines, planes, volumes, or the like, and may be 1-D, 2-D, or 3-D. Such objects may be defined as models and could be solid models (e.g., built with constructive solid geometry, voxels, or the like), surface models (e.g., surface mesh, etc.), or any suitable form of 1-D, 2-D, or 3-D model. The virtual objects may be defined within virtual models of the anatomy of the patient 12 or may be defined separately from virtual models of the anatomy. The virtual objects may be registered pre-operatively or intraoperatively to images/models (e.g., CT scans, X-ray images, MRI images, 3-D models, etc.) of the patient's anatomy that are mapped to the patient's actual anatomy using well-known registration techniques. These virtual objects are stored in memory in the control system of the robotic surgery system 10 (e.g., in the navigation controller 48 and/or the manipulator controller 34). In some embodiments, the locations of the virtual objects described herein are mapped to the patient's anatomy to control movement or placement of the cutting guide 38 relative to the virtual objects and/or to control movement, placement, and/or operation of the cutting tool 40 in a manner that enables the robotic surgery system 10 to remove desired material from the patient 12. For example, as described further below, placement of the cutting guide 38 is controlled so that the cutting tool 40 stays within one or more virtual boundaries set by the user, which defines the tissue of the patient 12 to be removed by the cutting tool 40. Responses to virtual objects or boundaries can additionally or alternatively be any kind of haptic response such as, but not limited to: robot limited motions, sound feedback, vibration feedback, visual feedback, other types of feedback, and any combination thereof The robotic manipulator 22 has the ability to operate in one or more of: (1) a free mode in which a user grasps the end effector 36 in order to cause movement of the cutting guide 38 (e.g., directly; through force/torque sensor measurements on a force/torque sensor 60 that cause active driving of the robotic manipulator 22; passively; or otherwise); (2) a haptic mode in which the user grasps the end effector 36 of the robotic manipulator 22 to cause movement as in the free mode, but is restricted in movement by one or more virtual boundaries defined by one or more virtual objects stored in the robotic surgery system 10; (3) a semi-autonomous mode in which the cutting guide 38 is moved autonomously by the robotic manipulator 22 to a desired position and/or orientation and/or along a desired path (e.g., the active joints of the robotic arm 24 are operated to move the cutting guide 38 without requiring force/torque on the end effector 36 from the user); (4) a service mode in which the robotic manipulator 22 performs preprogrammed automated movements to enable servicing; or (5) other modes to facilitate preparation of the robotic manipulator 22 for use, e.g., for draping, etc. Examples of operation in the haptic mode and the semi-autonomous mode are described in U.S. Pat. No. 8,010,180, issued Aug. 30, 2011, entitled, "Haptic Guidance System and Method" and U.S. Pat. No. 9,119,655, issued Sep. 1, 2015, entitled, "Surgical Manipulator Capable of Controlling a Surgical Instrument in Multiple Modes," the entire disclosures of both of which are hereby incorporated by reference.

During operation in the haptic mode, the user manually manipulates (e.g., manually moves or manually causes the movement of) the robotic manipulator 22 to move the cutting guide 38 so as to ultimately place the cutting tool 40 in a desired position and/or orientation to perform the surgical procedure on the patient, such as for sawing, drilling, reaming, ablating, and the like. For example, the user may manually grasp the end effector 36 to manipulate the surgical manipulator 22 via feedback from the force/torque sensor 60, in the manner described in U.S. Pat. No. 9,119,655, hereby incorporated herein by reference.

As the user manipulates the robotic manipulator 22 to cause movement of the cutting guide 38, the navigation system 14 tracks the location of the cutting guide 38 relative to the anatomy of interest and provides haptic feedback (e.g., force feedback) to the user to limit the user's ability to manually manipulate (e.g., move or cause movement of) the cutting guide 38 beyond one or more predefined virtual boundaries that are registered (mapped) to the patient's anatomy, which results in highly accurate and repeatable positioning for sawing, drilling, reaming, ablating, etc. This haptic feedback helps to constrain or inhibit the user from manually manipulating the cutting guide 38 beyond the one or more predefined virtual boundaries associated with the surgical procedure. Virtual objects that define such virtual boundaries, which may also be referred to as haptic boundaries, are described, for example, in U.S. Pat. No. 8,010,180, which is hereby incorporated by reference herein in its entirety. Responses to virtual objects or boundaries can additionally or alternatively be any kind of haptic response such as, but not limited to: robot limited motions, sound feedback, vibration feedback, visual feedback, other types of feedback, and any combination thereof.

In one version, in the haptic mode, the manipulator controller 34 determines the desired location to which the cutting guide 38 should be moved based on forces and torques applied by the user on the end effector 36 and measured by the force/torque sensor 60. In this version, most users are physically unable to actually move the robotic manipulator 22 any appreciable amount to reach the desired position, but the robotic manipulator 22 emulates the user's desired positioning by sensing the applied forces and torques via the force/torque sensor 60 and reacting in a way that gives the user the impression that the user is actually moving the cutting guide 38 even though active motors on the joints are performing the movement. For example, based on the determination of the desired location to which the user wishes to move, and information relating to the current location (e.g., pose) of the cutting guide 38, the manipulator controller 34 determines the extent to which each of the plurality of links 30 needs to be moved in order to reposition the cutting guide 38 from the current location to the desired location. The data regarding where the plurality of links 30 are to be positioned is forwarded to joint motor controllers (not shown) (e.g., one for controlling each motor) that control the active joints of the robotic arm 24 to move the plurality of links 30 and thereby move the cutting guide 38 from the current location to the desired location.

The haptic mode may also be implemented in other ways, including providing reactive forces to the user based on manual positioning of the robotic manipulator 22, e.g., activating one or more joint motors in response to passive movement of one or more of the links 30 of the robotic manipulator 22 to position the cutting guide 38. Additionally, or alternatively, other passive devices may be employed to help control positioning of the cutting guide 38 by providing haptic feedback, with the position of such passive devices being controlled by the manipulator controller 34 or the navigation controller 48. Such passive devices could include springs, magnets, etc.

The control system may also be configured to switch operation of the robotic manipulator 22 from the haptic mode to the free mode in response to the one or more forces and torques measured by the force/torque sensor 60 exceeding a predetermined limit. See, for example, U.S. Pat. No. 9,119,655, hereby incorporated herein by reference.

In some embodiments, in the semi-autonomous mode, the robotic manipulator 22 acts autonomously based on predefined paths, predefined positions/orientations, and/or predefined movements to move the cutting guide 38. Such paths/positions/orientations/movements may be defined during the surgical procedure and/or before the surgical procedure. In some embodiments, the user provides input to control the robotic manipulator 22 in the semi-autonomous mode, such as through a pendant, to autonomously move the cutting guide 38 to a desired position and/or orientation or to follow a desired path/movement as described in U.S. Pat. No. 9,566,122, hereby incorporated by reference herein in its entirety.

A user interface UI may be used to interface with the manipulator controller 34 in the semi-autonomous mode and/or to switch between the free mode, haptic mode, semi-autonomous mode, service mode, and/or other modes. The user interface UI may comprise a separate controller and/or may provide input to the manipulator controller 34, the navigation controller 48, and/or the tool controller 62. The user interface UI may comprise various forms of input devices (e.g., switches, sensors, touchscreen, etc.) to transmit signals resulting from actuating inputs on the user interface UI to one or more of the controllers 34, 48, 62. When the user is ready to begin autonomous advancement of the cutting guide 38, in the semi-autonomous mode, for example, the user may actuate an associated input (e.g., depress a button) of the user interface UI (and may be required to hold down the button to continue autonomous operation). In some versions, based on the actuation of one or more inputs, a feed rate (e.g., velocity) of the cutting guide 38 when moving from one position/orientation to the next may be controlled.

Figure 3:
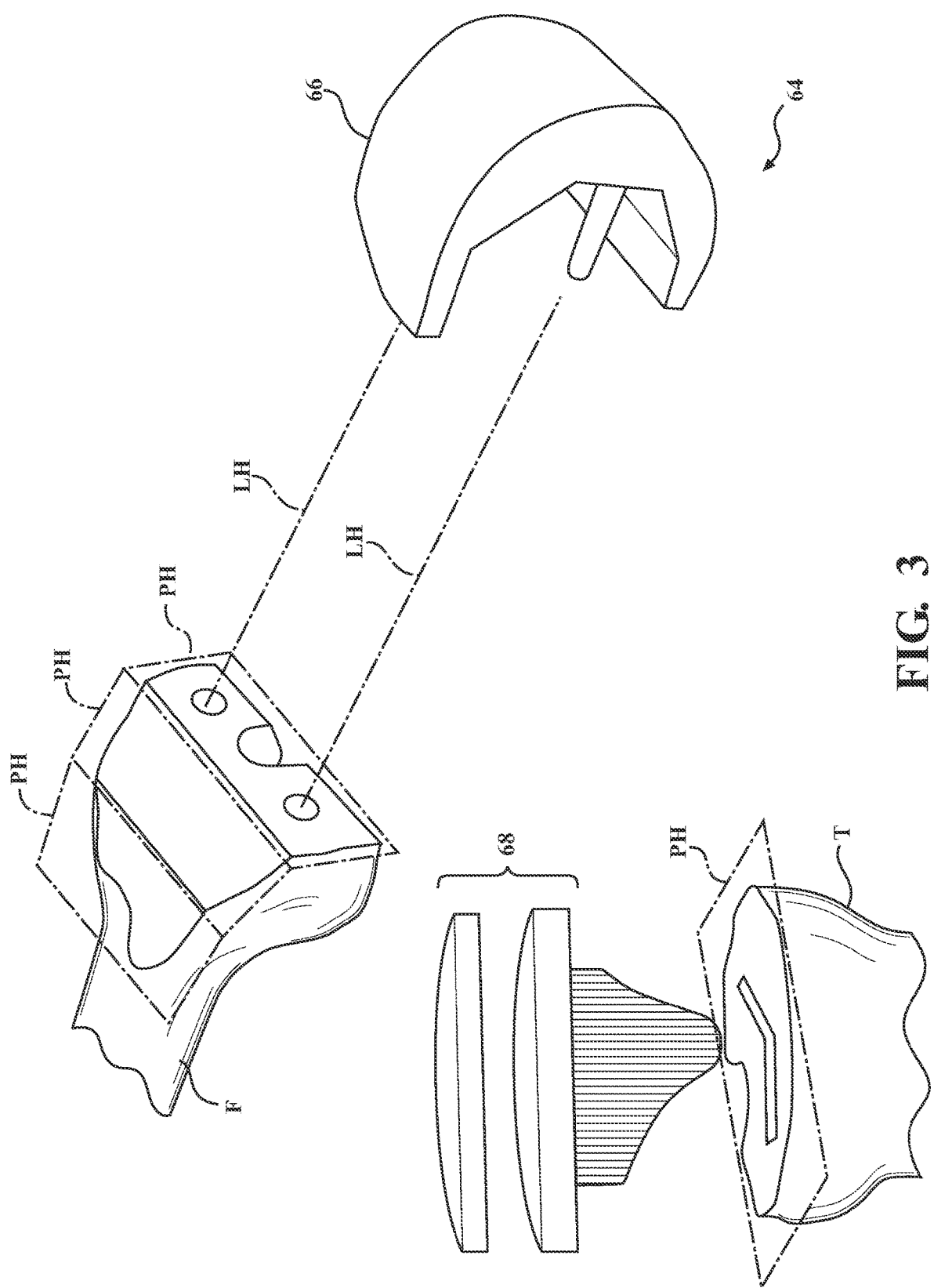
FIG. 3 is an exploded view of implant components in one exemplary implant system for a knee joint.

Referring to FIG. 3, pre-operative imaging and/or intra-operative imaging may be employed to visualize the patient's anatomy that requires treatment, such as the patient's knee joint, or other anatomy of the patient that requires treatment. For example, the user plans where to place a knee implant 64 comprising a femoral component 66 and a tibial component 68 with respect to the images and/or with respect to one or more 3-D models created from the images, such as 3-D models of the femur F and the tibia T created from CT scan data, MRI data, or the like. Such models may also be based on generic bone models morphed to resemble patient specific anatomy. Planning includes determining a pose of each implant component of the knee implant 64 with respect to the particular bone in which they are being placed, e.g., by identifying the desired pose of the implant component in the images and/or the appropriate 3-D model. This may include creating or positioning a separate 3-D model of the implant components with respect to the 3-D models of the patient's anatomy. Once the plan is set, then the plan is transferred to the robotic surgery system 10 for execution. The 3-D models may comprise mesh surfaces, constructive solid geometries (CSG), voxels, or may be represented using other 3-D modeling techniques.

Virtual objects can be created to control movement, placement, or operation of the robotic manipulator 22 and thereby control movement or placement of the cutting guide 38 so that the working end of the cutting tool 40 (e.g., saw, drill, bur, reamer, knife, RF tool, ultrasonic tool, etc.) is placed in a desired position and/or orientation. This may comprise ensuring during the surgical procedure that the cutting guide 38 and/or the cutting tool 40 stays in a desired position and/or orientation relative to a pre-defined virtual boundary delineating the bounds of the material to be removed to receive the implant. This may comprise, for example, ensuring during the surgical procedure that a trajectory of the cutting tool 40 (e.g., a bur or drill) is aligned with a desired pose of peg holes defined by virtual trajectories, that the trajectory of the cutting tool 40 (e.g., a bur or drill) is aligned with a desired pose of pilot holes for anchoring screws defined by virtual trajectories, and the like. This may further comprise ensuring that the cutting guide 38 and the cutting tool 40 (e.g., a sagittal saw blade) remain aligned with a desired resection/cutting plane defined by a virtual cutting plane and/or that the cutting guide 38 and/or the cutting tool 40 stay within a desired volume defined by a virtual guide volume or virtual tool volume. This may also comprise ensuring that the cutting guide 38 is suitably spaced from the tissue so that the cutting tool 40 is only able to penetrate the tissue up to a desired depth defined by a virtual depth stop.

The robotic surgery system 10 and/or the user may pre-operatively define the virtual objects associated with the desired cutting volume, trajectories, planar cuts, depths of cuts, etc. The desired cutting volumes may simply correspond to the geometry of the implants being used. Furthermore, these cutting volumes may be virtually defined and registered to the anatomy by virtue of the user planning the location of the implants relative to the 3-D models of the anatomy (e.g., the femur F and tibia T) and registering the 3-D models of the implants, along with the 3-D models of the anatomy to the actual anatomy during the procedure. Customized virtual boundaries may also be created based on patient-specific anatomy. In other words, instead of defining the cutting volume based on the geometry of the implant being used, the cutting volume is customized for the patient based on the geometry of the implant being used and the virtual model associated with the tissue of the patient 12. The navigation system 14 then tracks, via the trackers 18 associated with the cutting guide 38 and/or the cutting tool 40, a position and/or orientation of the cutting guide 38 and/or the cutting tool 40 relative to the customized virtual boundary. In this case, the control system (e.g., the manipulator controller 34, the navigation controller 48, and/or the tool controller 62) can control operation of the cutting tool 40 in response to interaction between the cutting tool 40 and the customized virtual boundary when the cutting tool 40 cooperates with the cutting guide 38 to cut the tissue. Creation and use of such a customized, patient-specific, virtual object is described in detail in U.S. Pat. Nos. 8,977,021 and 9,588,587, both of which are hereby incorporated herein by reference. Responses to virtual objects or boundaries can additionally or alternatively be any kind of haptic response such as, but not limited to: robot limited motions, sound feedback, vibration feedback, visual feedback, other types of feedback, and any combination thereof.

The robotic surgery system 10 and/or the user may also intra-operatively define the virtual objects associated with the desired cutting volume, trajectories, planar cuts, depths of cuts, etc., or may intra-operatively adjust the virtual objects that were defined pre-operatively. For example, in the free mode, the user could position the cutting guide 38 at a desired entry point relative to the anatomy of interest, e.g., the femur F, and orient the cutting guide 38 until the display 20 shows that the trajectory of the cutting guide 38 (e.g., a central axis thereof) is in a desired orientation. Once the user is satisfied with the trajectory, the user provides input to the robotic surgery system 10 to set this trajectory as the desired trajectory to be maintained during the procedure. The input could be provided via input devices such as the mouse, keyboard, touchscreen, push button, foot pedal, etc. coupled to the navigation controller 48 or the manipulator controller 34. This same procedure can be followed for the user to set a desired planar cut, etc. Virtual 1-D, 2-D, or 3-D models of the virtual objects defining the cutting volumes, desired trajectories, desired planar cuts, etc. are stored in memory for retrieval during the surgical procedure.

One or more virtual objects used by the robotic surgery system 10 could be defined by the navigation pointer P by touching anatomy of interest with the navigation pointer P and capturing associated points on the anatomy with the navigation system 14. For example, the navigation pointer P (FIG. 1) could be used to outline a virtual boundary. Additionally, or alternatively, the navigation pointer P could be used to delineate soft tissue or other sensitive anatomical structures to be avoided by the cutting tool 40. These points, for example, could be loaded into the robotic surgery system 10 to adjust the position/orientation of the cutting guide 38 so that the cutting tool 40 avoids these areas. Other methods could be used to delineate and/or define anatomy of interest, e.g., as being anatomy to be removed, anatomy to be avoided, etc.

FIG. 3 shows a plurality of virtual objects that may be employed by the robotic surgery system 10 so that one or more of the cutting tools 40 remove/treat tissue in a desired manner. These virtual objects, for example, enable the robotic surgery system 10 to: (1) provide a visual indication of the position and/or orientation of the cutting guide 38 and/or cutting tool 40 relative to desired positions and/or orientations; (2) provide haptic feedback to a user to provide a tactile indication of the position and/or orientation of the cutting guide 38 relative to the desired positions and/or orientations; and/or (3) guide autonomous movement of the cutting guide 38. For instance, line haptic objects LH may be created and stored in the robotic surgery system 10 to constrain movement of the cutting guide 38a to stay along desired trajectories. Planar haptic objects PH may be created for constraining movement of the cutting guide 38 to stay along desired cutting planes. Although the planar haptic objects PH are shown without any thickness, they may also be volumetric with a thickness generally corresponding to the thickness of the cutting tool 40 and/or guide portion 44. Other virtual object shapes, sizes, etc. are also contemplated. It should also be appreciated that other forms of virtual objects, other than haptic objects, could be employed to establish boundaries for the cutting guide 38 and/or the cutting tool 40, wherein such boundaries may be represented on one or more of the displays 20 to show the user when the guide portion(s) of the cutting guide 38 and/or the working end of the cutting tool 40 are approaching, reaching, and/or exceeding such boundaries.

Figure 4A:
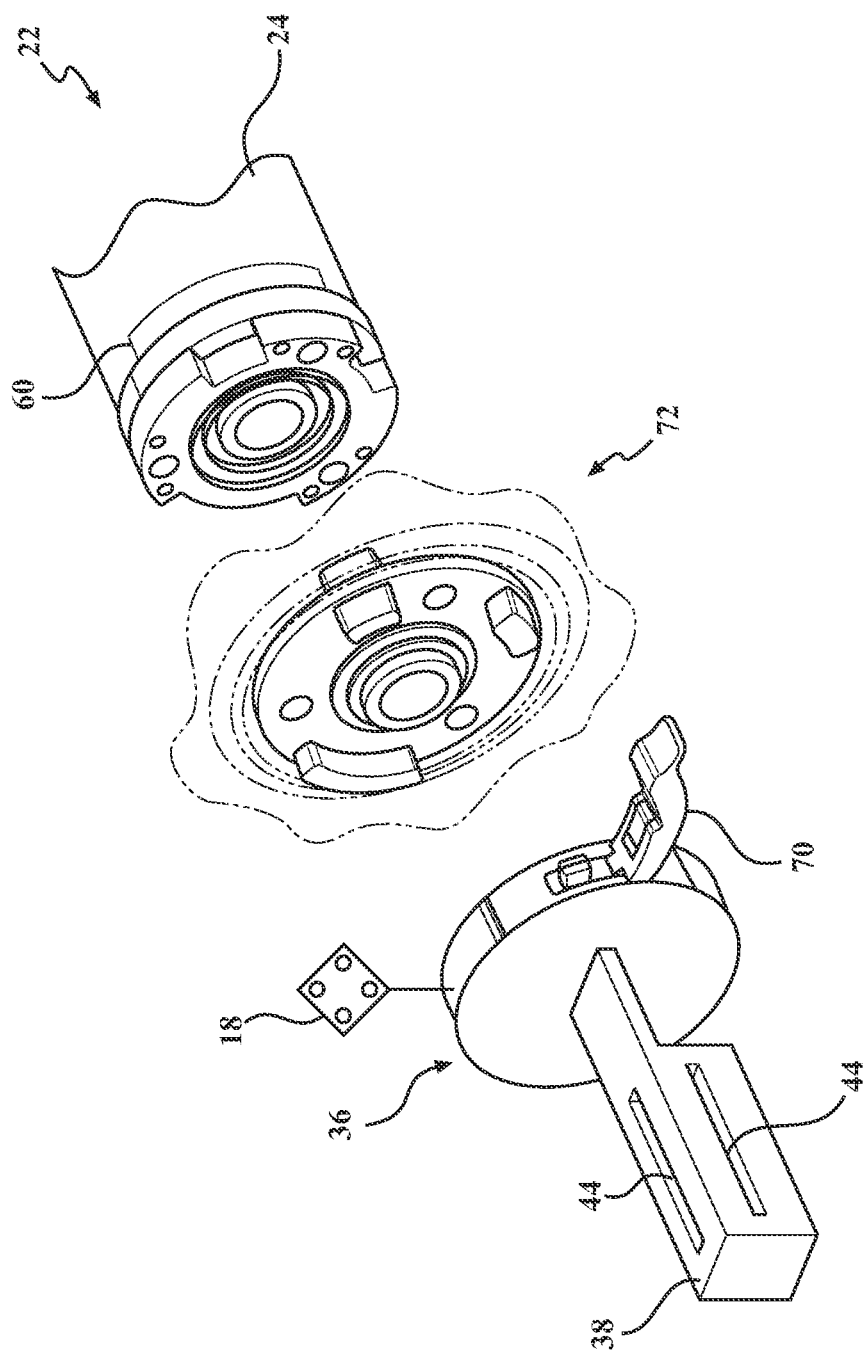
FIG. 4A is a perspective exploded view showing a cutting guide assembly onto a robotic arm through a sterile barrier.
Figure 4B:
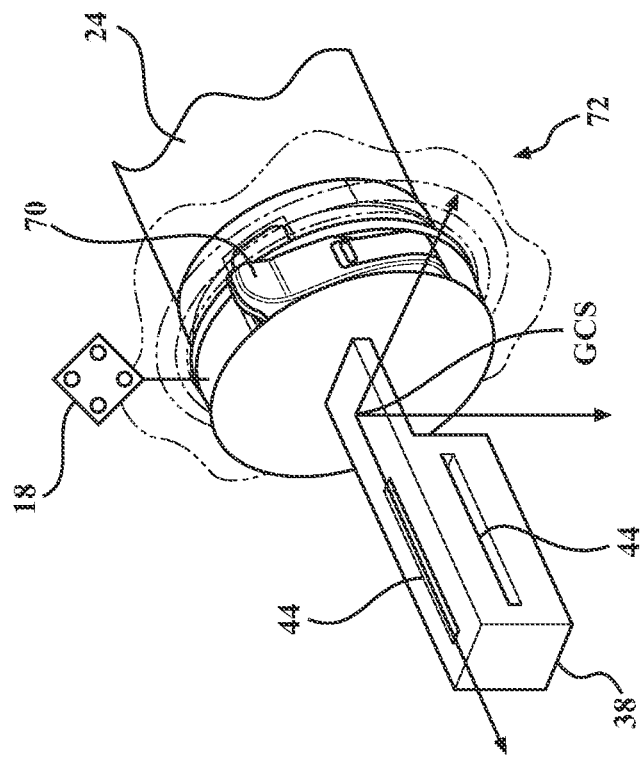
FIG. 4B is an assembled view of the cutting guide onto the robotic arm through the sterile barrier.
Figure 4B:
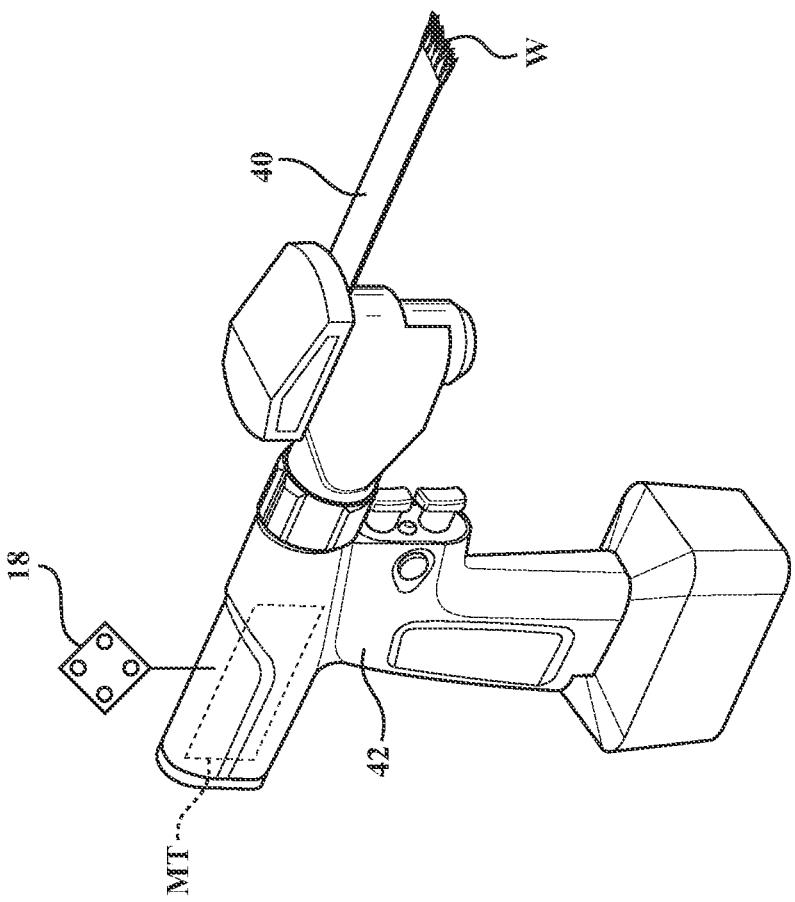

In operation, referring to FIGS. 4A and 4B, the cutting guide 38 is first coupled to the robotic manipulator 22. In some cases, to maintain sterility when switching between different end effectors on the robotic arm 24, a sterile barrier 72 may be located between the end effector 36 and the robotic arm 24. A lever 70 may be used to clamp the end effector 36 onto the robotic arm 24 in the manner described in U.S. Patent Application Publication No. 2016/0242861, filed on Feb. 19, 2016, entitled "Sterile Barrier Assembly, Mounting System, and Method for Coupling Surgical Components," which is hereby incorporated herein by reference in its entirety. Once the cutting guide 38 is secured to the robotic manipulator 22, then the cutting guide 38 can be used to receive the cutting tool 40 and guide movement thereof.

FIGS. 5A through 5F illustrate a sequence of movements and placements of the cutting guide 38 with respect to a desired cutting plane 74, which is defined in the control system as a virtual cutting plane. In some procedures, such as during a total knee procedure, several cuts are made to the tissue, and any of these cuts may employ the methods described herein. In some embodiments, cutting may be completely through the tissue or only partially through the tissue such that the cut is finished when a pre-determined final depth is reached. The cutting plane 74 may be defined pre-operatively by the user, such as by defining the desired planar cut on a virtual 3-D model of the tissue created using pre-operative images taken of the tissue. The desired planar cut may also be defined by the shape of the implant component and a 3-D model of the implant component. The cutting plane 74 may be defined intraoperatively by the user, or automatically by the control system. A position and orientation of the cutting plane 74 may be tracked by the navigation system 14 as the tissue moves during the surgical procedure by virtue of the tracker 18 attached to the tissue and registration of the tracker 18 to the tissue. The location of the cutting plane 74 may be tracked by virtue of being mapped to the 3-D model that includes the cutting plane 74. The robotic manipulator 22 can accommodate movement of the cutting plane 74 and autonomously adjust its own positioning as needed to maintain any desired relationship to the tissue, such as staying on the cutting plane 74 with respect to the tissue when necessary. Such control may be accomplished using the robotic controls described, for example, in U.S. Pat. Nos. 8,010,180, 9,119,655, or U.S. Patent Application Pub. No. 2014/0180290, all of which are hereby incorporated herein by reference.

The control system is configured to control movement and placement of the cutting guide 38 via the robotic manipulator 22. When the cutting guide 38 is coupled to the robotic manipulator 22, and the user is ready to move/place the cutting guide 38 so that the guide portion 44 is located to receive the cutting tool 40 on the desired cutting plane 74, the control system will send a command to the robotic arm 24 to control the joint motors thereof to move the cutting guide 38 so that the cutting tool 40, when placed into cooperation with the cutting guide 38 (e.g., placed into the guide slot of the cutting guide 38), is located on (e.g., aligned with) the cutting plane 74. The user may be able to operate the robotic surgery system 10 to autonomously position the cutting guide 38 so that the cutting tool 40 is automatically aligned with the cutting plane 74 in the desired position and/or orientation in the manner described in U.S. Patent Application Pub. No. 2014/0180290, which is incorporated herein by reference. The cutting tool 40 is aligned with the cutting plane 74 by being in the same general orientation as the cutting plane 74 with the cutting plane 74 passing through or being adjacent to the cutting tool 40. In some steps, the user may position the cutting guide 38 at the desired position and/or orientation by virtue of haptic guidance as described herein.

The robotic surgery system 10, by virtue of the navigation system 14 and associated trackers 18, 52, 54, and/or by virtue of the encoders in the joints of the robotic arm 24, is able to determine the position and orientation of the cutting guide 38 with respect to the cutting plane 74 to locate the cutting tool 40 as required. A current position/orientation of the cutting guide 38 and/or the cutting tool 40 and/or the desired position/orientation of the cutting guide 38 and/or the cutting tool 40 relative to the patient's anatomy may be represented on the display 20 and updated in real-time so that the user is able to visualize when the cutting guide 38 and/or the cutting tool 40 is in the desired position/orientation (e.g. on the cutting plane 74).

Figure 5A:
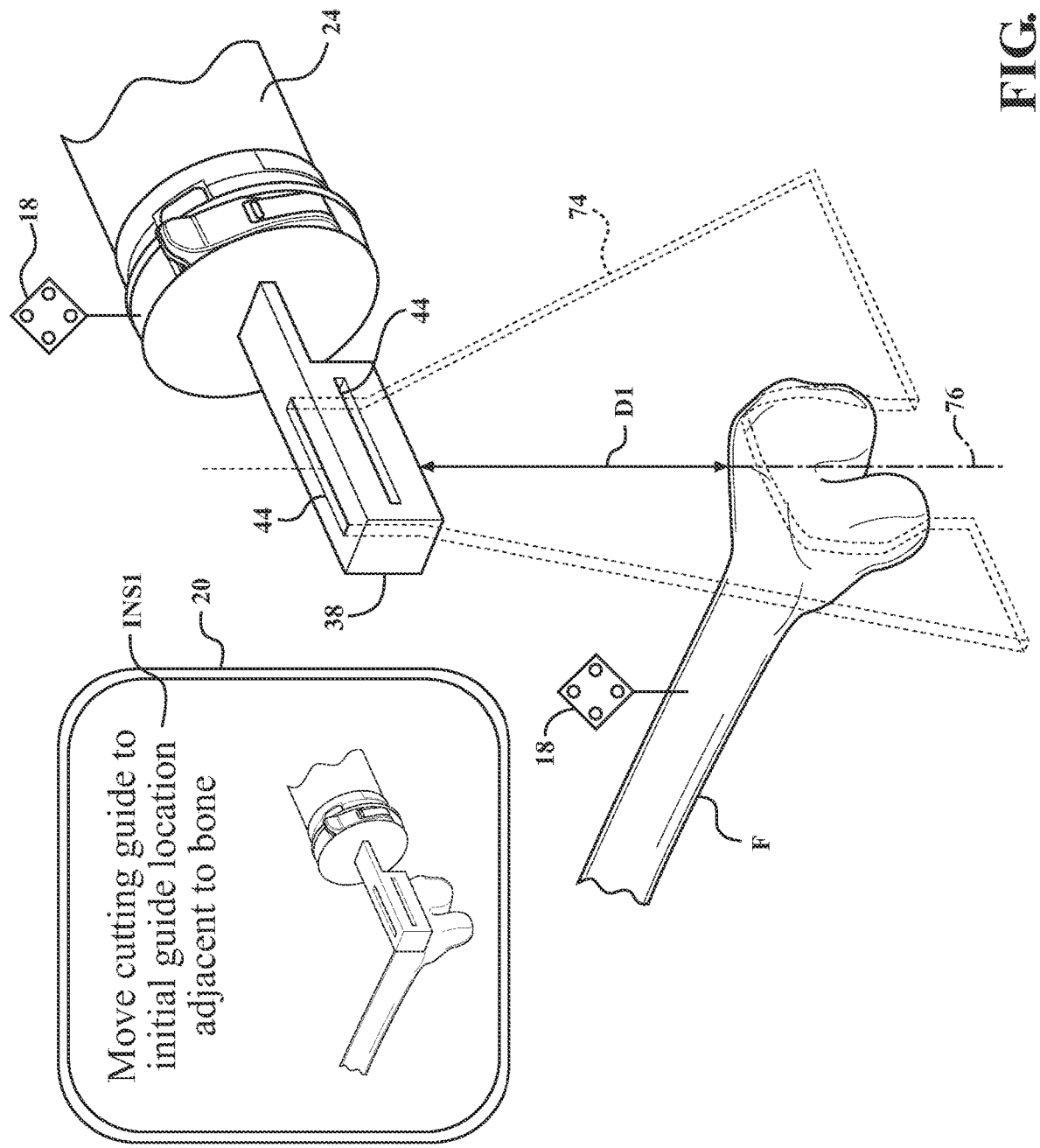

In FIG. 5A, the cutting plane 74 is shown disposed transverse to an outer surface of tissue, such as bone. Here, the control system has autonomously positioned the cutting guide 38 at an initial target position and/or orientation relative to the tissue so that the cutting tool 40 aligns with the desired cutting plane 74 when the cutting tool 40 is positioned into cooperation with the guide portion 44 of the cutting guide 38. The control system may operate the robotic manipulator 22 to autonomously position the cutting guide 38 at the initial target position and/or orientation at a starting distance D1 spaced from the tissue so that the cutting tool 40 is unable to contact the tissue through the cutting guide 38. The starting distance D1 may be defined as a distance from a center of the guide portion 44 (e.g., center of the slot on an underside of the cutting guide 38) to the closest surface of the tissue in the cutting plane 74. The starting distance D1 may also be defined in other ways.

Since the outer surface of the tissue is arcuate or curved and the cutting plane 74 usually extends non-perpendicularly from the outer surface, merely moving the cutting guide 38 closer to the tissue without being adjacent and/or abutting the tissue, could result in skiving of the cutting tool 40 along the curved outer surface. To this end, referring to FIG. 5B, the cutting guide 38 is first located at an initial guide location GL1 adjacent to the tissue to limit such skiving. In the initial guide location GL1, the cutting guide 38 is placed adjacent to the tissue, and may be abutting the tissue. The initial guide location GL1 may be determined by the navigation controller 48 based on data from the navigation system 14. The initial guide location GL1 may be a position and orientation of a guide coordinate system GCS of the cutting guide 38 in a localizer coordinate system LCLZ of the localizer 16, which may act as a common coordinate system for purposes of tracking the relative positions and orientations of the various objects during the surgical procedure (other coordinate systems could be used as the common coordinate system to which the objects are transformed using conventional coordinate transformation techniques). The initial guide location GL1 may thus be determined as a location of the cutting guide 38 in which a surface of the cutting guide 38 is adjacent to the tissue—the tissue also being tracked in the localizer coordinate system LCLZ, when the cutting guide 38 is in the target orientation.

The control system may autonomously operate the robotic manipulator 22 to move the cutting guide 38 to the initial guide location GL1 or may control manual manipulation of the robotic manipulator 22 to move the cutting guide 38, such as in the haptic mode. In the haptic mode, the control system prevents the user from moving the cutting guide 38 off the target orientation (e.g., off the desired plane 74), while allowing the user to move the cutting guide 38 into any desired position in the target orientation via one or more virtual objects, such as a virtual planar boundary. More specifically, the control system constrains movement of the cutting guide 38 as the user manually manipulates the end effector 36 to cause the cutting guide 38 to move toward the bone to the initial guide location GL1 adjacent to the tissue such that the cutting guide 38 remains in the target orientation at the initial guide location GL1. To this end, the control system may generate instructions INS1 on the display 20 (see FIG. 5A) to instruct the user to move the cutting guide 38. While the instructions described herein refer to visual instructions generated by the control system on the display 20, such instructions, and any other instructions described herein, may also be audible instructions or tactile instructions.

Figure 5B:
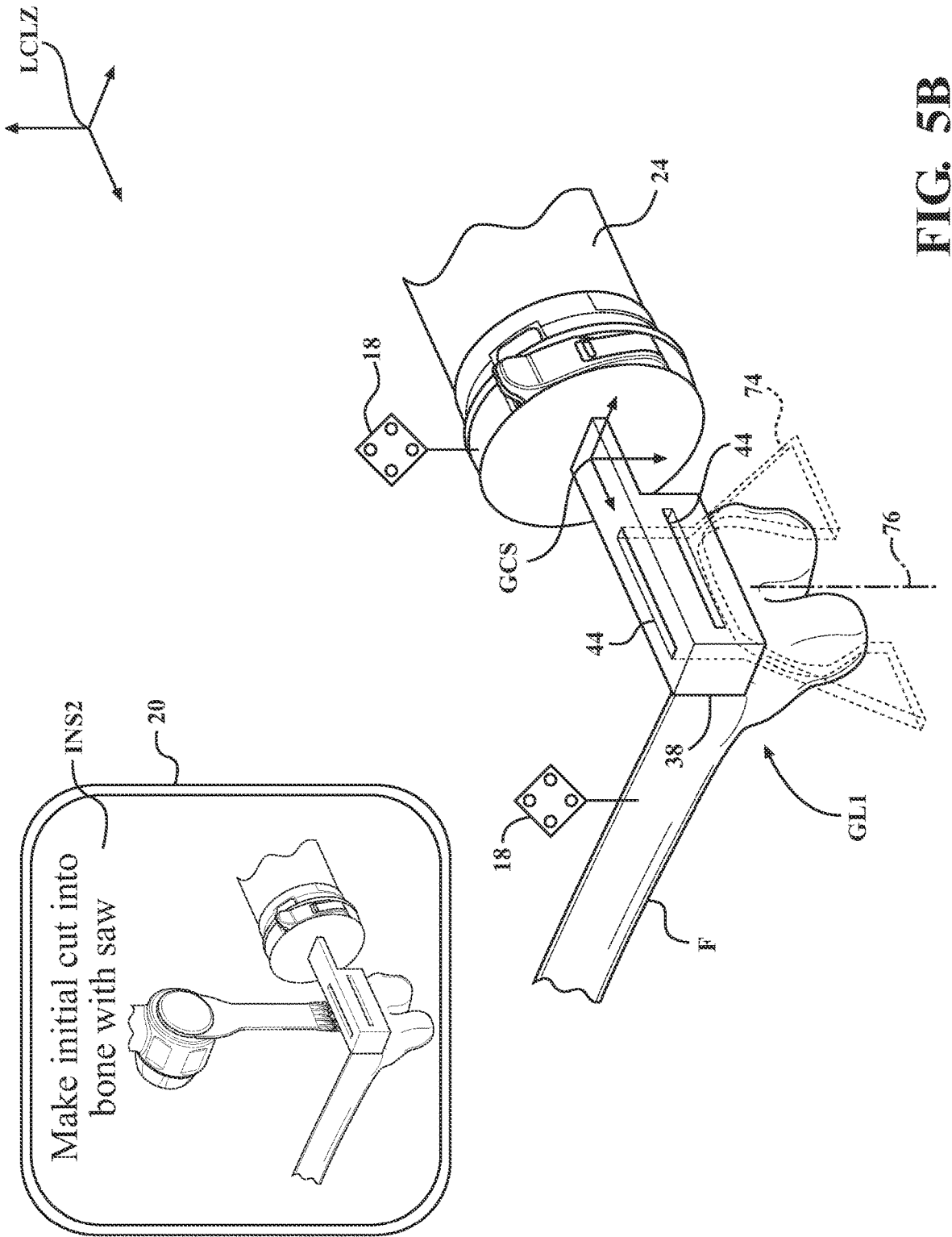

In some cases, the control system may constrain movement of the cutting guide 38 such that the cutting guide 38 is only able to be translated from the initial target position/orientation to the initial guide location GL1 along a desired trajectory 76 while staying in the same target orientation (compare FIGS. 5A and 5B). In this case, another virtual boundary, such as a virtual line, may be activated to define the desired trajectory 76. Accordingly, the user may be unable to reorient the cutting guide 38, and can only move the cutting guide 38 in a single direction toward the femur F, for example, along the desired trajectory 76. In some versions, the initial guide location of the cutting guide 38 may be adjacent to the tissue, but not necessarily aligned with the desired trajectory 76 or target orientation. Instead, the initial guide location may be defined at an orientation that results in the cutting tool 40 being disposed normal to the tissue to further limit potential skiving effects (e.g., deflection). The navigation system 14 could monitor a depth of the cutting tool 40 once cutting is initiated, and thereafter automatically align the cutting guide 38 to the desired trajectory/orientation once a specified penetration depth into the tissue has been achieved.

Referring to FIGS. 5B through 5E, the control system operates the robotic manipulator 22 to effectively lock the cutting guide 38 at the initial guide location GL1 with respect to the tissue such that the user is able to make an initial cut with the cutting tool 40 along the desired cutting plane 74 while the cutting guide 38 is located adjacent to the tissue. This helps to prevent skiving of the cutting tool 40. Once at the desired position/orientation relative to the tissue and locked, the user may use the cutting tool 40 to make the initial cut into the tissue. This may comprise inserting the cutting tool 40 into the guide portion 44 of the cutting guide 38 and initiating operation of the surgical instrument 42 via a separate user interface UI (see FIG. 2). Alternatively, the control system may automatically operate the motor MT of the surgical instrument 42 to start oscillating the cutting tool 40 to begin the initial cut to the outer surface of the tissue. Cutting may also be in response to user input (e.g., a trigger). The control system may control operation of the motor MT to facilitate cutting and/or to deactivate cutting, such as when the cutting tool 40 meets or exceeds a virtual boundary.

Figure 5C:
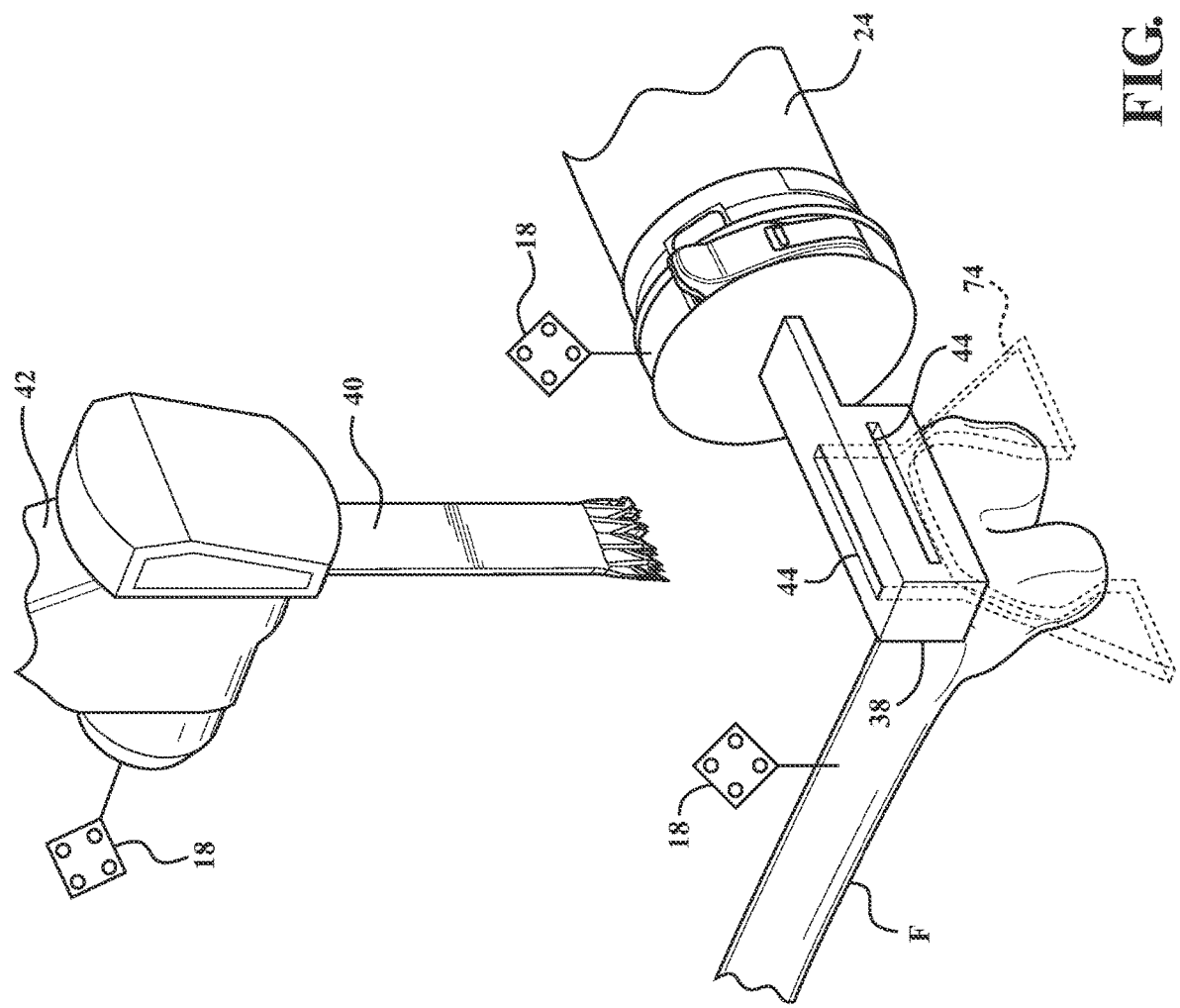
Figure 5D:
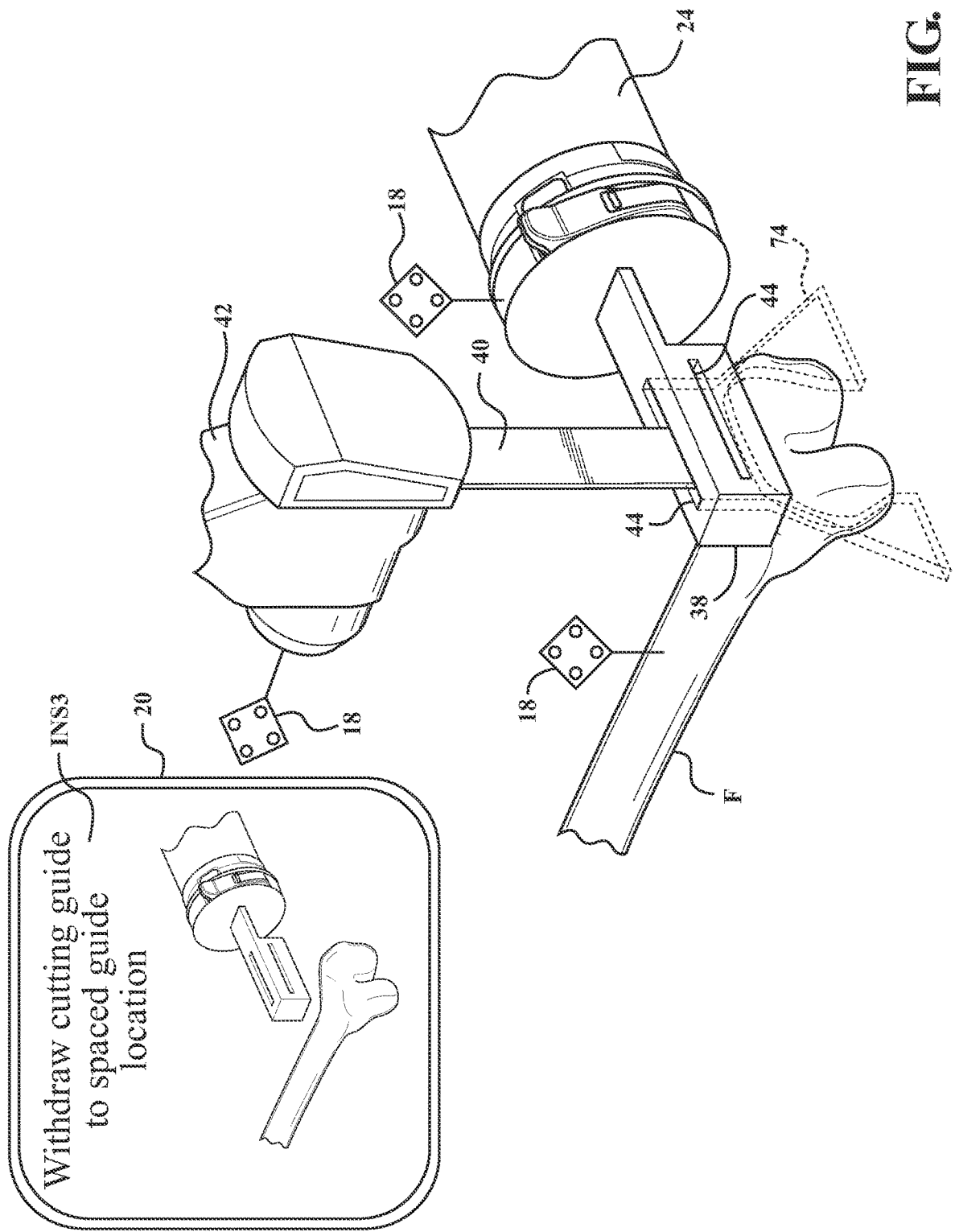

Once the motor MT is operating, referring to FIGS. 5D and 5E, the cutting tool 40 is then moved along the cutting plane 74 toward the tissue to form the initial cut into the tissue, such as a notch 80 (see FIG. 5E). One or more virtual boundaries (e.g., a virtual stop) may be activated to prevent the user from cutting beyond the initial notch 80 that is needed (e.g., the virtual boundary may be a limit in depth along the cutting plane 74). For example, a virtual boundary (e.g., virtual plane) with a lateral width only slightly larger than the cutting tool 40 (to accommodate for oscillations) and a depth at the desired depth of the initial notch 80 may be programmed into the control system so that any attempt by the user to move the cutting tool 40 deeper than the initial notch 80 in a free hand manner results in the tool controller 62 deactivating the motor MT or otherwise controlling the cutting tool 40 so that the cutting tool 40 is unable to penetrate any further into the tissue.

Once the predetermined depth is reached and the initial notch 80 is formed, the cutting tool 40 is withdrawn from the cutting guide 38 and the cutting guide is moved to a spaced guide location GL2 (FIG. 5E). The control system facilitates withdrawal of the cutting guide 38 away from the initial guide location GL1 to the spaced guide location GL2 after the user makes the initial cut in the tissue with the cutting tool 40 along the desired cutting plane 74. The cutting guide 38 remains in the target orientation at the spaced guide location GL2 and the spaced guide location GL2 is suitable for the cutting tool 40 to continue cutting the tissue along the desired cutting plane 74. In one version, the control system facilitates withdrawal by operating the robotic manipulator 22 to autonomously withdraw the cutting guide 38 away from the tissue and move the cutting guide 38 from the initial guide location GL1 to the spaced guide location GL2. Additionally or alternatively, the control system generates instructions INS2 on the display 20 (FIG. 5B) for the user to make the initial cut in the tissue with the cutting tool 40 while the cutting guide 38 is at the initial guide location GL1 and generates instructions INS3 for the user to withdraw the cutting guide 38 away from the tissue after the initial cut is made. In this case, the control system operates the robotic manipulator 22 to constrain movement of the cutting guide 38, such as via haptic feedback in the haptic mode, as the user manually manipulates the end effector 36 to withdraw the cutting guide 38 away from the tissue after the initial cut is made.

The spaced guide location GL2 may be defined by a virtual object, such as another virtual stop defined in the desired cutting plane 74 and along the desired trajectory 76. The spaced guide location GL2 may also be determined based on one or more parameters associated with the cutting tool 40 such that the spaced guide location GL2 is different for different cutting tools 40. The one or more parameters include at least one of: a length of the cutting tool 40; a width of the cutting tool 40; a maximum depth the cutting tool 40 can cut into the tissue through the cutting guide 38; and a tracked position of the cutting tool 40. As shown on the display 20 in FIG. 5E, the navigation system 14 generates a visual representation of a region R1 of the area capable of being reached by the cutting tool 40 when the cutting guide 38 is in the spaced guide location GL2. This can be helpful to understand the reach of the cutting tool 40 and to visualize where the cutting tool 40 may be capable of making contact with delicate structures that are not intended to be cut. The spaced guide location GL2 may also be a position and orientation of the guide coordinate system GCS of the cutting guide 38 in the localizer coordinate system LCLZ.

Once the cutting guide 38 has been moved to the spaced guide location GL2, then the user is able to finish making the planar cut to the tissue along the desired cutting plane 74. See also the instructions INS4 in FIG. 5E. FIG. 5F shows the finished planar surface FPS of the tissue after resection using the cutting tool 40 has been completed.

Figure 6A:
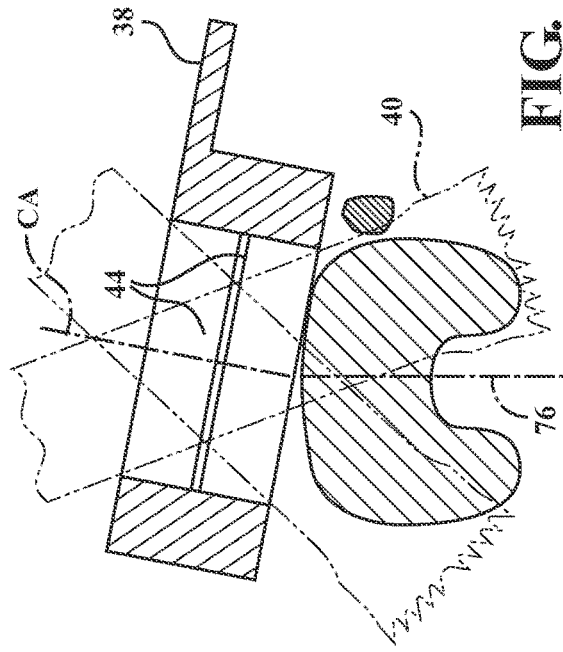
FIGS. 6A and 6B illustrate a first cutting region capable of being reached by the cutting tool when the cutting guide is in a first orientation.
Figure 6B:
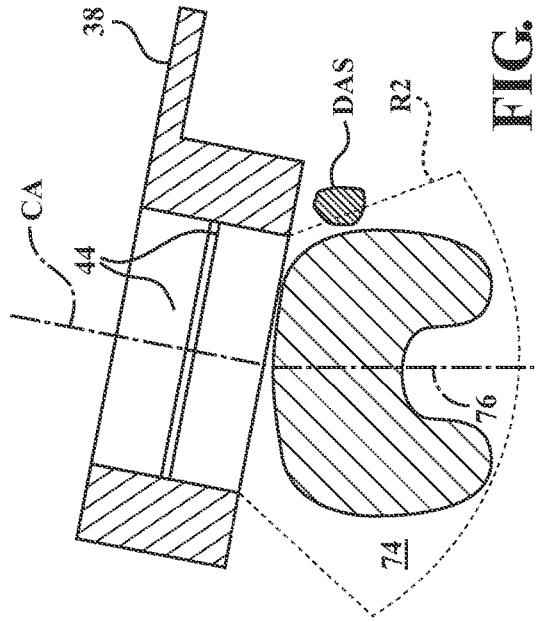
Figure 7A:
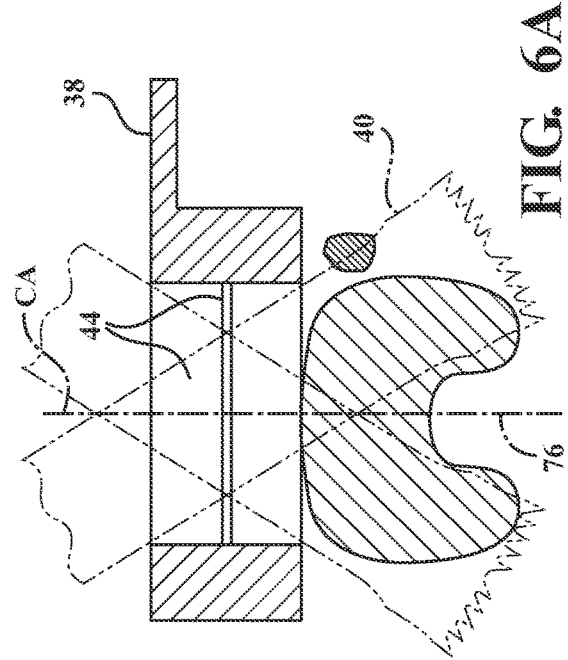
FIGS. 7A and 7B illustrate a second cutting region capable of being reached by the cutting tool when the cutting guide is in a second orientation, different than the first orientation, but in the same cutting plane as the first orientation.
Figure 7B:
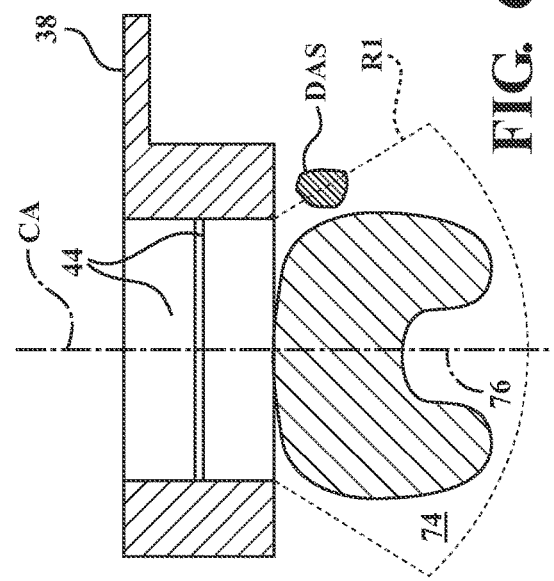
Figure 8A:
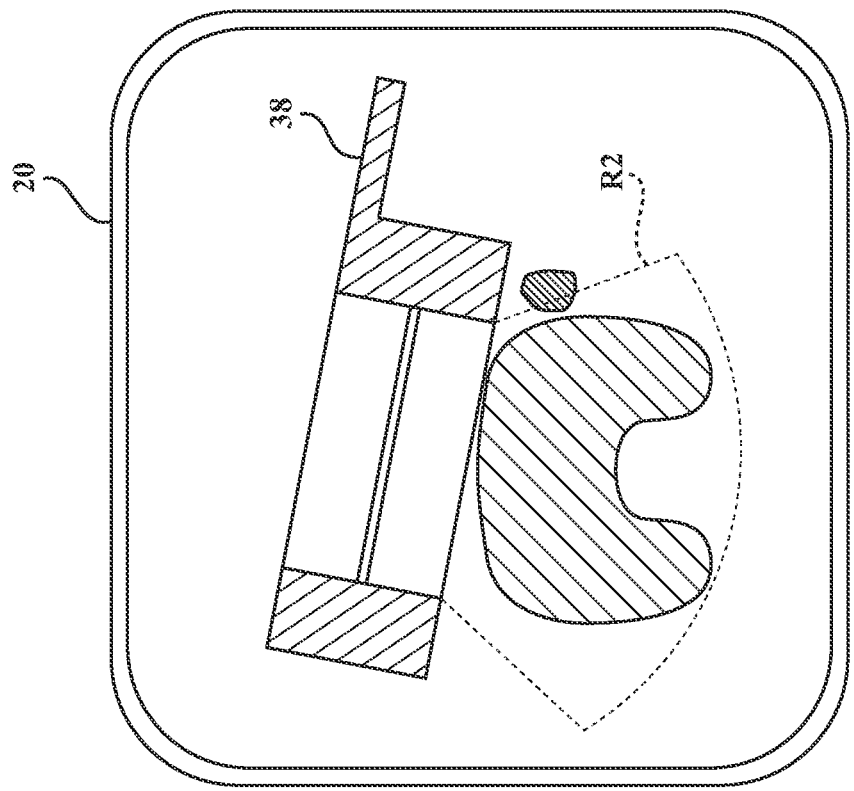
FIGS. 8A and 8B illustrate screen shots of a display screen showing the first and second cutting regions.
Figure 8B:
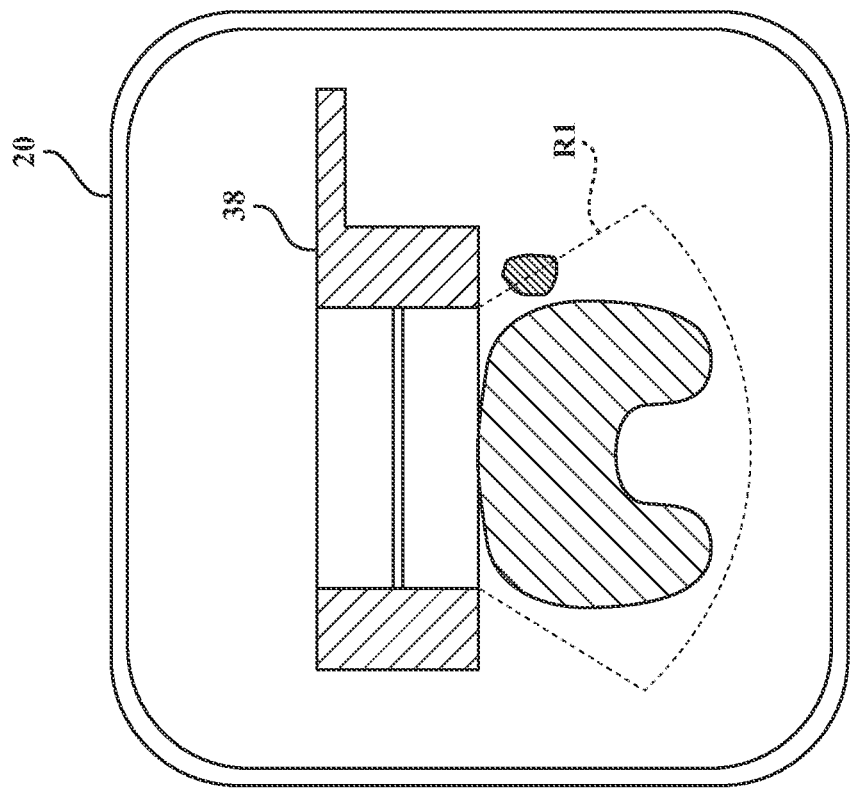

Referring to FIGS. 6A through 8B, it may be desirable for the cutting guide 38 to be placed at a different orientation with respect to the desired trajectory 76, while remaining on the target orientation aligned with the desired cutting plane 74. Such reorientation of the cutting guide 38 alters the reach of the cutting tool 40. Thus, the region of tissue that can be cut by the cutting tool 40 changes. For example, as illustrated in FIG. 6A, when a central axis CA of the cutting guide 38 is oriented in line with the desired trajectory 76 (representing a first guide angle relative to the tissue), then the cutting tool 40, limited by physical constraints/interference of the cutting guide 38 and the free-hand surgical instrument 42, is able to reach the first area/region R1 in the desired cutting plane 74 (see FIG. 6B). Accordingly, a delicate anatomical structure DAS (e.g., ligament, tendon, nerve, etc.), which is located in the first region R1 could be inadvertently cut with the cutting tool 40. However, if the cutting guide 38 is reoriented such that its central axis CA is at an acute angle with respect to the desired trajectory 76 (representing a second guide angle relative to the tissue), as shown in FIG. 7A, then a second area/region R2 is accessible by the cutting tool 40 wherein the delicate anatomical structure DAS is outside the second region R2 and unable to be reached by the cutting tool 40 (compare FIGS. 6B and 7B). The robotic manipulator 22 is controlled so that the cutting guide 38 is reoriented in a manner in which the cutting tool 40 remains aligned with the desired cutting plane 74. As shown in FIGS. 8A and 8B, the control system is configured to change the visual representation of the regions R1, R2 capable of being reached by the cutting tool 40 as the cutting guide 38 is reoriented so that the user is able to visualize how reorientation of the cutting guide 38 affects potential tissue in the desired cutting plane 74.

Figure 8C:
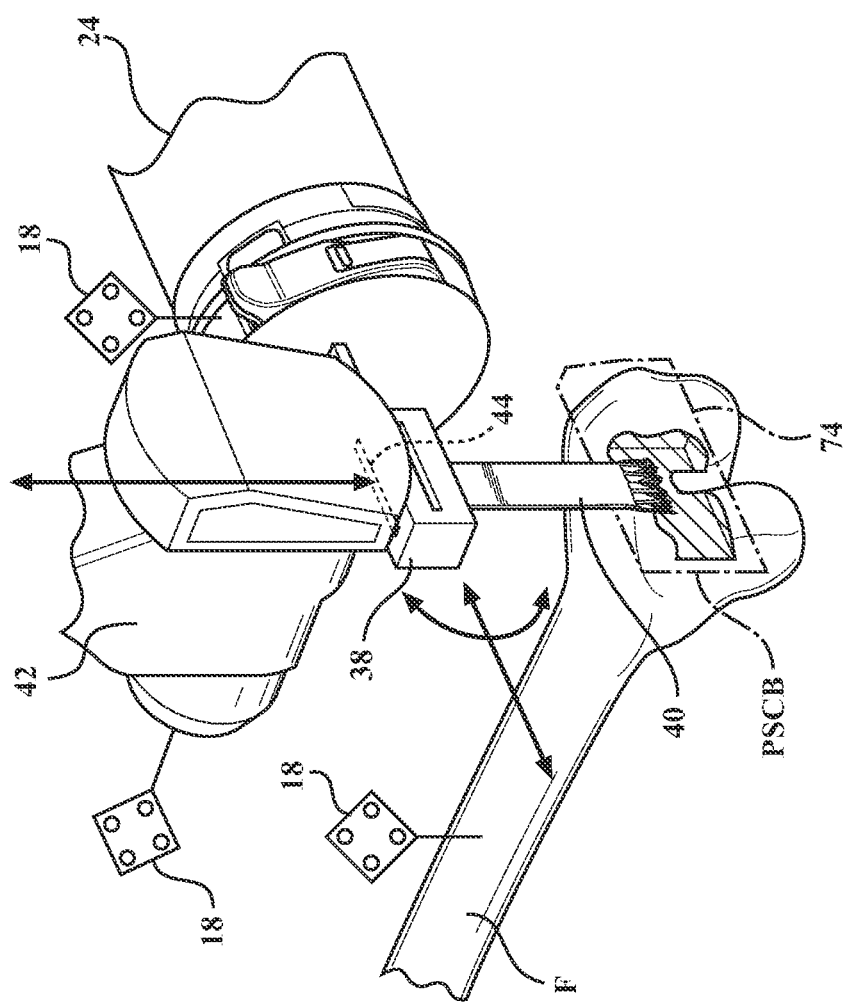
FIGS. 8C through 8E illustrate cutting of a bone along a cutting plane having a patient-specific cutting boundary.
Figure 8D:
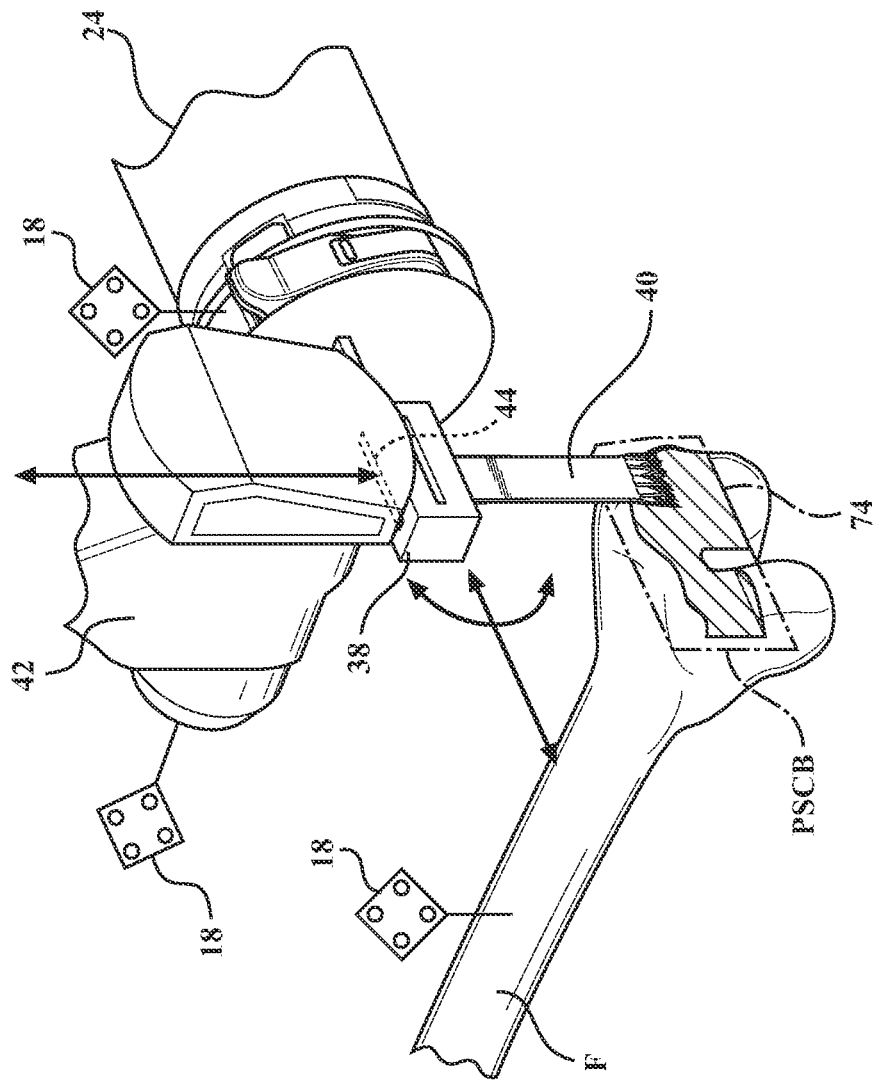
Figure 8E:
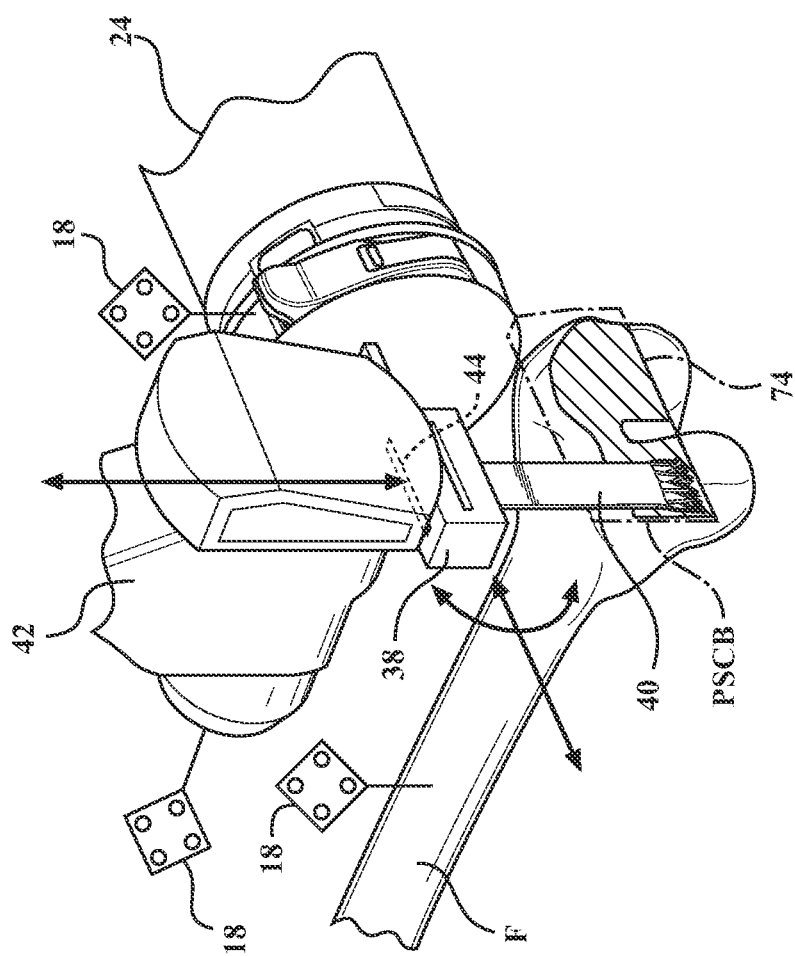

Referring to FIGS. 8C through 8E, the desired cutting plane 74 is shown having a patient-specific cutting boundary PSCB created in the manner described in U.S. Pat. Nos. 8,977,021 and 9,588,587, both of which are hereby incorporated herein by reference. As previously mentioned, customized virtual boundaries may be created based on patient-specific anatomy. In this case, the patient-specific cutting boundary PSCB indicates the desired limits of cutting of the patient's femur F in the desired cutting plane 74 based on the patient's anatomy, as determined, for example, by pre-operative imaging, intra-operative imaging, and/or surgical navigation, or the like. Cutting limits imposed by the patient-specific cutting boundary PSCB may be to avoid cutting certain portions of bone, to avoid cutting beyond the bone, to avoid cutting ligaments, to avoid other soft tissue, etc. The patient-specific cutting boundary PSCB may be defined with respect to images and/or models of the patient's anatomy and therefore can be tracked in the common coordinate system, via the anatomy tracker 18, or via other tracking methods.

In one version, the navigation system 14 tracks a position and/or orientation of the cutting guide 38 and/or the cutting tool 40 relative to the patient-specific cutting boundary PSCB. In some cases, the control system (e.g., the manipulator controller 34, the navigation controller 48, and/or the tool controller 62) can control operation of the cutting tool 40 in response to interaction between the cutting tool 40 and the patient-specific cutting boundary PSCB, when the cutting tool 40 cooperates with the cutting guide 38 to cut the tissue. For example, the control system can control power to the cutting tool 40 based on a position and/or orientation of the working end of the cutting tool 40 relative to the patient-specific cutting boundary PSCB or relative to other predefined boundaries.

The navigation controller 48 may determine one or more current conditions of the cutting guide 38 and/or the cutting tool 40, such as: (1) whether the cutting tool 40 is within the patient-specific cutting boundary PSCB (e.g., whether the patient-specific cutting boundary PSCB has been violated); (2) whether the cutting guide 38 and/or the cutting tool 40 are in a correct zone (e.g., volume) for a particular step of the surgical procedure; (3) whether the cutting tool 40 has reached a desired depth in the patient's anatomy; and/or (4) whether the cutting guide 38 and/or the cutting tool 40 is operating on/off a desired plane or axis. Such conditions indicate whether/when power can be applied to the motor MT operatively coupled to the cutting tool 40. The navigation controller 48 may transmit one or more control signals to the manipulator controller 34 and/or the tool controller 62 based on the current conditions. In some versions, if the control signal(s) received by the tool controller 62 indicate that the current conditions are appropriate for powering the motor MT, then the tool controller 62 may apply power to the motor MT. Of course, multiple conditions may need to be met before power is applied to the motor MT to start cutting. The control system may modulate or stop operation of the cutting tool 40 when one or more of the conditions are not met, e.g., the patient-specific cutting boundary PSCB is reached or exceeded, the cutting guide 38 and/or the cutting tool 40 are outside the correct zone, the cutting tool 40 is at the desired depth, and/or the cutting tool 40 is cutting off the desired plane/axis.

The control system may control operation of the cutting guide 38 and/or the cutting tool 40, and/or provide feedback based on their conditions in other ways besides modulating and/or stopping operation of the cutting tool 40. For example, the navigation controller 48 may transmit one or more control signals to the manipulator controller 34 and/or to the tool controller 62 to cause vibrations of the manipulator 22, cutting guide 38 and/or the cutting tool 40 to indicate any of the conditions of the cutting guide 38 and/or the cutting tool 40. For example, an eccentric motor (not shown), piezoelectric elements (not shown), or the like, may be disposed in the surgical instrument 42 and coupled to the tool controller 62 to cause such vibrations. In some versions, the navigation controller 48 may transmit a signal to the tool controller 62 to operate the eccentric motor/piezoelectric elements to cause vibrations of a hand-held portion of the surgical instrument 42 when one or more of the conditions are met. Such conditions could include any of the conditions disclosed herein, including, but not limited to: (1) the cutting tool 40 being within a predefined distance of a portion of the patient specific cutting boundary PSCB; (2) the cutting tool 40 being outside the patient specific cutting boundary PSCB; (3) the cutting guide 38 being at the desired location relative to bone; (4) the cutting guide 38 and/or cutting tool 40 being off the desired plane/axis; and/or (5) the cutting guide 38 and/or cutting tool 40 being on the desired plane/axis; and the like. Similar feedback may additionally, or alternatively, be transmitted to a wristband (not shown) worn by the user and/or other personnel. Such a wristband may comprise its own eccentric motor, piezoelectric element, or the like, to cause vibrations. The wristband may further comprise a controller in wireless communication with the navigation controller 48 via Bluetooth, Zigbee, or other communication protocol. Vibrations could also be generated on the cutting guide 38 and/or through the manipulator 22 (e.g., via separate eccentric motors/piezoelectric elements) operatively coupled to the manipulator controller 34, navigation controller 48, and/or tool controller 62. The joint motors of the manipulator 22 could also be manipulated to generate vibrations via their commutation, etc.

Additionally, or alternatively, the control system may dynamically control positioning of the cutting guide 38 so that the cutting tool 40 is unable to cut tissue beyond the patient-specific cutting boundary PSCB. For example, referring to FIG. 8C, the control system may autonomously control positioning of the cutting guide 38 in one or more degrees of freedom. See, for example, three possible degrees of freedom of movement of the cutting guide 38 illustrated by arrows in FIG. 8C that may be adjusted by the control system to control placement of the cutting tool 40 relative to the patient-specific cutting boundary PSCB, yet keep the cutting tool 40 on the desired cutting plane 74. In addition to such adjustments, the control system may also operate the manipulator 22 to automatically move the cutting guide 38 as the femur F moves to maintain a desired relationship between the cutting guide 38 and the femur F, e.g., to keep the cutting tool 40 on the desired cutting plane 74 and at the desired placement relative to the patient-specific cutting boundary PSCB.

Autonomous control of the position and/or orientation of the cutting guide 38 may be in cooperation with manual manipulation of the manipulator 22 in which the user manually moves (or manually causes movement of) the cutting guide 38 in one or more degrees of freedom. For instance, as the user is manually manipulating the cutting guide 38 to move in one degree of freedom, say vertically, the control system may autonomously move the cutting guide 38 laterally so that, at all times, the cutting guide 38 is placed such that the cutting tool 40 is unable to penetrate beyond the patient-specific cutting boundary PSCB. In one embodiment, when the force/torque sensor 60 is employed, the user may apply an input force substantially in the vertical direction indicating a desire to move the cutting guide 38 downwardly toward the femur F. However, instead of merely emulating the user's desired motion and moving the cutting guide 38 accordingly, solely in the vertical direction, the control system may add a lateral force to the user's applied vertical force such that the control system reacts to the user's manipulation by moving the cutting guide 38 laterally and vertically, to avoid cutting tissue beyond the patient-specific cutting boundary PSCB (compare FIGS. 8C and 8D, for example).

In some versions, the guide 44 is sized so that the cutting tool 40 is substantially limited from lateral or tilting motion relative to the guide 44. Data regarding a length of the cutting tool 40, a width of the cutting tool 40, a length of the guide 44, and a width of the guide 44, may be input into memory in the control system (e.g., in the navigation controller 48) to correlate a position and/or orientation of the cutting guide 38 to a position and/or orientation of the cutting tool 40 when fully inserted into the cutting guide 38. The position and/or orientation of the cutting tool 40 can also be measured using the techniques described herein to determine the position and/or orientation of the working end of the cutting tool 40 relative to the patient-specific cutting boundary PSCB. FIGS. 8C through 8E illustrate a sequence of manual and/or autonomous movement of the cutting guide 38 that allows the user to cut the femur F along the desired cutting plane 74, while keeping the cutting tool 40 from penetrating beyond the patient-specific cutting boundary PSCB.

Figure 9:
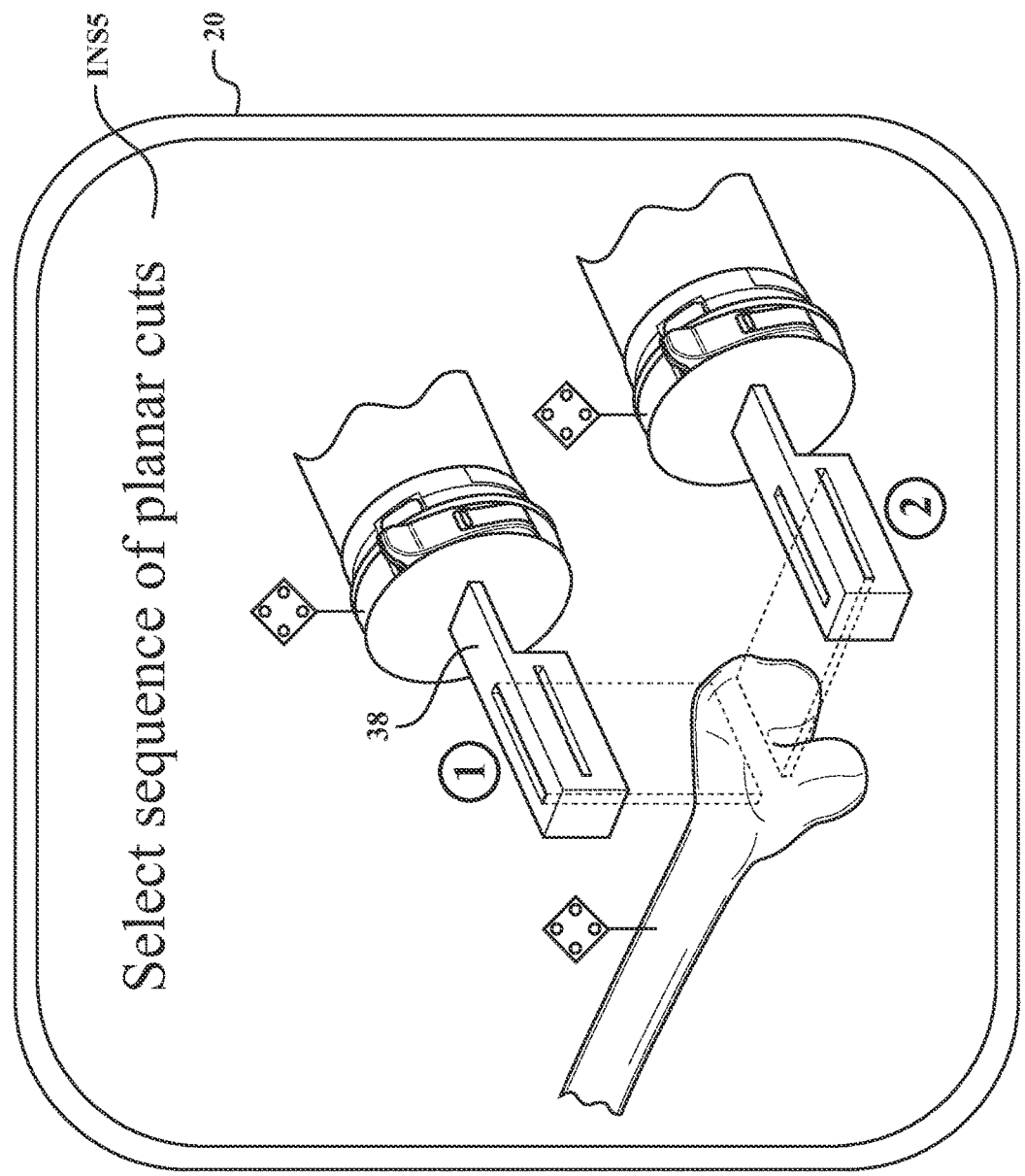
FIG. 9 illustrates a screen shot of a display screen showing instructions to a user to select a sequence of cuts to make.

As previously discussed, in some surgical procedures, many different cuts may need to be made to the tissue, such as multiple planar cuts, multiple peg/pilot holes, or the like. Accordingly, the surgical procedure is often carried out in a desired sequence of such cuts. The sequence may be stored in memory in the control system for later retrieval by the control system to control operation of the robotic manipulator 22 to perform the cuts in the desired sequence. For example, the control system may operate the robotic manipulator 22 to autonomously position the cutting guide 38 so that the cutting tool 40 aligns with a plurality of desired cutting planes/axes to make a plurality of cuts, in the desired sequence. Additionally, or alternatively, the control system may refer to the desired sequence stored in memory to control a workflow of steps displayed on the display 20 to the user so that the cuts are made by the user in the desired sequence. The desired sequence of positioning of the cutting guide 38 (or multiple, different cutting guides) may be established by a default setting based on the type of procedure, or may be based on predetermined criteria, such as: user preference; distance between the desired cutting planes/axes; current alignment of the cutting guide 38 relative to the desired cutting planes/axes; and required movement of the cutting guide 38 to reach the desired cutting planes/axes. FIG. 9 shows one example of instructions INS5 in which the user is prompted to select a desired sequence of planar cuts, by toggling the "1" and the "2" on the display 20 via one of the input devices. Once selected, the control system is ready to move the cutting guide 38 into position so that the cutting tool 40 aligns with a first desired cutting plane for the first planar cut (e.g., via operation in the semi-autonomous mode, haptic mode, etc.). Once the first planar cut is complete, the control system is ready to position the cutting guide 38 so that the cutting tool 40 aligns with a second desired cutting plane for the second planar cut (e.g., via operation in the semi-autonomous mode, haptic mode, etc.), and so on until all the necessary cuts have been made. In other versions, the robotic manipulator 22 is instructed to move to the next position (e.g., the second desired cutting plane) based on user input, e.g., via a button, touchscreen, hand-gesture, etc. Additionally, or alternatively, the user input could include forces applied by the user on the cutting guide 38, robotic manipulator 22, or elsewhere, being of such direction and/or magnitude, to indicate a desire to move the next position.

In some versions, the desired cut to be made to the bone may be indicated by physically positioning the cutting tool 40 at or near the desired cutting location and providing corresponding input to the navigation controller 48 once at the desired cutting location (e.g., via a push button, touchscreen, foot pedal, gesture, etc.), without engaging the cutting guide 38. During such placement, the navigation system 14 tracks a pose of the cutting tool 40 relative to the bone to determine which cut of the sequence of cuts is being identified (e.g., whichever one is closest to the user's placement when the input is received). The navigation controller 48 may automatically identify the cut on the display 20 and prompt the user for input confirming the cut. Once the desired cut has been confirmed, then the navigation controller 48 transmits a corresponding input signal to the manipulator controller 34 and the manipulator controller 34 may then automatically place the cutting guide 38 at the initial guide location associated with the desired cut. The navigation pointer P could be used in a similar manner to point to the location on the bone in which the user wishes to make the next cut and the navigation controller 48 may respond as described above.

Figure 10:
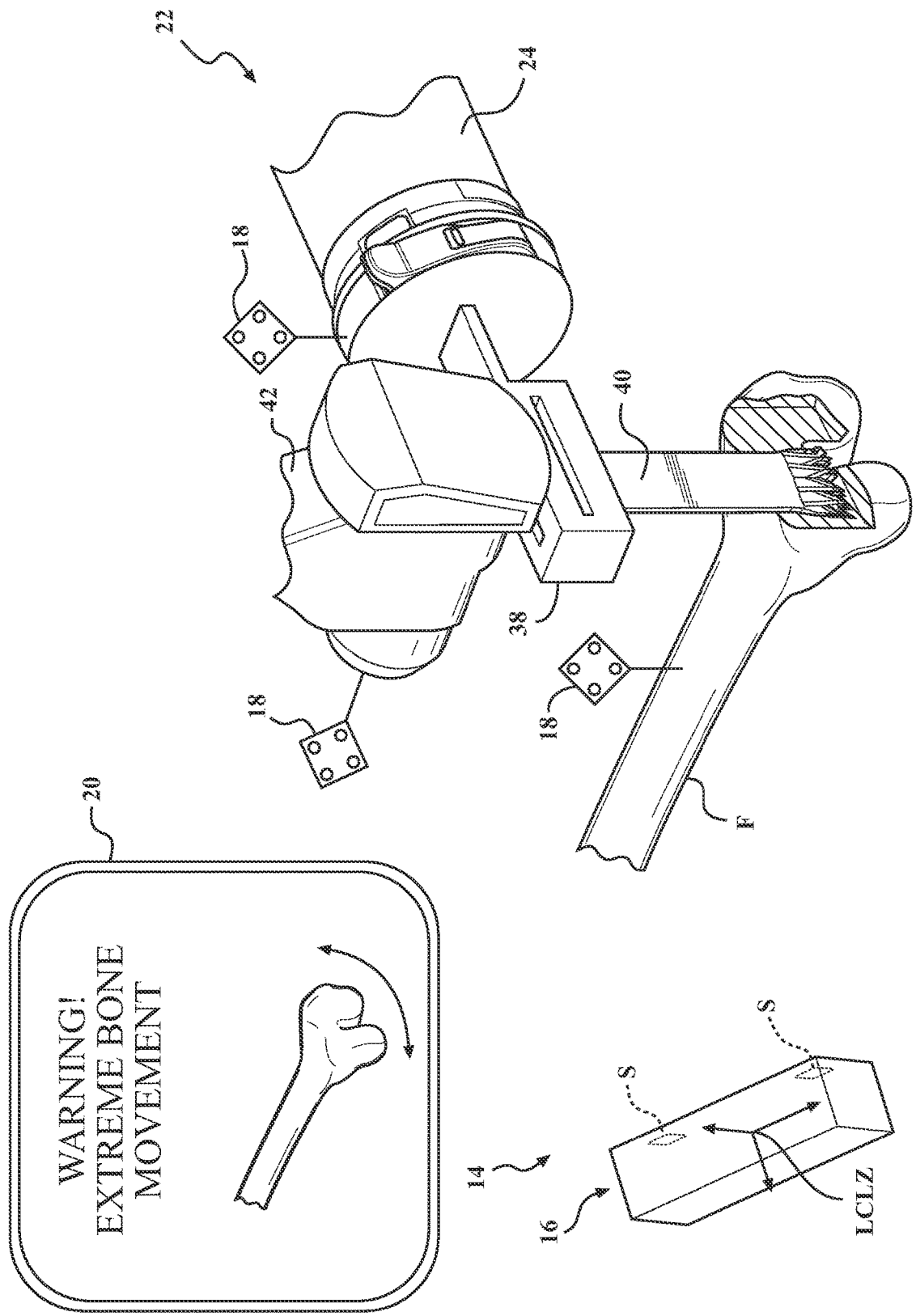
FIG. 10 illustrates excessive movement of the anatomy.

Referring to FIG. 10, the navigation system 14 is configured to determine one or more of a velocity or acceleration of the tissue being treated. For example, owing to its tracking of the tissue via the tracker 18, the navigation system 14 is able to monitor changes in position/velocity of the tissue over time, including changes in positions and velocities about and along the axes of the localizer coordinate system LCLZ. Accordingly, velocity and/or acceleration limits could be set and the monitored velocities and/or accelerations could be compared to their limits to see when their limits are exceeded. An associated warning could also be displayed on the display 20, as shown in FIG. 10.

In some cases, the tissue may move faster and/or with greater acceleration than the robotic manipulator 22 can effectively respond and still maintain alignment of the cutting guide 38 with the desired cutting plane or with a desired cutting trajectory/axis. The limits may be set to prevent such situations and possible undesired cutting of the tissue. In one embodiment, the control system switches the robotic manipulator 22 to the free mode (e.g., from the semi-autonomous mode or the haptic mode) in response to one or more of the velocity and acceleration of the tissue exceeding one of the predetermined limits. As a result, the cutting guide 38 and/or the cutting tool 40 would be unlocked from the desired cutting plane or desired cutting trajectory/axis and be free to move relative to the tissue. Additionally, the control system, such as through the tool controller 62, may cease operation of the motor MT driving the cutting tool 40. The navigation system 14 continuously monitors the velocity/acceleration of the tissue after switching to the free mode, and the control system may re-position the cutting guide 38 (or allow repositioning of the cutting guide 38), via the semi-autonomous mode, haptic mode, etc., so that the cutting tool 40 is re-aligned with the desired cutting plane or desired cutting trajectory/axis in response to the navigation system 14 determining that the one or more of the velocity and acceleration has resumed to being at or below the predetermined limit(s).

Figure 11:
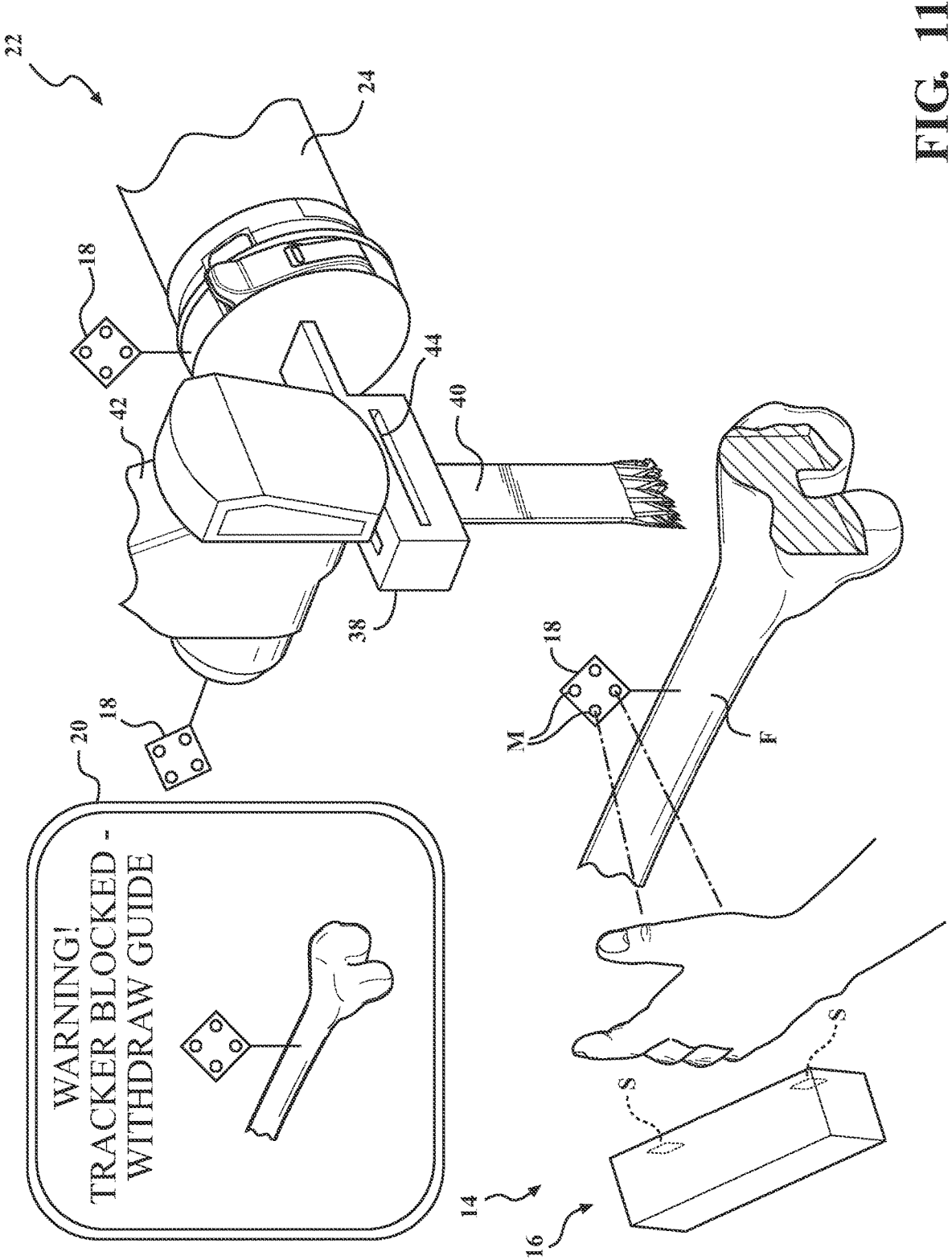
FIG. 11 illustrates a tracker blocked condition.

Referring to FIG. 11, as previously described, the sensors S of the localizer 16 rely on line-of-sight to the trackers 18 to be able to receive light from the tracking elements or markers M, active or passive. Occasionally, one or more of the markers M may be blocked from view of one or more of the sensors S of the localizer 16. As a result, reliable tracking of the position and orientation of the tracker 18 and associated object to which the tracker 18 is attached ceases. The navigation system 14 can determine if one or more of the markers M is blocked from view of the localizer 16 based on feedback from the sensors S. For example, the navigation controller 48 may be unable to triangulate a position of a marker M because only one sensor S is receiving light from the marker M, while the other sensor S is not receiving light from the marker M. In response to determining that one of the markers M is blocked from view, the control system facilitates withdrawal of the cutting guide 38 away from the tissue, as shown in FIG. 11. Such withdrawal may be autonomous or may be in the form of instructions INS6 to the user on the display 20 to withdraw the cutting guide 38, such as in the free mode or haptic mode. The control system may automatically switch operation of the robotic manipulator 22 to the free mode or haptic mode in the event of a blocked condition, and unlock the cutting guide 38 for movement, and/or may cease operation of the motor MT of the cutting tool 40, as described herein. Since tracking of the tissue, for example, is no longer reliable due to the blocked tracker 18, the control system may be configured to operate the robotic manipulator 22 to withdraw the cutting guide 38 away from the tissue along an orientation/axis of the cutting guide 38 stored in the navigation controller 48 and/or manipulator controller 34 prior to the one or more of the markers M being blocked from view. The navigation system 14 continuously monitors the blocked condition and, in response to the marker M no longer being blocked from view of the localizer 16, the control system may re-position the cutting guide 38 (or allow repositioning of the cutting guide 38), via the semi-autonomous mode, haptic mode, etc., so that the cutting tool 40 is re-aligned with the desired cutting plane or desired cutting trajectory/axis.

Figure 13:
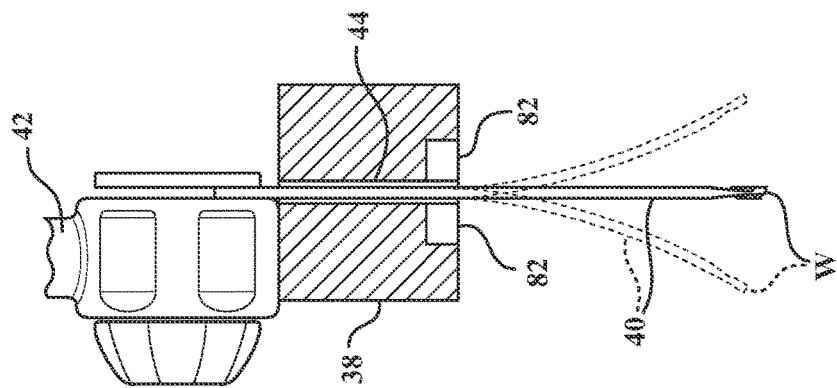
FIG. 13 is a partial cross-sectional view showing sensors of the cutting guide to detect loading of the cutting tool that may indicate deflection of the cutting tool.
Figure 12:
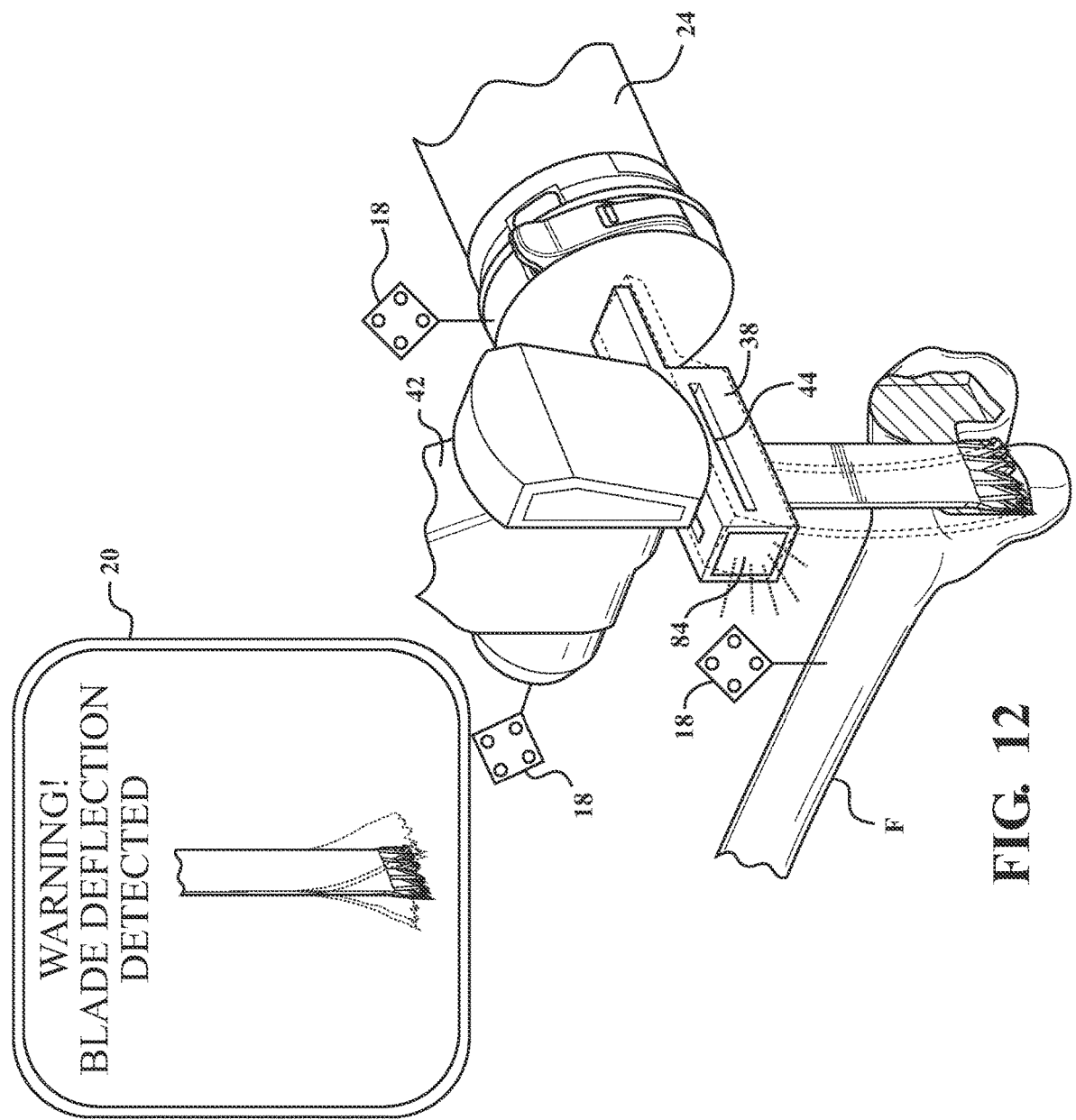
FIG. 12 illustrates deflection of the cutting tool during the surgical procedure and associated warning on the display screen.

Referring to FIGS. 12 and 13, the control system comprises one or more tool load sensors 82 (see FIG. 13) coupled to the cutting guide 38 to sense a load applied on the cutting guide 38 by the cutting tool 40 and/or to sense deflection of the cutting tool 40. The tool load sensors 82 may comprise one or more load cells, pressure sensors, optical sensors, Hall Effect sensors, ultrasonic sensors, and the like, and/or any other suitable sensor for measuring/detecting the load applied on the cutting guide 38 by the cutting tool 40 and/or associated deflection of the cutting tool 40. In the version shown in FIG. 13, the tool load sensors 82 comprise pressure sensors fixed in a body of the cutting guide 38 to be exposed to the guide portion 44 (e.g., the slot) such that any deflection load (see hidden lines) placed on the cutting tool 40 at the working end W will be sensed by the pressure sensors and an associated input signal will be generated.

The tool load sensors 82 are coupled to the manipulator controller 34, the navigation controller 48, and the tool controller 62 (see FIG. 2) to provide the input signals to any of these controllers 34, 48, 62 as needed. The measurements from the tool load sensors 82 may provide an indication that the cutting tool 40 is deflecting in an undesired manner, e.g., when the measurements exceed predetermined limits. Accordingly, the control system (e.g., the tool controller 62) may deactivate operation of the motor MT of the cutting tool 40 to cease cutting with the cutting tool 40 in response to the load applied on the cutting guide 38 by the cutting tool 40 exceeding one of the predetermined limits. Additionally, or alternatively, the control system may account for such loads/deflections by instructing the robotic manipulator 22 to move the cutting guide 38 to compensate for such loads/deflections. Some users may naturally tend to apply minor deflecting loads without desiring to do so, but the control system can account for such tendencies. For example, if the detected load is commensurate with a deflection of 5 degrees, the control system may instruct the robotic manipulator 22 to rotate the cutting guide 38 about 5 degrees in an opposite direction. As a result, the net effect of the deflection would result in the cutting tool 40 being operated along the desired trajectory/plane, etc. In some versions, such compensation may be employed when the measured load is greater than a first threshold load, but less than a second threshold load. In some versions, when the user applies a force on the cutting tool 40 that results in the measured load being above the second threshold, this may be an indication that the user wishes to reorient the cutting guide 38 for the next position, e.g., the next desired cutting plane. Accordingly, the control system may automatically align the cutting guide 38 with the next desired cutting plane in response to detecting the application of such a load. This may be in combination with detecting that the cutting tool 40 is also withdrawn a specified distance from the tissue to allow such reorienting without engaging other tissue along the way.

The control system may also comprise a tool load indicator 84, such as one or more visual indicators located on the cutting guide 38, as shown in FIG. 12. The tool load indicators 84 may be activated by the control system (e.g., the manipulator controller 34, the navigation controller 48, and/or the tool controller 62) in response to the load applied on the cutting guide 38 by the cutting tool 40 exceeding the predetermined limit. The tool load indicator 84 shown in FIG. 12 comprises one or more lights, such as light emitting diodes (LEDs), controlled by the manipulator controller 34 to continuously emit colored light, but may be operated at a desired frequency to flash/blink, and/or may emit multiple colors of light. The tool load indicators 84 may comprise one or more visual indicators, tactile indicators, and audible indicators. A separate visual indicator may be a related message on the display 20, as shown in FIG. 12.

Figure 15:
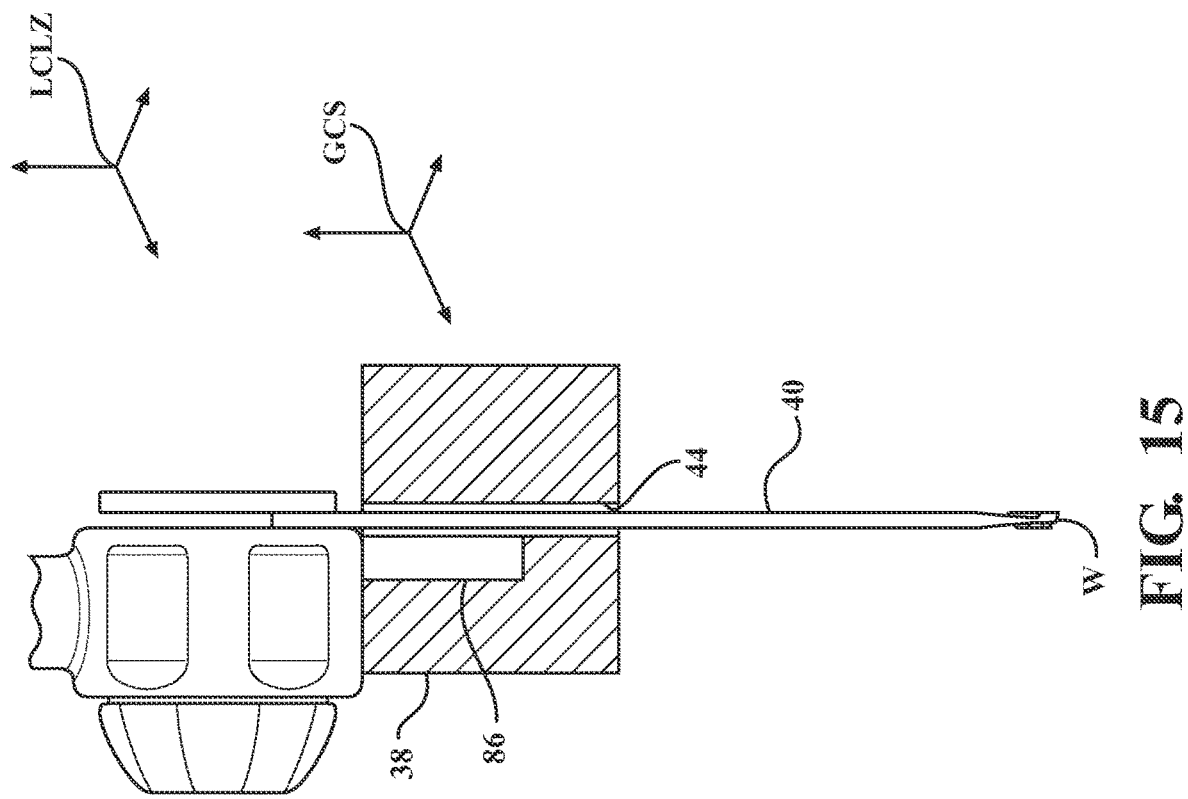
FIG. 15 is a partial cross-sectional view showing an optical sensor to read the graduated markings on the cutting tool to determine depth of the cutting tool in the cutting guide.
Figure 14:
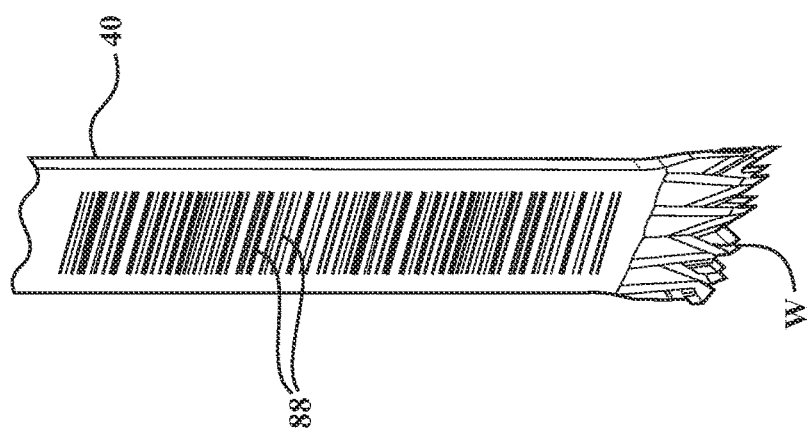
FIG. 14 is a perspective view of a cutting tool with graduated markings to indicate depth.

Referring to FIGS. 14 and 15, the control system comprises one or more tool position sensors 86 (see FIG. 15) coupled to the cutting guide 38 to sense a position of the cutting tool 40 with respect to the cutting guide 38. More specifically, the positions sensors 86 assist in locating the working end W of the cutting tool 40 (e.g., the tip, distal end, etc.) so that the control system is able to determine the location of the working end W of the cutting tool 40 relative to the tissue of the patient 12 via a combination of the navigation system 14 monitoring a position and orientation of the cutting guide 38 and its associated guide portions 44 and the tool position sensors 86 detecting a position of the cutting tool 40 in the cutting guide 38. Thus, the tool position sensors 86 may have their own coordinate systems or be located at a known location in the guide coordinate system GCS so that the measurements taken from the position sensors 86 are also made relative to the guide coordinate system GCS, which can be transformed to the common coordinate system, e.g., the localizer coordinate system LCLZ. The position sensors 86 may be used as an alternative to, or in addition to, placing a tracker 18 on the cutting tool 40 and/or the free-hand surgical instrument 42 to which it is attached.

The tool position sensors 86 may comprise one or more optical sensors, Hall Effect sensors, ultrasonic sensors, and the like, or any other suitable sensor for measuring/detecting a position of the cutting tool 40 in the cutting guide 38. In the version shown in FIG. 13, the tool position sensors 86 comprise one or more optical sensors, such as CCD or CMOS, fixed in the body of the cutting guide 38 to be exposed to the guide portion 44 (e.g., the slot) such that markings 88 on the cutting tool 40 are visible to the optical sensors. Optical sensors could be positioned in a spaced relationship on opposing sides of the guide portion 44 and/or two or more optical sensors could be spaced on the same side of the guide portion 44 so that any slant of the cutting tool 40 in the guide portion 44 could be detected, or a single optical sensor could be employed. In any case, the optical sensors read the markings 88 on the cutting tool 40 to determine depth of the cutting tool 40 relative to the cutting guide 38. To this end, the markings 88 at each depth may be different, or spacing between markings M may be such that the depth can be determined by the optical sensors generating images of the markings 88. In one version, the optical sensors may operate similar to optical linear encoders.

The tool position sensors 86 are coupled to the manipulator controller 34, the navigation controller 48, and the tool controller 62 to provide input signals to any of these controllers 34, 48, 62 as needed. The measurements from the tool position sensors 86 may be combined with navigation data regarding a position and orientation of the cutting guide 38 in the localizer coordinate system LCLZ to determine a position and/or orientation of the cutting tool 40 (e.g., the working end) in the localizer coordinate system LCLZ relative to a position and orientation of the tissue being cut. Accordingly, the control system is then able to generate images of the cutting guide 38, the cutting tool 40, and/or the tissue on the displays 20, or elsewhere and update the images in real-time so that the user can see the relative movement between the cutting guide 38, the cutting tool 40, and/or the tissue on the displays 20. Additionally, by knowing the position and/or orientation of the cutting tool 40, the control system can track its movement relative to any virtual objects, such as virtual cutting boundaries, and react accordingly, such as by shutting down power to the motor MT if the control system detects that the working end W of the cutting tool 40 has exceeded a boundary. Similarly, the control system may allow power to the motor MT to cause movement (e.g., rotation, translation, vibration, etc.) of the cutting tool 40 once the control system detects that the cutting tool 40 is within the cutting guide 38. Thus, in some cases, the cutting tool 40 is inoperable outside of the cutting guide 38, and must be located at least partially within the cutting guide 38, for power to be distributed to the motor MT.

Additionally, or alternatively, the navigation system 14 may also track a location of the cutting tool 40 relative to the cutting guide 38 to determine whether the cutting tool 40 is located in the cutting guide 38 or otherwise engaging the cutting guide 38, i.e., to determine an engagement state of the cutting tool 40 with respect to the cutting guide 38. The manipulator controller 34 then utilizes this information to determine if/when appropriate to operate the manipulator 22 to move the cutting guide 38. For example, the navigation controller 48 may transmit a positive engagement state signal to the manipulator controller 34 indicating that the cutting tool 40 is located in one of the guides 44 (e.g., slots) of the cutting guide 38. In response, the manipulator controller 34 may disable/prevent operations to move the cutting guide 38 until the user removes the cutting tool 40 from the cutting guide 38. Conversely, in some cases, the manipulator controller 34 may only allow certain operations if the cutting tool 40 is present in the cutting guide 38.

In some versions, the navigation controller 48 is provided with geometric data (e.g., stored in memory) associated with the cutting guide 38, such as a 3-D model of the cutting guide 38, which can be defined initially in the guide coordinate system GCS and then transformed to any suitable coordinate system, including the localizer coordinate system LCLZ (e.g., via coordinate transforms, etc.). The cutting guide model may comprise a solid body model, triangulated mesh, and/or other form of surface or volumetric model, or the like. This geometric data defines coordinates/locations of the guide portions 44 (e.g., the slots) for the navigation controller 48. Additionally, the navigation controller 48 is provided with geometric data (e.g., stored in memory) associated with the cutting tool 40, such as a 3-D model of the cutting tool 40, which can be defined initially in a tool coordinate system and then transformed to any suitable coordinate system, including the localizer coordinate system LCLZ. The cutting tool model may comprise a solid body model, triangulated mesh, and/or other form of surface or volumetric model, or the like. By virtue of the trackers described above and/or other tracking modalities, the navigation controller 48 is able to track a pose of the cutting tool 40 relative to the guide portions 44 of the cutting guide 38. Moreover, the navigation controller 48 is thereby able to detect whether the cutting tool 40 is present in one of the guide portions 44 or not (e.g., by comparing their current coordinates in the same coordinate system). In some versions, the tool controller 62 can supply power to the motor MT of the cutting tool 40 when the cutting tool 40 is detected by the navigation controller 48 as being in one of the guide portions 44, e.g., a positive engagement state signal. For instance, the navigation controller 48 may transmit a corresponding signal to the tool controller 62. Conversely, the tool controller 62 can deactivate or disable power to the motor MT when the navigation controller 48 detects that the cutting tool 40 is absent from any of the guide portions 44 and transmits a corresponding negative engagement state signal to the tool controller 62.

Additionally, or alternatively, the cutting guide 38 may have sensors coupled to the cutting guide 38 that detect the presence/absence of the cutting tool 40 in the guide portions 44. These sensors may be proximity sensors, limit switches, ultrasonic sensors, motion sensors, optical sensors, combinations thereof, or the like, which could be employed by the tool controller 62 to control power to the motor MT based on the presence/absence of the cutting tool 40 in any of the guide portions 44. In some embodiments, the sensors communicate directly with the tool controller 62, such as via wire or wirelessly (e.g., Bluetooth, Zigbee, IR, etc.) to control power to the motor MT based on the presence/absence of the cutting tool 40 in the guide portions 44. The cutting tool 40 can be controlled using any appropriate communication means using either wired or wireless communication schemes.

Figure 15B:
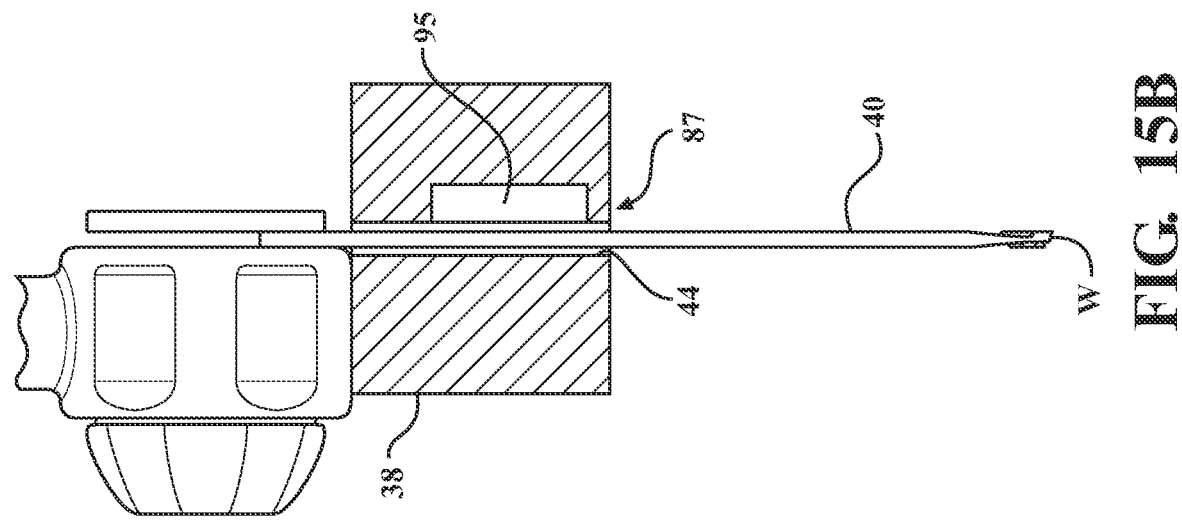
FIG. 15B is a partial cross-sectional view showing an optical sensor used to identify the cutting tool.
Figure 15A:
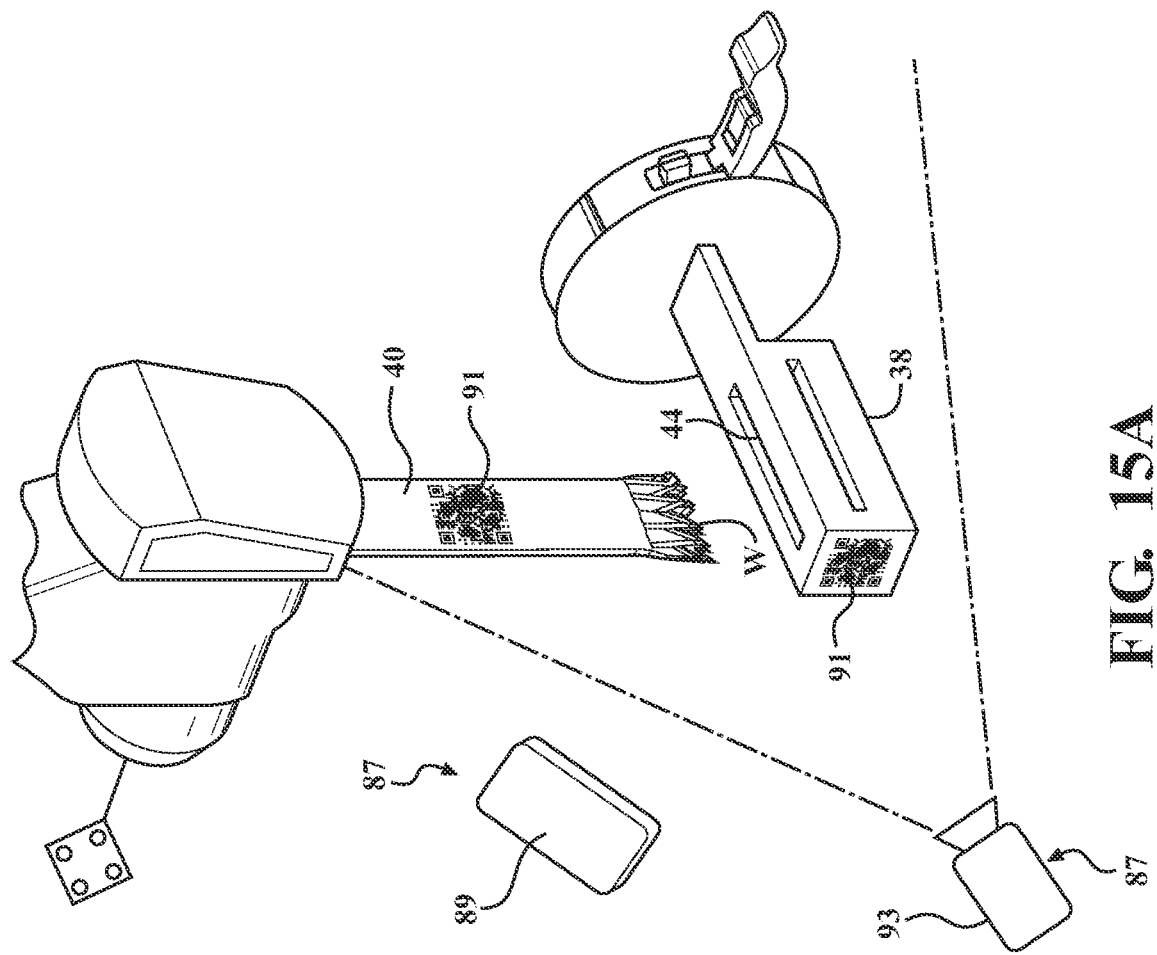
FIG. 15A is a partial perspective view of the cutting tool and cutting guide illustrating techniques to identify the cutting guide and/or cutting tool to determine whether the cutting tool is appropriate for use with the cutting guide.

Referring to FIGS. 15A and 15B, one or more identification devices 87 may also be employed to identify the cutting guide 38 and/or the cutting tool 40. The identification devices 87 may comprise one or more sensors, such as optical sensors, RF sensors, and the like, or any other suitable sensor for identifying the cutting guide 38 and/or cutting tool 40. In the version shown in FIG. 15A, the identification devices 87 may comprise a scanner/reader 89 to read one or more markings/tags 91 on the cutting tool 40. For example, the scanner/reader 89 may be a bar code scanner, QR code scanner, RFID reader or the like and the markings/tags 91 may be a bar code, QR code, RFID tag, or any other suitable form of identifier. The scanner/reader 89 may be a separate portable electronic device, may be attached to the manipulator 22, may be attached to the cutting guide 38, or the like.

The identification device 87 may additionally, or alternatively, comprise one or more cameras 93 (e.g., with one or more CCD or CMOS sensors) employing machine vision technology and an associated machine vision controller to detect a shape, size, and/or configuration of the cutting guide 38 and/or cutting tool 40 by obtaining images of the cutting guide 38 and/or cutting tool 40 and matching the images taken of the cutting guide and/or cutting tool 40 to a library of stored images to identify the cutting guide 38 and/or cutting tool 40 using pattern recognition or other image processing algorithms used for identification, as described below. The machine vision controller may comprise a frame grabber using either an analog or digital interface to obtain images of the cutting guide 38 and/or the cutting tool 40. Additionally, or alternatively, the cameras 93 may comprise digital cameras capable of direct connection to the machine vision controller. 2-D/3-D imaging, multispectral imaging, time-of-flight cameras and imaging, grid array based imaging, and/or stereoscopic vision/imaging, and the like may be employed.

After images are acquired by the cameras 93, they are processed. Multiple stages of processing may be used to extract the cutting guide 38 and/or the cutting tool 40 from the images (e.g., by comparing image data associated with the images to the object data stored in the machine vision controller or navigation controller 48, which is coupled to the machine vision controller). Machine vision image processing methods that may be employed include methods such as: stitching/registration; filtering; thresholding; pixel counting; segmentation; edge detection; color analysis; blob detection and extraction; pattern recognition/template matching; 2-D bar code reading; and/or optical character recognition; and/or any other suitable methods for processing images for purposes of identification.

In the version shown in FIG. 15B, the identification device 87 comprises one or more optical sensors 95, such as CCD or CMOS, fixed to the body of the cutting guide 38 to be exposed to the guide portion 44 (e.g., the slot) such that a tag on the cutting tool 40 is visible to the optical sensors 95. In some cases, the identification of the cutting guide 38 may already be stored in memory in the navigation controller 48 as a result of being selected by the user on the user interface or by separately identifying the cutting guide 38 when attaching the cutting guide 38 to the manipulator 22, e.g., via RFID tag/reader, etc.

Figure 16:
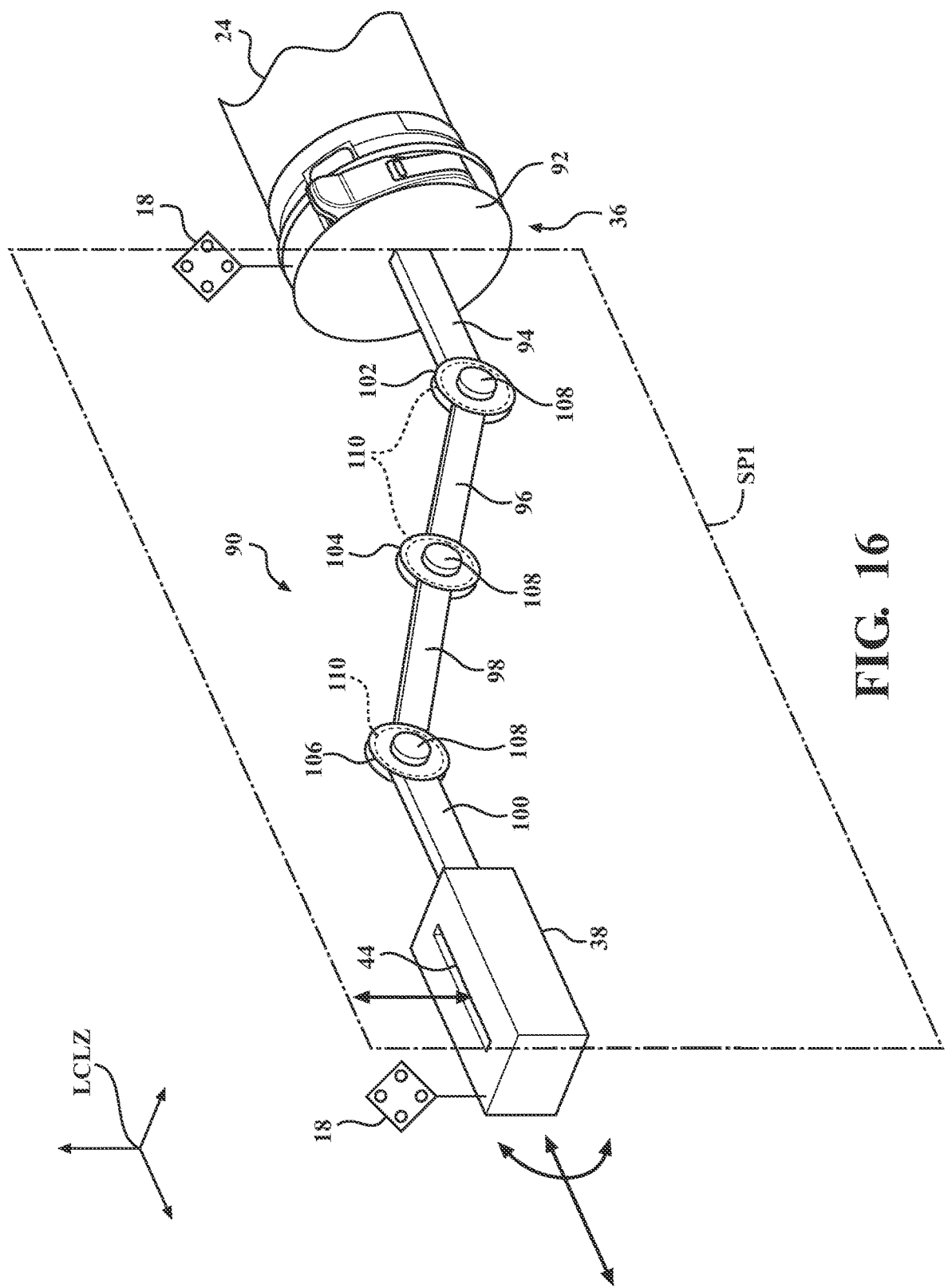
FIG. 16 is a perspective view of an articulating, planar arm that allows the cutting guide to move relative to a base plate of the end effector in a single plane.

The identification devices 87 may be coupled to the navigation controller 48 to transmit data, such as image data, code data, etc. to the navigation controller 48 so that the navigation controller 48 can identify the cutting guide 38 and/or cutting tool 40. For example, the particular cutting guide 38 and/or cutting tool 40 can be identified by comparing and matching the scanned bar code, QR code, RFID data, etc. to identifiers listed in a lookup table of identifiers associated with various known cutting guides and/or cutting tools and stored in memory on the navigation controller 48. The lookup table may also associate each cutting tool with one or more acceptable cutting guides that are appropriate for use with the particular cutting tool. As a result, the navigation controller 48 is able to determine which cutting guide 38 is being used, which cutting tool 40 is being used, and whether that particular cutting tool is appropriate for use with that particular cutting guide 38. If the cutting tool 40 is not appropriate for use with the cutting guide 38, the tool controller 62 may disable/prevent operation of the motor MT, the manipulator controller 34 may disable/prevent movement of the cutting guide 38, the control system may notify the user via the display 20 and prompt for confirmation from the user to continue, and/or the control system may trigger other suitable responses. Conversely, if the cutting tool 40 is determined by the navigation controller 48 to be suitable for use with the cutting guide 38, then operation may proceed normally. Referring to FIG. 16, an articulating linkage 90 interconnects a base 92 of the end effector 36 and the cutting guide 38 to constrain movement of the cutting guide 38 to a single plane SP1 relative to the base 92 of the end effector 36. The articulating linkage 90 may be active, passive, or combinations thereof. As shown, the articulating linkage 90 comprises a plurality of links 94, 96, 98, 100. More or less links are also possible in other versions. Here the first link 94 is fixed at one end to the base 92 of the end effector 36 and extends from the base 92 to a first rotational joint 102. Second link 96 is pivotally connected to the first link 94 at the first rotational joint 102 and extends from the first rotational joint 102 to a second rotational joint 104. Third link 98 is pivotally connected to the second link 96 at the second rotational joint 104 and extends from the second rotational joint 104 to a third rotational joint 106. Fourth link 100 is pivotally connected to the third link 98 at the third rotational joint 106 and extends from the third rotational joint 106 to the cutting guide 38, i.e., the cutting guide 38 is fixed to one end of the fourth link 100.

As a result of the configuration of links 94, 96, 98, 100 and joints 102, 104, 106, the cutting guide 38 is able to move in three degrees of freedom as shown by the arrows in FIG. 16. Other configurations are also possible. Additionally, or alternatively, translational joints, or other joint types, may also be employed. The joints 102, 104, 106 may be lockable to hold the cutting guide 38 in a desired position, such as by one or more locking devices 108, e.g., clamps, fasteners (e.g., tightening bolt/nut), brakes, or the like. Joint stops (not shown) may also be employed to limit rotation about the joints. The joint stops may be manually set, or may be automated and set by the control system. Arm position sensors 110, such as rotary encoders, potentiometers, or other types of sensors, may be positioned at each of the joints 102, 104, 106 to determine current rotational positions of the links 96, 98, 100 to determine a position and orientation of the cutting guide 38 relative to the base 92 of the end effector 36. Additionally, or alternatively, a separate tracker 18 may be placed on the cutting guide 38 and calibrated/registered to the cutting guide 38 to be able to track a position and orientation of the cutting guide 38 in the common coordinate system (e.g., the localizer coordinate system LCLZ) so that a location of the cutting guide 38 relative to the tissue can be determined and used by the control system to implement the functions and methods described herein.

Figure 16A:
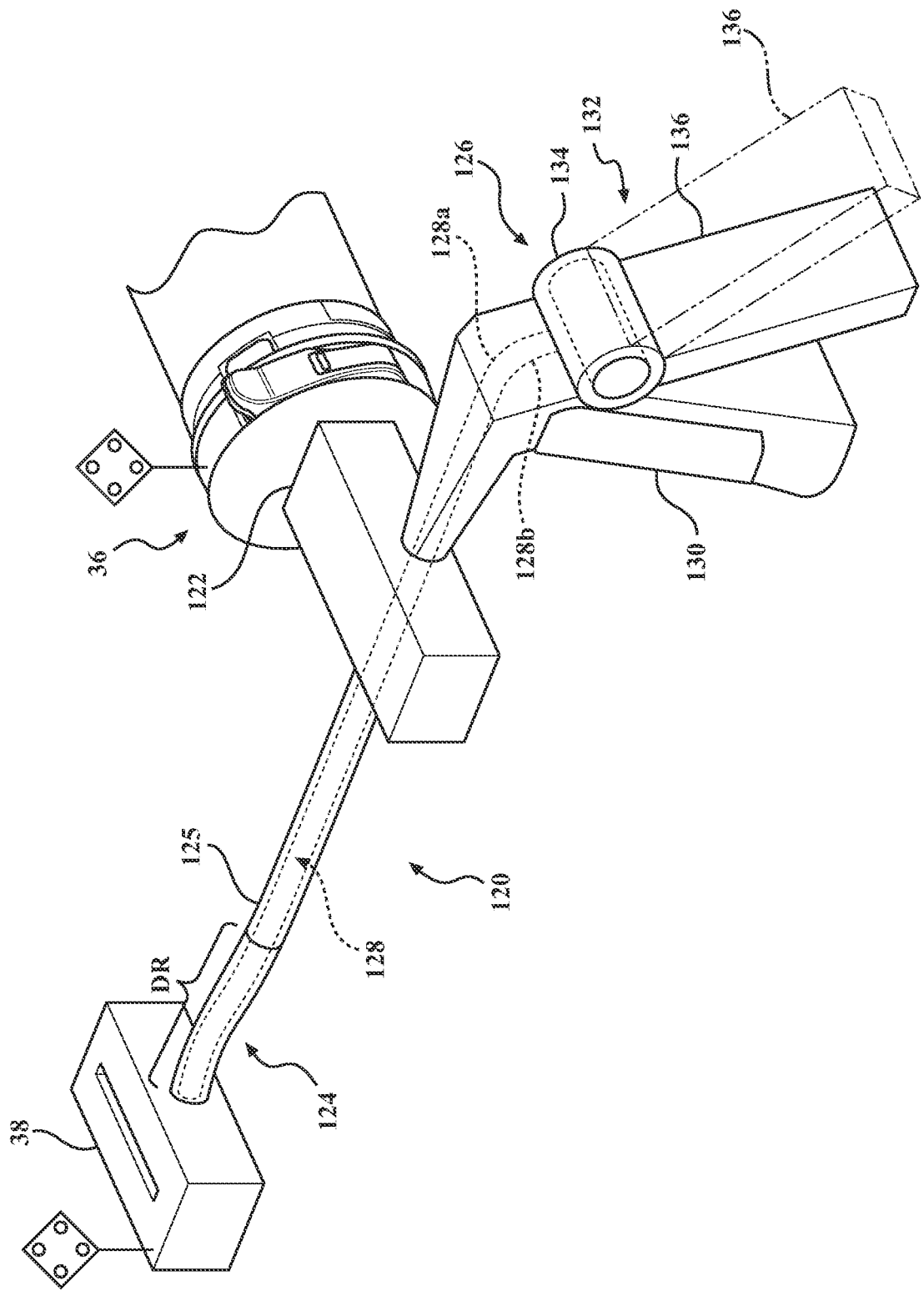
FIG. 16A is a perspective view of a flexible tool that allows the cutting guide to move relative to the base plate of the end effector in at least one degree of freedom.

FIG. 16A shows another articulating linkage 120 that interconnects a base 122 of the end effector 36 and the cutting guide 38 to facilitate movement of the cutting guide 38 relative to the base 122. In this example, the articulating linkage 120 comprises a flexible tool 124 that interconnects the base 122 and the cutting guide 38. The flexible tool 124 may comprise a conduit 125 extending from the base 122 to the cutting guide 38. The conduit 125 has a proximal region and a distal region DR capable to flexing relative to the proximal region. The conduit 125 may be formed of plastic, metal, combinations thereof, and may be elastic or semi-elastic in some cases. The conduit 125 may be relatively rigid in the proximal region and flexible in the distal region DR so that the distal region DR is able to flex relative to the proximal region.

In the example shown, the flexible tool 124 comprises one or more control wires 128 to control movement of the distal region. Only two control wires 128 are shown, but one, two, three, four, or more control wires may be employed and may extend along a length of the flexible tool 124 inside a wall of the conduit 125 or may extend in a lumen of the conduit 125. If two, three, four, or more control wires 128 are employed, they may be circumferentially, equally spaced about a center of the conduit 125 along its length. The control wires 128 may be fixed to the conduit 125 at a distal end of the conduit 125.

A control device 126 is attached to the flexible tool 124 to control tension of the control wires 128. Tension of a control wire causes deflection of the distal region DR generally in the direction of the tensioned control wire. The control device 126 comprises a handle 130 and an actuator 132 operatively coupled to the control wires 128 to control tensioning of the control wires 128. In the version shown, the actuator 132 comprises a drum 134 that rotates in response to movement of a lever 136. The control wires 128 extend from the distal end of the conduit 125 to the drum 134 and are fixed to the drum 134 such that when the drum 134 rotates in a first direction, a first control wire 128a is placed in tension, while a second control wire 128b is relaxed, and when the drum 134 rotates in the opposite direction, the second control wire 128b is placed in tension, while the first control wire 128a is relaxed. Operation of the actuator 132 causes desired deflection of the distal region DR of the conduit 125 and corresponding movement of the cutting guide 38, which is fixed to the distal end of the conduit 125. In embodiments where three or more control wires are employed, additional handles/actuators may be used to operate the additional control wires. Other forms of actuators, e.g., knobs, dials, motors, etc., could be used to tension the control wires. Other articulating linkages may also be employed such as those shown in U.S. Patent Application Pub. No. 2018/0242962, entitled "Surgical Instrument with Articulating Region," which is hereby incorporated herein by reference.

Figure 16B:
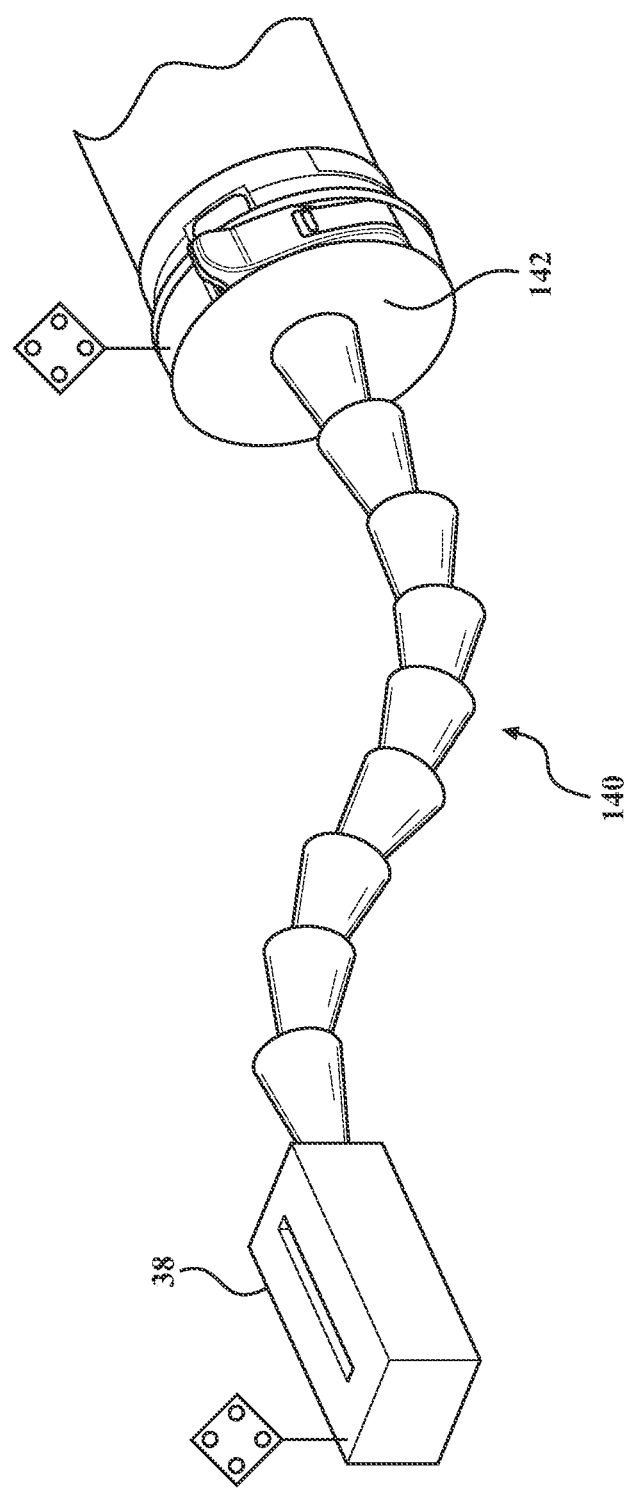
FIG. 16B is a perspective view of an articulating manipulator that allows the cutting guide to move relative to the base plate of the end effector in multiple degrees of freedom.

FIG. 16B illustrates another example of articulating linkage 140 that could be employed between the base 142 and the cutting guide 38 to position the cutting guide 38 relative to the tissue. In this version, the articulating linkage 140 comprises a snake-like robotic manipulator to control a position of the cutting guide 38.

In some embodiments, in addition to the cutting guide 38 being moved to align with the tissue along a desired trajectory/plane, the tissue of the patient may be moved to provide a desired alignment with the cutting guide 38. This could be accomplished manually, or with one or more manipulators coupled to the patient. Such an arrangement that could be used to move the tissue of the patient is shown, for example, in U.S. Patent Application Pub. No. 2014/0188129, entitled "Motorized Joint Positioner," which is hereby incorporated herein by reference.

Figure 17:
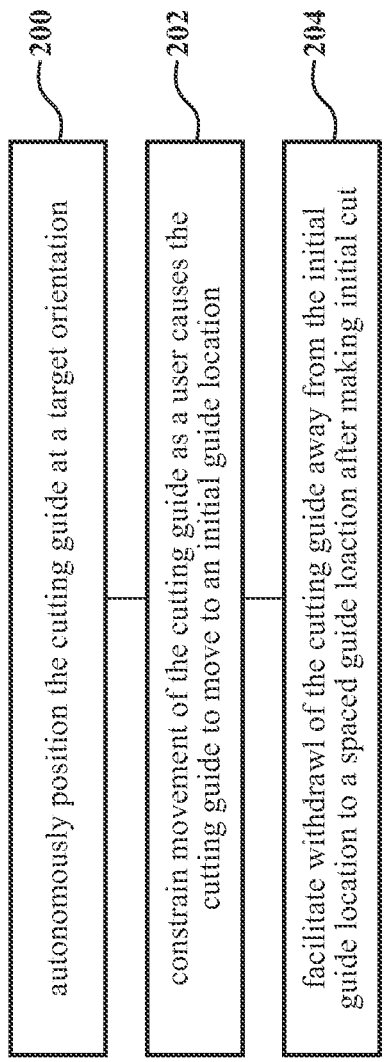
FIGS. 17 and 18 illustrate steps that may be carried out during the surgical procedure.

Referring to FIG. 17, one example of steps carried out by the control system to locate the cutting guide 38 relative to the tissue is illustrated. In step 200, the cutting guide 38 is first autonomously positioned at the initial target position and/or orientation relative to the tissue to be cut, as shown in FIG. 5A, and described above. In step 202, once the cutting guide 38 is located at the initial target position and/or orientation, then the control system is readied for the user to move or cause movement of the cutting guide 38 to the initial guide location GL1 shown in FIG. 5B. The control system constrains movement of the cutting guide 38 as the user manually manipulates the end effector 36 to cause the cutting guide 38 to move toward the tissue to the initial guide location GL1 adjacent to the tissue such that the cutting guide 38 remains in the target orientation at the initial guide location GL1. In step 204, after the cutting tool 40 is inserted into the cutting guide 38 at the initial guide location GL1 to make the initial cut, the control system facilitates withdrawal of the cutting guide 38 away from the initial guide location GL1 to the spaced guide location GL2 in the manner previously described.

Figure 18:
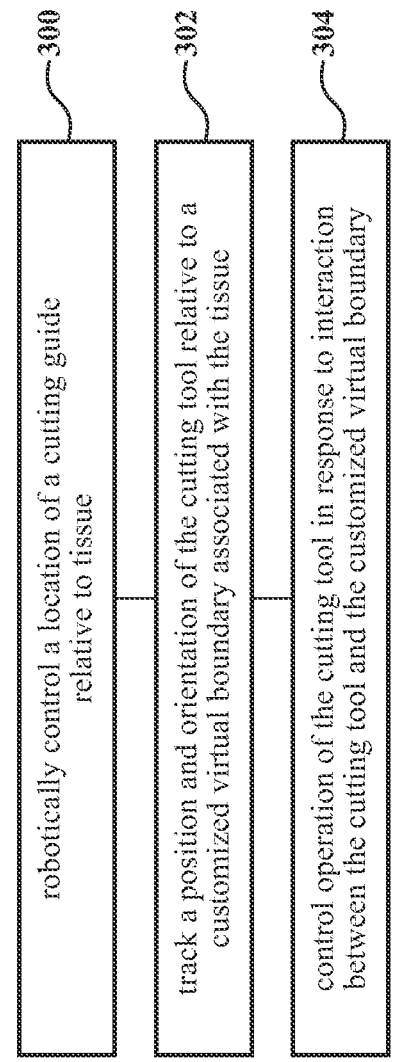

Referring to FIG. 18, in some versions, various control methods may be employed when the cutting tool 40 is tracked by the navigation system 14 or a separate navigation system, in addition to the cutting guide 38 being tracked, so that the control system (e.g., the tool controller 62) is able to control operation of the cutting tool 40 based on a location of the cutting tool 40 relative to the tissue of the patient. Such control may include ceasing operation of the motor MT, varying a speed of the motor MT, or the like.

Similarly, for other types of cutting tools, such as RF tools, ultrasonic tools, lasers, or the like, the control system may be able to control the associated RF energy applied to the tissue (e.g., shut down, vary, etc.), control vibration of an ultrasonic tip (e.g., shut down, vary, etc.), control power (e.g., shut down, vary, etc.), or the like. FIG. 18 illustrates steps that may be taken in one method. In step 300, the cutting guide 38 is first robotically placed at a desired location relative to the tissue. Such robotic control may comprise control of the robotic manipulator 22 in the free mode, haptic mode, semi-autonomous mode, or the like. In step 302, the position and/or orientation of the cutting tool 40 is tracked relative to a virtual object, such as a customized virtual boundary associated with tissue, as described above. In step 304, operation of the cutting tool 40 is controlled in response to interaction between the cutting tool 40 and the customized virtual boundary, for instance, to prevent the cutting tool 40 from cutting tissue not intended to be cut, as previously described.

Figure 19:
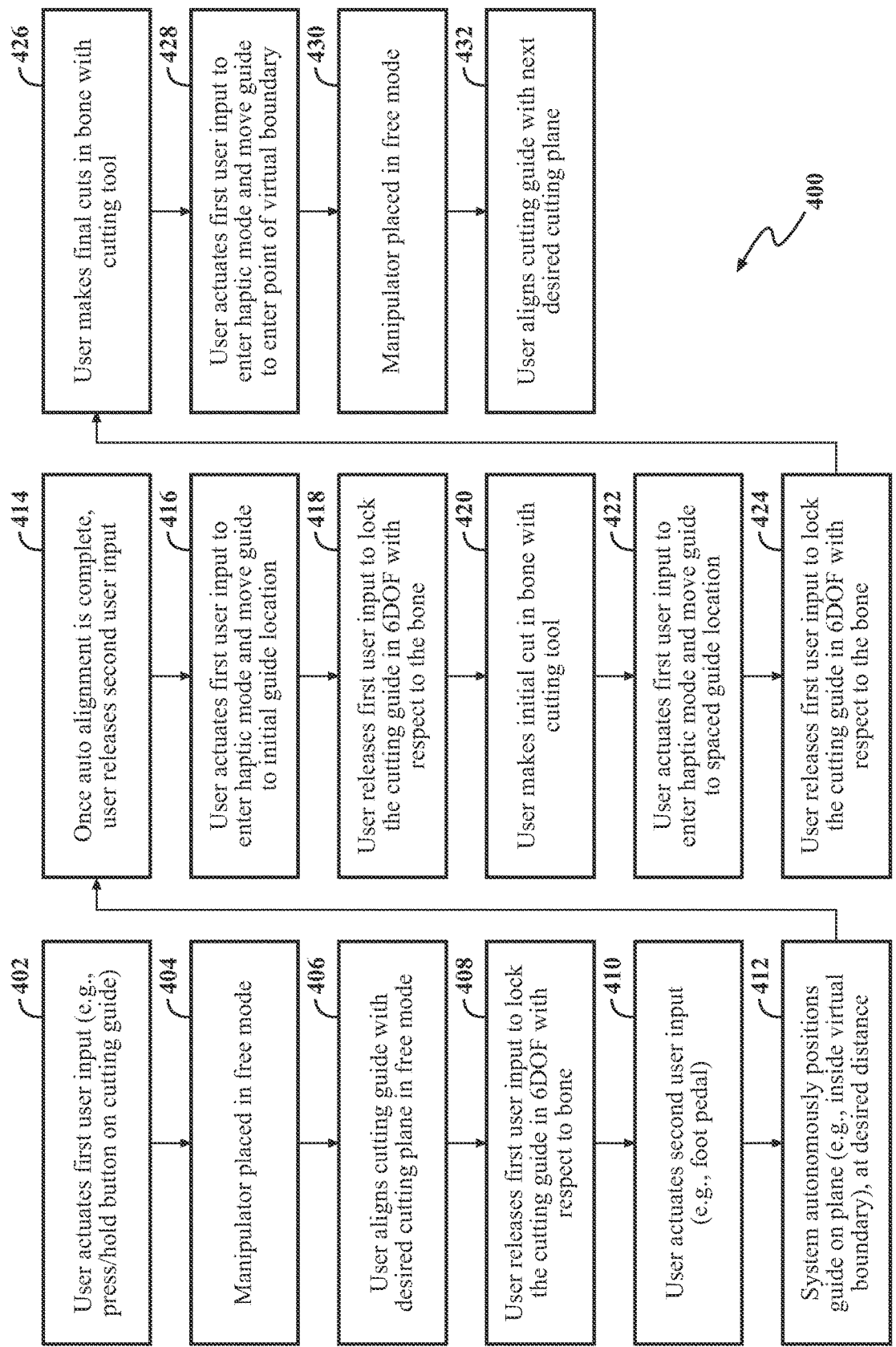
FIG. 19 illustrates steps that may be carried out in one example.

FIG. 19 illustrates a detailed example of steps 400 carried out by the control system to perform a surgical procedure. It should be appreciated that the steps set forth in FIG. 19 are merely exemplary and variations of these are contemplated. Moreover, various forms of user input are described below to provide input into the control system. However, other forms of user input are also contemplated. Suitable user input devices that may be utilized in carrying out the input functions described herein, include, but are not limited to: push buttons on surgical instrument 42, cutting guide 38, manipulator 22, and/or elsewhere; gesture control devices; touchscreens (e.g., associated with display 20); sensors; switches; foot pedals; specified movements/manipulation of the navigation pointer P, cutting tool 40, manipulator 22, or other devices; input from the force/torque sensor 60; and the like.

Initially, the manipulator is locked and held in its current position and orientation by the control system. This may be accomplished by the manipulator controller 34 actively powering the joint motors to keep the current position and orientation, such as by countering the effects of gravity, by not reacting to any user-applied forces/torques on the cutting guide 38, etc. In step 402, the user actuates a first user input operatively coupled to the manipulator controller 34 and/or navigation controller 48 to provide corresponding input (e.g., a button located on the cutting guide 38). This may comprise pressing the user input and holding the user input in an actuated state (e.g., continuously depressing the button). As a result, the control system places the manipulator 22 in the free mode in step 404 and allows the user to apply forces and torques on the cutting guide 38 to move the cutting guide 38 and align the cutting guide 38 with the desired cutting plane, in step 406. Such input could be accomplished by toggling the user input as well, or by some other form of user input.

The display 20 may show a real-time update of the current position and orientation of the cutting guide 38 with respect to a current position and orientation of the desired cutting plane. As a result, the user may perform the manual alignment of the cutting guide 38 in step 406 by monitoring the display 20 until the display 20 shows that the cutting guide 38 is at or near a desired pose. The visual representation of the cutting guide 38 and/or the desired cutting plane on the display 20 could be a 2-D or 3-D representation of the cutting guide 38 and/or a representation of the cutting tool 40 (as though already present in the cutting guide 38 even though not yet inserted therein) so that the user is able to visually align the cutting guide 38 onto the desired cutting plane. Audible, tactile, or other feedback could also be used to help the user manually align the cutting guide 38 onto the desired cutting plane or relative to the virtual boundary associated with the desired cutting plane.

In step 408, the user releases the first user input, toggles the first user input to a different state, or otherwise provides input that indicates that the user has completed manual alignment. In response, the control system locks and holds the cutting guide 38 in its current position and orientation relative to the bone of the patient 12. This may be accomplished by the manipulator controller 34 actively powering the joint motors to keep the current relative position and orientation, such as by countering the effects of gravity, by not reacting to any user-applied forces/torques on the cutting guide 38, etc. Additionally, the navigation controller 48 actively monitors the bone to detect any movement, and continuously transmits updated navigation data to the manipulator controller 34 so that the manipulator controller 34 can move the manipulator 22 accordingly, to maintain the relationship between the cutting guide 38 and the bone.

In some cases, the manual alignment performed by the user is sufficient to place the cutting guide 38 at the desired pose relative to the bone. In some cases, additional, more precise movements may be required that are difficult to accomplish in free mode. In step 410, for example, the user may actuate a second user input (e.g., a foot pedal operatively connected to the manipulator controller 34 and/or the navigation controller 48) to provide input to the control system to indicate a desire to move the cutting guide 38 from its current pose into precise alignment with the desired cutting plane (e.g., to place the cutting guide at the desired pose relative to the virtual boundary). In response to such input, the manipulator controller 34 operates in the autonomous alignment mode described above in step 412 and places the cutting guide 38 onto the desired cutting plane, at a predefined distance away from the bone, e.g., 100 mm away from bone. Once autonomous alignment is complete, then the user releases the second user input in step 414 and the cutting guide 38 is locked in its current pose relative to the bone.

In step 416, the first user input (or another user input) is actuated to enter the haptic mode such that the manipulator 22 switches from being held in 6-DOF (degrees of freedom), in which the pose of the cutting guide 38 is maintained/held relative to the bone, to being able to move in 3-DOF, i.e., the user is able to move the cutting guide 38 in any manner so long as the cutting guide 38 is kept on the desired cutting plane. In other words, the manipulator controller 34 responds to user-applied forces and torques in the haptic mode to move within the desired cutting plane, but not off the cutting plane. So, any forces and torques applied by the user that would otherwise result in any tilting out of the plane, or moving off the plane are ignored. This may be accomplished by zeroing any user-applied forces and torques measured by the force/torque sensor 60 that would otherwise result in such undesired movement and only responding to the components of those forces and torques in the desired cutting plane, i.e., forces in the direction of the plane and rotation in the plane. By virtue of operating in the haptic mode, the user is able to move the cutting guide 38 to the initial guide location or other similar location closer to the bone. When the user releases the first user input (or other input), the manipulator 22 is again held relative to the bone in step 418. In step 420, the user can then make the initial cut in the bone with the cutting tool 40 by placing the cutting tool 40 relative to the cutting guide 38, e.g., as shown in FIGS. 5C and 5D.

In some versions, the entire cut can be made at the initial guide location. In other versions, the cutting guide 38 is repositioned away from the bone to continue making the planar cut. For example, in step 422, the user may actuate the first user input to again enter the haptic mode and associated 3-DOF movement to move the cutting guide 38 to the spaced guide location, such as shown in FIG. 5E. When the first user input is released, the manipulator 22 again holds the cutting guide 38 in 6-DOF relative to the bone in step 424. In step 426, the user can then finish making the necessary cuts to the bone.

In some versions, the cutting guide 38 may be of such size (e.g., relatively small) that the user may need to move the cutting guide 38 laterally in the desired cutting plane from lateral and medial cut guide positions (e.g., compare FIGS. 8D, 8E) so that the cutting tool 40 is able to reach the entire volume of bone to be removed. This may be accomplished by transitioning to the haptic mode via the first user input to allow lateral movement of the cutting guide 38 in the desired cutting plane (e.g., from the location shown in FIG. 8D to 8E). The virtual boundary may be sized so that the cutting guide 38 may be moved laterally in the desired cutting plane, but within predefined limits (e.g., so that the cutting tool 40 does not extend beyond the patient-specific cutting boundary PSCB), as described above.

Once cutting is complete, the first user input can be actuated again to transition into the haptic mode in step 428 so that the user can back the cutting guide 38 away from the bone until the cutting guide 38 reaches an exit point in which the cutting guide 38 exits the virtual boundary associated with the desired cutting plane. Additionally, or alternatively, once the user backs the cutting guide 38 by at least a predefined distance from the bone, e.g., 150 mm, the virtual boundary may be disabled and the manipulator controller 34 may automatically enter the free mode, such as in step 430, and the user can then manually align the cutting guide 38 with the next desired cutting plane in step 432.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical system for use with a surgical tool that is hand-guided, the surgical system comprising:
a robotic manipulator;
a tool guide configured to be coupled to the robotic manipulator and configured to receive and guide the surgical tool to enable the surgical tool to manipulate a bone; and
a control system configured to operate the robotic manipulator to:
autonomously align the tool guide to a target orientation relative to the bone;
enable a user to control movement of the tool guide to an initial guide location adjacent to the bone;
maintain alignment of the tool guide with the target orientation in the initial guide location, wherein the initial guide location is adapted to enable the surgical tool to perform an initial manipulation of the bone;
facilitate withdrawal of the tool guide away from the initial guide location to a spaced guide location after the initial manipulation of the bone; and
maintain alignment of the tool guide with the target orientation at the spaced guide location, wherein the spaced guide location is adapted to enable the surgical tool to perform a further manipulation of the bone.

2. The surgical system of claim 1, wherein the control system is configured to operate the robotic manipulator to facilitate autonomous withdrawal of the tool guide from the initial guide location to the spaced guide location.

3. The surgical system of claim 1, wherein the control system is configured to operate the robotic manipulator to:
facilitate withdrawal of the tool guide from the initial guide location to the spaced guide location in response to a user-applied movement; and
constrain movement of the tool guide during the user-applied movement of the tool guide.

4. The surgical system of claim 1, wherein the control system is configured to determine the spaced guide location for the tool guide based on one or more parameters associated with the surgical tool.

5. The surgical system of claim 1, comprising a navigation system comprising a localizer and a display device, wherein the navigation system is configured to:
track, with the localizer, a pose of the tool guide relative to a pose of the bone; and
generate, on the display device, a visual representation of a region of the bone capable of being reached by the surgical tool when the tool guide is in the spaced guide location.

6. The surgical system of claim 1, comprising a navigation system including a localizer configured to generate tracking data for the tool guide, the bone, and the surgical tool, wherein the initial guide location and the spaced guide location for the tool guide are determined based on tracking data.

7. The surgical system of claim 1, comprising a navigation system including a localizer to track the bone, wherein the navigation system is configured to determine, from the localizer, a velocity or acceleration of the bone, and the control system is configured to:
operate the robotic manipulator in a free mode in response to the velocity or acceleration of the bone exceeding a predetermined limit; and
autonomously re-align the tool guide to the target orientation relative to the bone in response to the velocity or acceleration being at or below the predetermined limit.

8. The surgical system of claim 1, comprising a navigation system including a localizer configured to optically track one or more tracking elements coupled to one or more of: the bone; the surgical tool; and the tool guide, and wherein the control system is configured to facilitate withdrawal of the tool guide away from the initial guide location in response to one or more of the tracking elements being blocked from view of the localizer.

9. The surgical system of claim 1, wherein the control system comprises one or more sensors to measure one or more forces and torques applied by the user to one or more of the tool guide and the robotic manipulator, and the control system being configured to operate the robotic manipulator in a free mode in response to the one or more forces and torques exceeding a predetermined limit.

10. The surgical system of claim 1, wherein the control system comprises one or more sensors coupled to the tool guide to sense a deflection load applied on the tool guide by the surgical tool, and in response to the deflection load exceeding a predetermined limit, the control system is configured to:
activate an indicator; and/or
instruct deactivation of a motor of the surgical tool.

11. A method of operating a surgical system for use with a surgical tool that is hand-guided, the surgical system comprising a robotic manipulator, a tool guide configured to be coupled to the robotic manipulator and configured to receive and guide the surgical tool to enable the surgical tool to manipulate a bone, and a control system, the method comprising:
operating, with the control system, the robotic manipulator for:
autonomously aligning the tool guide to a target orientation relative to the bone;
enabling a user to move the tool guide to an initial guide location adjacent to the bone;
maintaining alignment of the tool guide with the target orientation in the initial guide location, wherein the initial guide location is adapted for enabling the surgical tool to perform an initial manipulation of the bone;
facilitating withdrawal of the tool guide away from the initial guide location to a spaced guide location after the initial manipulation of the bone; and
maintaining alignment of the tool guide with the target orientation at the spaced guide location, wherein the spaced guide location is adapted for enabling the surgical tool to perform a further manipulation of the bone.

12. The method of claim 11, wherein facilitating withdrawal of the tool guide from the initial guide location to the spaced guide location further comprises autonomously withdrawing the tool guide.

13. The method of claim 11, wherein facilitating withdrawal of the tool guide from the initial guide location to the spaced guide location further comprises:
facilitating withdrawal of the tool guide in response to a user-applied movement; and
constraining, with the robotic manipulator, movement of the tool guide during the user-applied movement of the tool guide.

14. The method of claim 11, comprising determining, with the control system, the spaced guide location for the tool guide based on one or more parameters associated with the surgical tool.

15. The method of claim 11, wherein the surgical system includes a navigation system comprising a localizer and a display device, and the method comprising:
- tracking, with the localizer, a pose of the tool guide relative to a pose of the bone; and
- generating, on the display device, a visual representation of a region of the bone capable of being reached by the surgical tool when the tool guide is in the spaced guide location.

16. The method of claim 11, wherein the surgical system includes a navigation system comprising a localizer, and the method comprising:
- generating, with the localizer, tracking data for the tool guide, the bone, and the surgical tool; and
- determining, with the control system, the initial guide location and the spaced guide location for the tool guide based on tracking data.

17. The method of claim 11, wherein the surgical system includes a navigation system comprising a localizer, the method comprising:
- tracking the bone with the localizer;
- determining, from the localizer, a velocity or acceleration of the bone;
- operating, with the control system, the robotic manipulator in a free mode in response to the velocity or acceleration of the bone exceeding a predetermined limit; and
- operating, with the control system, the robotic manipulator for autonomously re-aligning the tool guide to the target orientation relative to the bone in response to the velocity or acceleration being at or below the predetermined limit.

18. The method of claim 11, wherein the surgical system includes a navigation system comprising a localizer configured to optically track one or more tracking elements coupled to one or more of: the bone; the surgical tool; and the tool guide, and the method comprising:
- detecting, with the navigation system, one or more of the tracking elements being blocked from view of the localizer; and
- operating, with the control system, the robotic manipulator for facilitating withdrawal of the tool guide away from the initial guide location in response to one or more of the tracking elements being blocked from view of the localizer.

19. The method of claim 11, wherein the control system comprises one or more sensors to measure one or more forces and torques applied by the user to one or more of the tool guide and the robotic manipulator, and the method comprising:
- determining, with the control system, the one or more forces and torques exceeding a predetermined limit; and
- operating, with the control system, the robotic manipulator in a free mode in response to the one or more forces and torques exceeding the predetermined limit.

20. A method of operating a surgical system, the surgical system comprising a surgical tool that is hand-guided, a robotic manipulator supporting a tool guide, the tool guide configured to receive and guide the surgical tool to enable the surgical tool to manipulate a bone, and a control system, the method comprising:
- autonomously aligning the tool guide to a target orientation relative to the bone;
- moving the tool guide to an initial guide location adjacent to the bone;
- maintaining alignment of the tool guide with the target orientation in the initial guide location;
- guiding the surgical tool with the tool guide being in the initial guide location for enabling the surgical tool to perform an initial manipulation of the bone;
- facilitating withdrawal of the tool guide away from the initial guide location to a spaced guide location after the initial manipulation of the bone;
- maintaining alignment of the tool guide with the target orientation at the spaced guide location; and
- guiding the surgical tool with the tool guide being in the spaced guide location for enabling the surgical tool to perform a further manipulation of the bone.

* * * * *